United States Patent
Melton et al.

(10) Patent No.: US 11,672,595 B1
(45) Date of Patent: Jun. 13, 2023

(54) SYSTEMS AND METHODS FOR INTERRUPTING NERVE ACTIVITY TO TREAT A MEDICAL CONDITION

(71) Applicant: Corveus Medical, Inc., Houston, TX (US)

(72) Inventors: Tyler Melton, Houston, TX (US); Byron Smith, Houston, TX (US)

(73) Assignee: Corveus Medical, Inc., Houston, TX (US)

( * ) Notice: Subject to any disclaimer, the term of this patent is extended or adjusted under 35 U.S.C. 154(b) by 0 days.

(21) Appl. No.: 17/841,424

(22) Filed: Jun. 15, 2022

(51) Int. Cl.
| | |
|---|---|
| A61B 18/14 | (2006.01) |
| A61B 18/00 | (2006.01) |
| A61B 17/34 | (2006.01) |
| A61M 25/09 | (2006.01) |
| A61B 18/12 | (2006.01) |
| A61M 25/01 | (2006.01) |

(52) U.S. Cl.
CPC ...... *A61B 18/1492* (2013.01); *A61B 17/3478* (2013.01); *A61B 2018/00083* (2013.01); *A61B 2018/00357* (2013.01); *A61B 2018/00434* (2013.01); *A61B 2018/00577* (2013.01); *A61B 2018/126* (2013.01); *A61B 2018/1425* (2013.01); *A61B 2018/1467* (2013.01); *A61M 25/0108* (2013.01); *A61M 25/09* (2013.01)

(58) Field of Classification Search
CPC ............ A61B 18/1492; A61B 17/3478; A61B 2018/00083; A61B 2018/00357; A61B 2018/00434; A61B 2018/00577; A61B 2018/126; A61B 2018/1425; A61B 2018/1467
See application file for complete search history.

(56) References Cited

U.S. PATENT DOCUMENTS

| | | |
|---|---|---|
| 6,217,527 B1 | 4/2001 | Selmon et al. |
| 6,221,049 B1 | 4/2001 | Selmon et al. |
| 6,235,000 B1 | 5/2001 | Milo et al. |

(Continued)

FOREIGN PATENT DOCUMENTS

| | | |
|---|---|---|
| WO | WO-2019118976 A1 | 6/2019 |
| WO | WO-2019148094 A1 | 8/2019 |

*Primary Examiner* — Michael F Peffley
*Assistant Examiner* — Bo Ouyang
(74) *Attorney, Agent, or Firm* — Wilson Sonsini Goodrich & Rosati; Dustin M. Luettgen, Esq.

(57) ABSTRACT

Provided are devices, systems, and methods for treating or preventing heart failure or a symptom of heart failure through coordinated nerve activity interruption for one or more target nerves. Devices disclosed herein may comprise a vascular catheter comprising a telescopic needle assembly configured to puncture vascular tissue in contact with the catheter, wherein the needle assembly comprises one or more electrodes configured to deliver electrical energy to a tissue in contact with the one or more electrodes. Methods may include treating or preventing heart failure or a symptom of heart failure by inserting a catheter into a vascular tissue of the subject; guiding the catheter towards the greater splanchnic nerve; piercing the vascular tissue of the subject with a telescopic needle assembly extending outwards from the catheter towards the target nerve; and ablating the target nerve by delivering a stimulation energy to the target nerve with one or more electrodes.

20 Claims, 21 Drawing Sheets

(56) References Cited

U.S. PATENT DOCUMENTS

| | | | |
|---|---|---|---|
| 6,511,458 B2 | 1/2003 | Milo et al. | |
| 6,514,217 B1 | 2/2003 | Selmon et al. | |
| 6,719,725 B2 | 4/2004 | Milo et al. | |
| 7,004,173 B2 | 2/2006 | Sparks et al. | |
| 8,512,333 B2 | 8/2013 | Epstein et al. | |
| 8,880,185 B2 | 11/2014 | Hastings et al. | |
| 9,192,435 B2 | 11/2015 | Jenson | |
| 9,278,196 B2 | 3/2016 | Fischell et al. | |
| 9,427,579 B2 | 8/2016 | Fain et al. | |
| 9,931,046 B2 | 4/2018 | Fischell et al. | |
| 9,943,666 B2 | 4/2018 | Warnking | |
| 10,118,004 B2 | 11/2018 | Fischell et al. | |
| 10,376,308 B2 | 8/2019 | Levin et al. | |
| 10,405,912 B2 | 9/2019 | Fischell et al. | |
| 10,716,618 B2 | 7/2020 | Wright et al. | |
| 10,912,610 B2 | 2/2021 | Levin et al. | |
| 2005/0080409 A1* | 4/2005 | Young | A61B 18/1492 606/41 |
| 2012/0071870 A1* | 3/2012 | Salahieh | A61B 1/00082 606/33 |
| 2013/0274673 A1 | 10/2013 | Fischell et al. | |
| 2013/0274674 A1 | 10/2013 | Fischell et al. | |
| 2015/0119875 A1* | 4/2015 | Fischell | A61B 18/1492 606/41 |
| 2015/0351831 A1* | 12/2015 | Janssen | A61B 90/30 606/41 |
| 2019/0117298 A1* | 4/2019 | Beeckler | A61B 18/082 |
| 2019/0175912 A1 | 6/2019 | Gelfand et al. | |
| 2019/0183569 A1 | 6/2019 | Panescu et al. | |
| 2020/0022751 A1 | 1/2020 | Denison et al. | |
| 2020/0179045 A1 | 6/2020 | Levin et al. | |
| 2020/0197079 A1 | 6/2020 | Fischell et al. | |

* cited by examiner

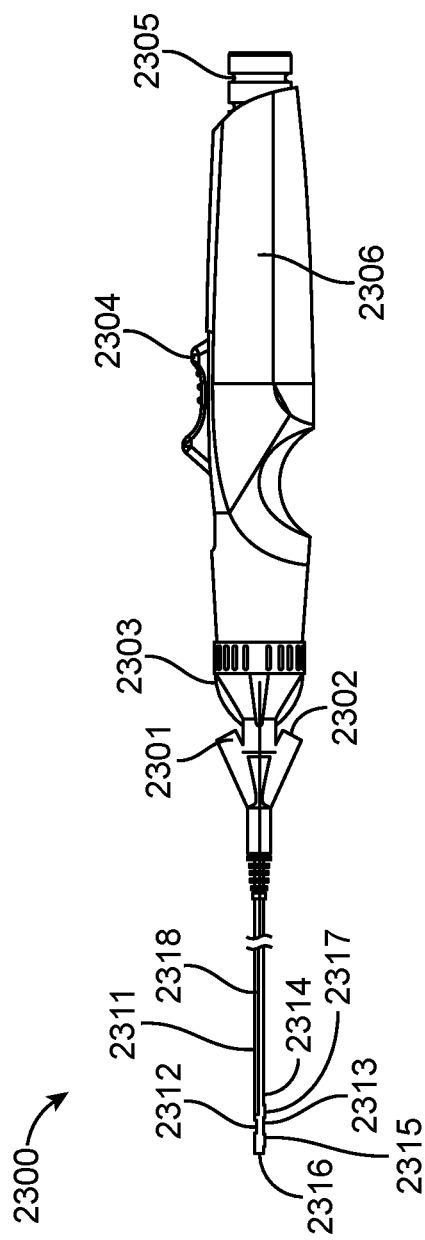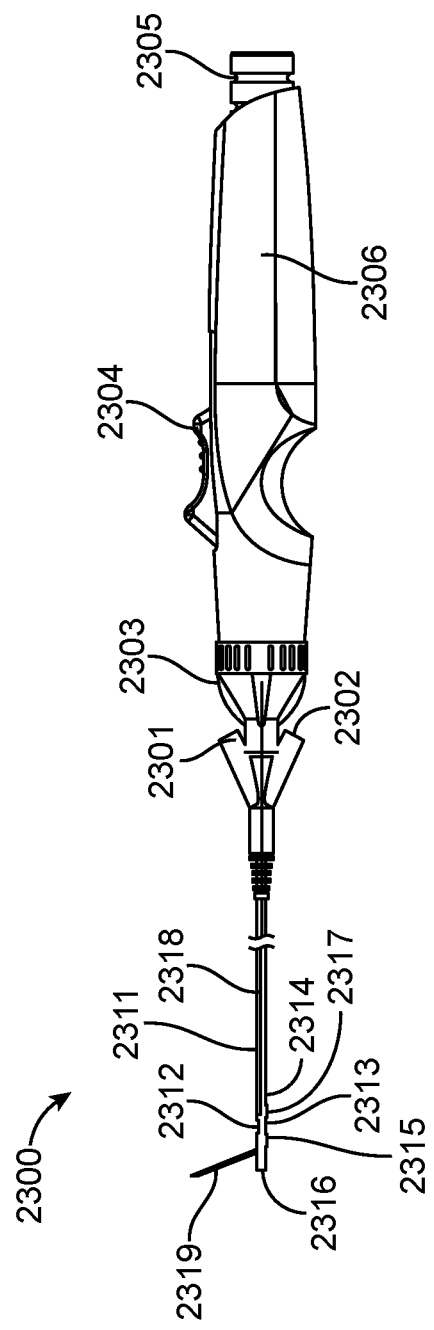
FIG. 23A
FIG. 23B

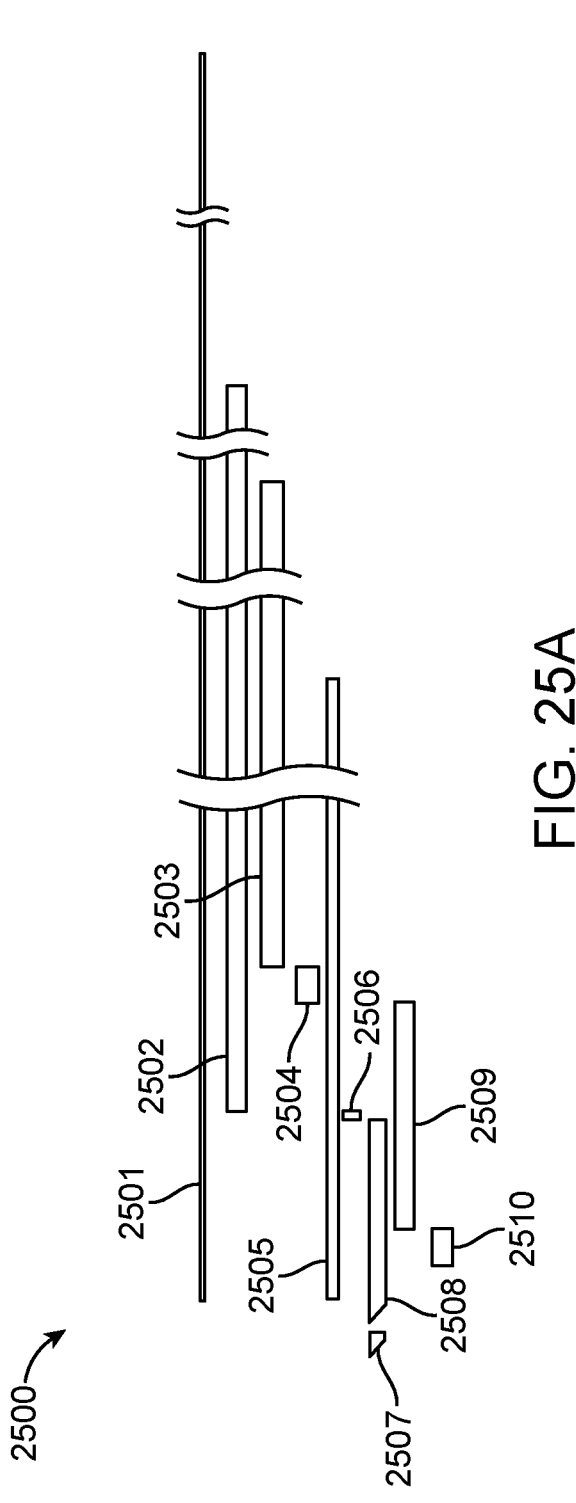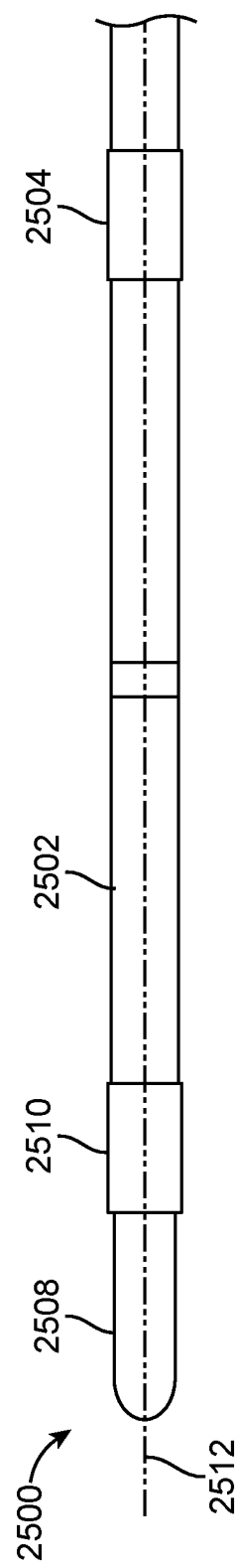
FIG. 25A
FIG. 25B

SYSTEMS AND METHODS FOR INTERRUPTING NERVE ACTIVITY TO TREAT A MEDICAL CONDITION

BACKGROUND OF THE INVENTION

Heart failure affects over 6 million subjects. In some instances, heart failure is characterized by muscle weakening, resulting in inefficient cardiac pump action. As a result, forward blood flow in some instances of heart failure is poor, which can cause a backup of blood and an accumulation of pressure in the heart and pulmonary circuit. Thus, intracardiac blood pressure may increase, leading to symptoms, such as an onset of congestion, shortness of breath, and/or respiratory failure. In some instances, traditional methods for relieving pressure volume burden on the cardiopulmonary circuit includes removing the fluid buildup (e.g., fluid within blood vessels and tissues), thereby potentially relieving heart failure symptoms. However, for most patients, the current standard of care for treating heart failure patients is often limited only to medication such as ACE inhibitors, angiotensin-2 receptor blockers (ARBs), beta blockers, mineralocorticoid receptor antagonists, diuretics, ivabradine, sacubitril valsartan, hydralazine with nitrate, and/or digoxin; with the goal of reducing pressure volume burden on the cardiopulmonary circuit. There remains a need in the art for alternative methods of treating heart failure other than medication.

SUMMARY OF THE INVENTION

It is appreciated by the inventors that treating heart failure or a symptom thereof may be accomplished by means of nerve ablation to a branch of the splanchnic nerve, and that such an alternative treatment may improve upon the current medication based standard of care for heart failure patients. It is further appreciated by the inventors that the current medication based standard of care is inadequate for a number of heart failure patients, and that treatment of heart failure can be improved by nerve ablation.

For example, a common symptom of heart failure includes increased intracardiac blood pressure and accumulation of blood within the cardiopulmonary circuit, and if a subject is suffering from late state heart failure, it may take too long for the standard of care medications to reduce the intracardiac pressure to prevent hospitalization, for example, due to low bioavailability of medications, or the significant time required to pharmacologically reduce fluid build-up within the body. Other patients who are prescribed standard of care medications to reduce the intracardiac pressure may be unresponsive the medications, may not be able to take certain medications due to drug interactions or other comorbidities, or may require non-standardized dosages of medications to achieve efficacy, all of which may limit the efficacy of the medications. In other cases, subjects suffering from early-stage heart failure may not meet the criteria for hospitalization to treat heart failure, and may be denied hospitalization until such time as their condition becomes critical. Almost any heart failure patient could benefit from a non-medication based approach treating heart failure or a symptom thereof, and especially patients who are at risk of worsening heart failure but who do not yet meet hospitalization criteria, for example, patients rated between 2-3 on the New York Heart Association 1-4 rating scale.

Accordingly, disclosed herein is a method of treating heart failure or a symptom thereof by inactivating the greater splanchnic nerve. Nerve ablation of the greater splanchnic nerve can inactivate aspects of the sympathetic nervous system, reduce intracardiac blood pressure and accumulation of blood within the cardiopulmonary circuit, and reduce the likelihood that a heart failure patient will require hospitalization, without requiring pharmacological intervention.

It is further appreciated by the inventors that current devices and methods for ablation of the greater splanchnic nerve may utilize electrode assemblies which are prone to failure or which may lead to unnecessary trauma to vascular tissue and surrounding tissues relative to what is required to nerve ablation. For example, current methods for the destruction of the greater splanchnic nerve may include an open heart surgery, requiring opening of the sternum, reflection of vital organs (including heart and lung) to reach the splanchnic nerve, and physically lysing the nerve with a scalpel or other device. Such a procedure is highly invasive, and places increased strain upon the subject's heart, which is unacceptable for a subject already suffering from heart failure. Another method used for ablation of the greater splanchnic nerve include piercing a subject's back with a needle, driving the needle through the subject's aorta and to access the greater splanchnic nerve, which places considerable risks on surrounding organs, including the lung, heart, and aorta. In other cases, non-telescopic electrode assemblies utilized for nerve ablation may induce sharp force trauma to the vascular tissue, and tissues surrounding the target nerve. Accordingly, aspects disclosed herein provide for nerve ablation catheter devices comprising improved needle assemblies which can be used to access the greater splanchnic nerve through the vascular system of the subject, and which do not require piercing the aorta with a needle in order to access the greater splanchnic nerve. Such devices may be especially useful in carrying out the methods of treating heart failure or a symptom described herein by permitting nerve ablation to a branch of the splanchnic nerve in a less invasive manner which does not place an increased strain upon the subject's heart, and which minimizes sharp force trauma to the vascular tissue, and tissues surrounding the target nerve. Such improved needle assemblies may also be easier to manufacture and experience a reduced rate of error due to the prevention of adhesion of tissue to inner surfaces of the needle assembly.

Aspects disclosed herein provide a method of treating or preventing heart failure or a symptom of heart failure in a subject in need thereof comprising: inserting a catheter into a vascular lumen defined by a vascular tissue of the subject; guiding the catheter towards a location proximal to a target nerve, the target nerve comprises the greater splanchnic nerve; piercing the vascular tissue of the subject with a telescopic needle assembly extending outwards from the catheter towards the target nerve, the needle assembly comprises an electrode assembly, with the telescopic needle assembly having a first section surrounding a second section, wherein the second section extends outwards from the first section; delivering a stimulation energy to the target nerve with the electrode assembly; thereby fully or partially ablating the target nerve and treating or preventing heart failure or a symptom of heart failure in the subject. In some embodiments, treating or preventing heart failure or a symptom of heart failure in the subject comprises reducing intracardiac blood pressure, or reducing an accumulation of blood within a cardiopulmonary circuit of the subject. In some embodiments, the method further includes: delivering a preliminary stimulation energy to the target nerve prior to piercing the vascular tissue of the subject, or delivering a preliminary stimulation energy to the target nerve after piercing the vascular tissue of the subject, or combinations thereof; measuring a physiological response corresponding to the preliminary stimulation energy, thereby indicating whether the location proximal to the target nerve is in sufficient proximity to the target nerve. In some embodiments, the physiological response comprises nerve activity, muscle movement, cardiac activity, adverse changes in pulmonary capillary wedge pressures (PCWP), gastrointestinal changes including increased motility, increase or decrease in less palmer sweating, increase or decrease in temperature for rectal and/or skin measurement, increase or decrease in renal output in relation to changes in vascular dilation, decrease in metabolism, decreased glucose release, decreased glucagon release, or increases in brain natriuretic peptide. In some embodiments, the physiological response comprises measurement of action potential through the target nerve. In some embodiments, an insufficient physiological response corresponding to the preliminary stimulation energy is measured, indicating the location proximal to the target nerve is not in sufficient proximity to the target nerve. In some embodiments, the method further includes re-guiding the catheter towards a second location proximal to a target nerve, the second location is in closer proximity to the target nerve than the first location. In some embodiments, a sufficient physiological response corresponding to the preliminary stimulation energy is measured, indicating the location proximal to the target nerve is in sufficient proximity to the target nerve. In some embodiments, the stimulation energy sufficient to ablate the target nerve comprises electrical stimulation. In some embodiments, delivering a stimulation energy to the target nerve with the electrode assembly sufficient to ablate the target nerve comprises heating the target nerve, or a portion thereof, to about 50, 55, 60, 65, 70, 75, 80, 85, or 90 C. In some embodiments, the method further includes orientating the catheter within the vascular tissue of the subject such that it is in a direction that aligns the needle assembly with the target nerve. In some embodiments, the method further includes orientating the catheter within the vascular tissue of the subject such that it is in a direction that aligns the needle assembly with the target nerve using a radiographic marker. In some embodiments, orientating the catheter comprises orientating the needle assembly in a direction that aligns the electrode assembly with the target nerve. In some embodiments, orientating the catheter comprises rotating the catheter such that the needle assembly extends from the catheter to the target nerve. In some embodiments, the method further includes: delivering a confirmatory stimulation energy following ablating the target nerve; measuring a physiological response, or a change in physiological response, corresponding to the confirmatory stimulation energy, thereby confirming an interrupted nerve activity of the target nerve. In some embodiments, a physiological response corresponding to the confirmatory stimulation energy is measured, indicating the ablating the target nerve was unsuccessful. In some embodiments, the method further includes delivering the stimulation energy to the target nerve with the electrode assembly, thereby repeating ablating the target nerve. In some embodiments, the target nerve is a greater splanchnic nerve. In some embodiments, the target nerve is a left branch, a right branch, a lesser branch, or a least branch of the greater splanchnic nerve. In some embodiments, guiding the catheter towards the location proximal to the target nerve comprises guiding the catheter towards the ninth thoracic vertebra (T9), the tenth thoracic vertebra (T10), the eleventh thoracic vertebra (T11), the twelfth thoracic vertebra (T12), or the first lumbar vertebra (L1). In some embodiments, the stimulation energy is from about 10 W to about 100 W. In some embodiments, the stimulation energy is from about 25 W to about 75 W. In some embodiments, the stimulation energy is about 30, 35, 40, 45, 50, 55, 60, 65, or 70 W. In some embodiments, the stimulation energy is about 50 W.

Aspects disclosed herein provide a vascular catheter comprising: a longitudinal axis; a distal end; a proximal end; a catheter shaft comprising an exit port; a needle assembly lumen comprising a telescopic needle assembly configured to extend through the exit port and puncture vascular tissue in contact with the catheter, the needle assembly comprises one or more electrodes configured to deliver electrical energy to a tissue in contact with the one or more electrodes, wherein the telescopic needle assembly comprises a first section surrounding a second section, wherein the second section extends outwards from the first section; a guidewire lumen; and a catheter tip. In some embodiments, the vascular catheter further comprises a contrast lumen. In some embodiments, the exit port is positioned on a lateral side of the catheter shaft. In some embodiments, the catheter further includes an electrical surface on the needle assembly. In some embodiments, the catheter further includes a base electrode on an outer surface of the catheter. In some embodiments, the base electrode is positioned within 0-90 degrees radially of a location on the outer surface of the vascular catheter relative to the longitudinal axis of the vascular catheter on an outer surface thereof. In some embodiments, the catheter further includes a plurality of base electrodes on an outer surface of the catheter. In some embodiments, the catheter further includes a first electrical circuit electrically coupled to the one or more electrodes. In some embodiments, the catheter further includes a second electrical circuit electrically coupled to the base electrode. In some embodiments, the catheter is configured to provide electrical energy of differing frequencies to the first electrical circuit and the second electrical circuit. In some embodiments, the needle assembly comprises: one or more tubular bodies; a distal point; a first electrode; a second electrode; a wire connecting the first electrode and the second electrode to a power source; an insulating material insulating the first electrode, the second electrode, and the wire from the vascular catheter. In some embodiments, the wire comprises an enamel coated wire or a multi-strain braid. In some embodiments, the first section comprises a first tubular body, wherein the second section comprises a second tubular body, wherein the first tubular body extends outward from the second tubular body, and wherein the first tubular body nests within the second tubular body such that the tubular body is fully or partially contained within the first tubular body. In some embodiments, the needle assembly further comprises a third section comprising a sharp distal point, wherein the second section surrounds the third section, wherein the third section extends outward from the second section. In some embodiments, the first electrode is positioned on the first tubular body, and the second electrode is positioned on the second tubular body. In some embodiments, the first electrode and the second electrode are positioned on the first tubular body, or the second tubular body. In some embodiments, the needle assembly further comprises an electrically insulating material within the needle assembly, the electrically insulating material comprises a dielectric insulator between the first and second tubular bodies. In some embodiments, the needle assembly further comprises an electrically insulating material within the needle assembly, the electrically insulating material comprises an insulator or a dielectric washer positioned between the first and the second tubular bodies along a circular cross section of the first tubular body or the second tubular body. In some embodiments, the one or more electrodes comprises only a single electrode. In some embodiments, the one or more electrodes comprises two electrodes. In some embodiments, the one or more electrodes comprises three electrodes. In some embodiments, the three electrodes are arranged such that the second electrode is between the first and third electrodes, and wherein the second electrode is a negative electrode and the first and third electrodes are positive electrodes, or wherein adjacent electrodes have opposite polarity. In some embodiments, the three electrodes are arranged such that the second electrode is between the first and third electrodes the second electrode is a positive electrode with the first and third electrodes being negative electrodes. In some embodiments, the catheter is configured to permit ablation between the first and second electrode, or the second and third electrode. In some embodiments, the needle assembly further comprises an electrically insulating material within the needle assembly. In some embodiments, the electrically insulating material comprises a dielectric, a dielectric washer, or a polyimide liner. In some embodiments, when the needle assembly further comprises a third electrode. In some embodiments, when the needle assembly further comprises separate electrical circuits for each electrode. In some embodiments, when the needle assembly extends a prescribed distance from the exit port, and is in proximity to a target nerve and energized, the vascular catheter is configured to ablate a length of the target nerve that is at least as long as or longer than the deployed distance between the first and second tubular bodies. In some embodiments, the insulating material comprises a dielectric washer. In some embodiments, the first electrode and the second electrode are electrically isolated from each other. In some embodiments, the needle assembly is configured to deliver an electric charge in a bipolar manner. In some embodiments, the first electrode and/or the second electrode are in operative communication with a controller configured to modulate a power delivered by a source of energy. In some embodiments, the one or more electrodes comprises a silk-screened electrode. In some embodiments, the one or more electrodes comprises an additive manufactured electrode. In some embodiments, the one or more electrodes comprises a subtractive manufactured electrode. In some embodiments, the catheter further includes a base at the proximal end of the vascular catheter configured to permit for manipulation of the vascular catheter. In some embodiments, the catheter further includes a vascular catheter rotation knob configured to rotate the vascular catheter. In some embodiments, the catheter further includes a rotary electrical connector configured to rotate the catheter or the needle assembly. In some embodiments, the catheter further includes a rotary electrical connector configured to rotate the catheter, the needle assembly, the guidewire port, or the contrast port. In some embodiments, the catheter further includes a rotary electrical connector configured to rotate the catheter or the rotational control knob. In some embodiments, the catheter further includes a rotation coupler configured to rotate the vascular catheter. In some embodiments, the catheter further includes an electrode advancer configured to extend the needle assembly and one or more electrodes through the exit port. In some embodiments, the catheter further includes a guidewire port. In some embodiments, the catheter further includes a contrast port. In some embodiments, the catheter further includes a dielectric material insulating the one or more electrodes from the vascular catheter. In some embodiments, the dielectric material comprise polyimide. In some embodiments, the vascular catheter shaft comprises braid reinforced pebax, an extruded material, nylon, a fibrous material, wire, a multi strain braid, or a material configured to transfer force through a longitudinal axis. In some embodiments, the needle assembly further comprises one or more marker bands. In some embodiments, the marker bands are configured to provide an indication as to positioning of the catheter relative to a vein, with fluoroscopic imaging, or indicate a relative position of the catheter within a vein, artery, or vessel. In some embodiments, the needle assembly further comprises a bifurcated configuration comprising a second tubular body terminating in a sharp point, the first and second tubular bodies are spaced apart when the needle assembly is extended, the first electrode is on the first tubular body, and the second electrode is on the second tubular body.

BRIEF DESCRIPTION OF THE DRAWINGS

For a more complete understanding of the present invention, including features and advantages, reference is now made to the detailed description of the invention along with the accompanying figures:

FIGS. 18-21 provide an exemplary method for treating a medical condition, according to an embodiment described herein, wherein various options, such as different ablation modalities, are provided.

FIG. 23A depicts an exemplary device used for treating a medical condition as described herein.

FIG. 23B depicts an exemplary device used for treating a medical condition as described herein with the needle assembly extended.

FIG. 25A depicts an exploded view of the needle assembly of an exemplary device used for treating a medical condition as described herein.

FIG. 25B depicts the needle assembly of an exemplary device used for treating a medical condition as described herein.

DETAILED DESCRIPTION OF THE INVENTION

Figure 1:
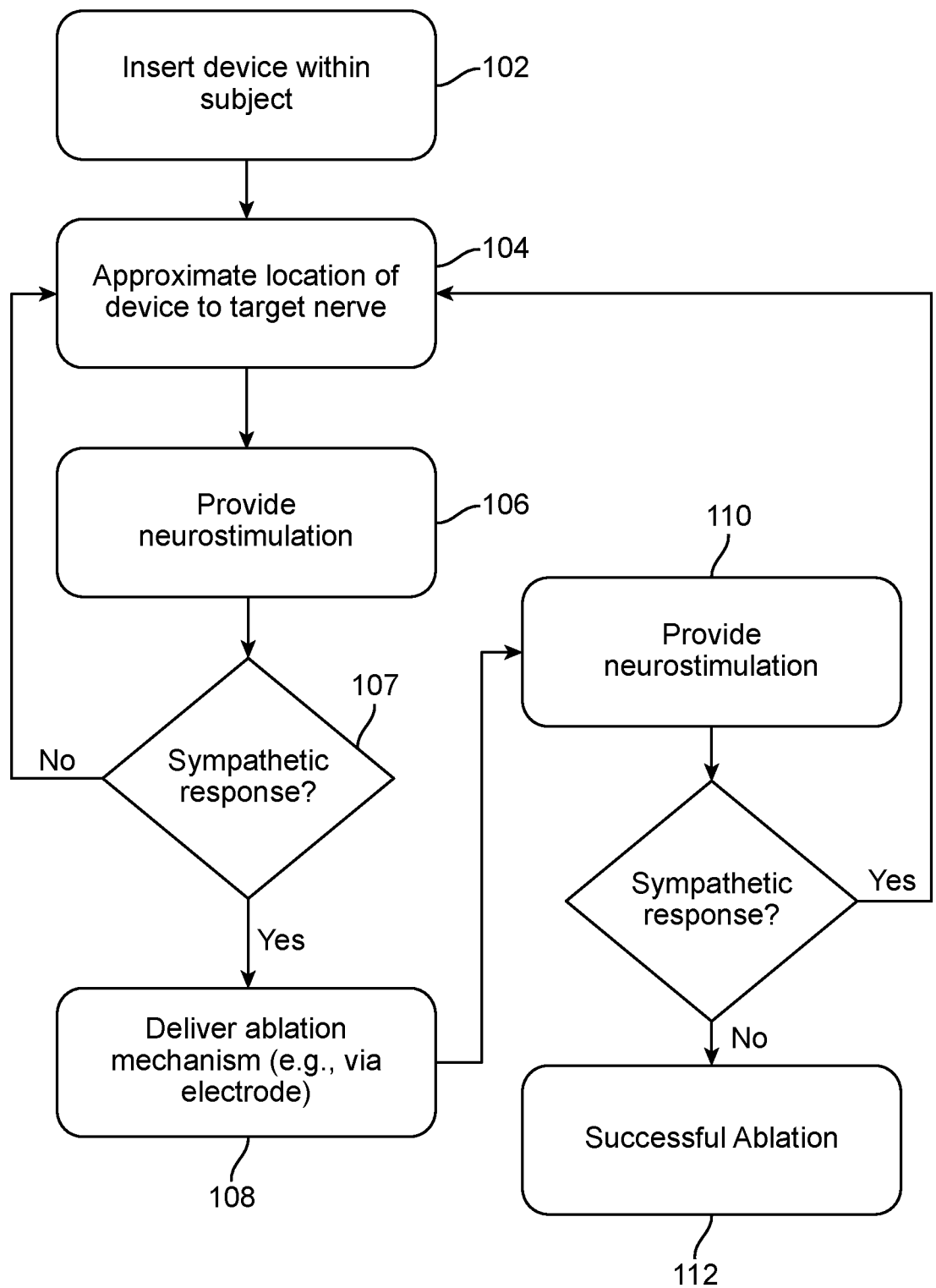
FIG. 1 provides an exemplary flow chart depicting a method for treating a medical condition according to an embodiment described herein.

Provided herein are devices, systems, and methods for treating a medical condition through coordinated nerve activity interruption for one or more target nerves. In some embodiments, the nerve activity interruption triggers a response for treating the medical condition, including alleviating symptoms of said medical condition. In some embodiments, the nerve activity interruption comprises destroying a portion of one or more target nerves. In some embodiments, destroying the portion of one or more target nerves comprises targeting the target nerve at one or more different locations to enable such destruction. In some embodiments, a bifurcated needle assembly having two needles (e.g., needle electrodes as described herein), wherein the tips of each needle are spaced apart, is introduced using a device (e.g., a catheter based device) to enable ablation of the target nerve at one or more different locations, so as to provide a desired length of ablation along a length of the target nerve, resulting in increased duration of a treatment for a medical condition, and further minimizing collateral damage. In some embodiments, the location of the target nerve is confirmed via any combination of fluoroscopy, neurostimulation, and/or nerve sensing to ensure accurate ablation of the target nerve. For example, in some embodiments, neurostimulation enables real-time or substantially real time confirmation of a target nerve location.

In some embodiments, the medical condition comprises heart failure, such as inefficient cardiac pump action, wherein interruption of a target nerve (e.g., denervation of a target nerve), such as the splanchnic nerve, enables for cardiac blood pressure to be alleviated by removing fluid within blood vessels and tissues (e.g., blood buildup in the heart) and sending said removed fluid to the abdominal cavity.

Medical Condition

In some embodiments, systems, devices, and methods described herein are used to treat a medical condition. In some embodiments, as described herein, the medical condition comprises heart failure, constipation, metabolic syndrome (including obesity), hyperhidrosis, hypertension, or others known in the art to be affected by nerve activity interruption of one or more target nerves, or a combination thereof.

Heart failure affects over 6 million subjects. In some instances, heart failure is characterized by muscle weakening, resulting in inefficient cardiac pump action. As a result, forward blood flow in some instances of heart failure is poor, which can cause a backup of blood and an accumulation of pressure in the heart and pulmonary circuit. Thus, intracardiac blood pressure may increase, leading to symptoms, such as an onset of congestion, shortness of breath, and/or respiratory failure. In some instances, traditional methods for relieving pressure volume burden on the cardiopulmonary circuit is by removing fluids within blood vessels and tissues (e.g., fluid buildup, such as blood,), thereby potentially relieving heart failure symptoms.

In some instances, subjects are in a state of compensated heart failure, where there are no cardiopulmonary pressures or symptoms. In some instances, cardiac recovery for such state of compensated heart failure occurs with the aid of medications. In some instances, subjects are caught in a vicious cycle of volume accumulation, hospitalization for fluid removal, and discharge, wherein cardiac recovery does not occur. In some instances, such subjects do not respond to conventional medications.

Accordingly, in some embodiments, systems, methods, and devices described herein are configured to provide a mechanical reduction of intracardiac blood pressures, for example via the redistribution of fluid (e.g., blood) away from the heart, so as to relieve intracardiac pressures.

In some embodiments, fluid (e.g., blood) is redistributed away from the heart to one or more cavities within a subject (e.g., blood vessels within the cavities). In some instances, the abdominal cavity has a high vascular capacity to absorb fluid. Thus, in some instances, by introducing a mechanism to redistribute fluid from the cardiopulmonary circuit to the abdominal cavity, cardiac benefit can occur. In some instances, the vascular capacity is determined by a variety of factors, including autonomic nerve activity. Some of the sympathetic nerves that innervate the abdominal cavity include splanchnic nerves, wherein splanchnic nerves originate from the sympathetic chain in the thoracic cavity, and travel to the abdominal cavity, where they synapse on various ganglia. Sympathetic splanchnic nerve activity results in vascular vasoconstriction in the abdominal cavity. Accordingly, in some embodiments, systems, methods, and devices described herein are configured to inactivate the sympathetic nerve activity (splanchnic nerves) to vasodilate the splanchnic vasculature, and thereby draw fluid to the abdominal cavity. In some instances, there are a plurality of types of interventions to interrupt splanchnic nerve activity to achieve splanchnic vasodilation. In some embodiments, such plurality of types comprise percutaneous means, transvascular means, and/or surgical means.

Method for Reducing Cardiac Blood Pressure

FIG. 1 provides an exemplary method for reducing cardiac blood pressure by redistributing fluid (e.g., blood) from the heart to one or more cavities. In some embodiments, the method comprises interrupting nerve activity (e.g., denervation) of one or more target nerves. In some embodiments, the one or more target nerves is first identified and/or confirmed through one or more sensing techniques described herein, after which the nerve activity of the one or more target nerves is then interrupted. In some embodiments, a device described herein (e.g., a catheter based device) is used to identify and/or confirm the location of one or more target nerves, and/or interrupt nerve activity for the one or more target nerves. As described herein, the one or more target nerves comprise a splanchnic nerve, lumbar sympathetic nerve, sympathetic stellate ganglion, other target nerves known in the art, or any combination thereof. As described herein, in some embodiments, a splanchnic nerve enables treatment for heart failure (as described herein). Examples of branches of the splanchnic nerve include the greater splanchnic nerve (GSN), the lesser splanchnic nerve, and the least splanchnic nerve, any of which (in combination or singularly) may be targeted for treatment of a medical condition. For example, in some instances, the GSN is a branch of the thoracic sympathetic nerve, and is thus configured to provide sympathetic innervation to the abdominal cavity. The GSN traverses the thoracic cavity, travels through the aortic hiatus, and synapses on the celiac ganglion, from wherein it is able to innervate several target organs, including the abdominal vasculature. As such, by inactivating the GSN, the abdominal vasculature dilates, thereby drawing in blood volume from the circulatory system. As described herein, in some instances, volume drawn from the heart will alleviate the pressure burden in the cardiopulmonary system, which can be evidenced, for example by a decreased pulmonary capillary wedge pressure (PCWP)— as described herein.

In some embodiments, targeting the lumbar sympathetic nerve allows for treatment of a peripheral artery disease. In some embodiments, targeting the sympathetic stellate ganglion allows for treatment of ventricular arrhythmias.

For the exemplary method described in FIG. 1, the target nerve comprises the splanchnic nerve, and the cavity receiving the redistributed fluid (e.g., blood flow) comprises the abdominal cavity.

Identification of Target Nerve

In some embodiments, using a device described herein (e.g., a catheter based device), a location of a target nerve is first approximated, after which the target nerve is identified and/or confirmed, to ensure the correct nerve will be targeted for interruption of nerve activity to obtain the desired effect. In some embodiments, confirmation of the nerve activity interruption at the target nerve acts as an exemplary identifier that a desired effect within the subject has occurred (e.g., treatment of a medical condition, such as reduction of intracardiac blood pressure).

Figure 22:
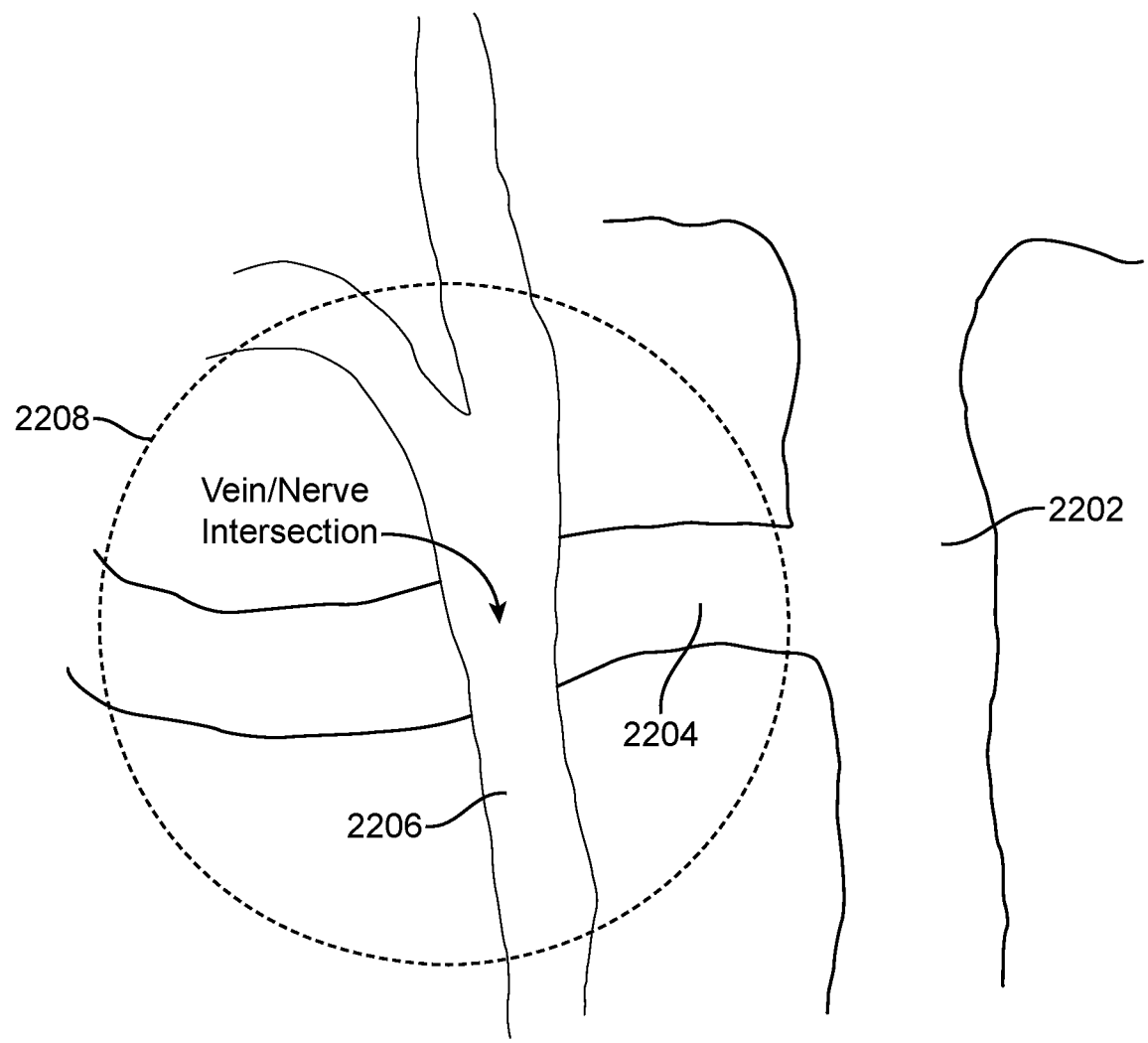
FIG. 22 provides an exemplary depiction of the location of the greater splanchnic nerve relative other identifiers.

In some embodiments, a device is used to access a target nerve (e.g., splanchnic nerve) within the subject. In some embodiments, a device described herein is used. In some embodiments, the device is a catheter-based device. In some embodiments, the device is inserted within a subject 102. In some embodiments, the device is used to access the vascular system (e.g., via femoral and/or subclavian). In some embodiments, the device accesses the vascular system so as to inactivate a sympathetic nerve activity. In some embodiments, the device accesses the vascular system via the Seldinger technique. In some instances, access points for the vascular system in the upper extremity comprise the jugular and/or subclavian veins. In some instances, access points for the vascular system in the lower extremity access comprise the femoral vein. Accordingly, in some embodiments, a device described herein is configured to navigate from either the jugular, subclavian, and/or femoral vein to the superior vena cava. In some embodiments, the device is navigated under fluoroscopic guidance. FIG. 22 provides an exemplary depiction of splanchnic nerve and vein anatomy.

In some embodiments, the device is first navigated within the subject to an approximated location of the target nerve 104. In some embodiments, such approximated location is based on using anatomic landmarks. In some embodiments, the device is guided to the approximated location of the target nerve under fluoroscopy in view of the anatomic landmarks. In some embodiments, the anatomic landmarks comprise radiopaque anatomic landmarks. For example, in some embodiments, the device accesses the azygos vein 2202 (via an access point as described herein), a branch of the superior vena cava. In some embodiments, the device is configured to enter the left and/or right intercostal vein branch 2204. In some embodiments, the device enters the left and/or right intercostal vein branch via an anatomic landmark. In some embodiments, the anatomic landmark comprises the ninth thoracic vertebra (T9) 2208 (depicted as located behind the intersection of the greater splanchnic nerve (GSN) 2206 and left and/or right intercostal vein branch 2204), wherein an exemplary target nerve, the greater splanchnic nerve (GSN) 2206, is located nearby the T9. Accordingly, the location of the GSN can be approximated via the T9. As described herein, in some embodiments, the device is further configured to confirm the location of a target nerve (e.g., the GSN) through direct nerve sensing and/or stimulating the nerve while measuring a physiologic response.

In some embodiments, in addition to or alternative to using anatomic landmarks to approximate the location of a target nerve, a device described herein will use neurosensory to approximate the location of a target nerve. In some embodiments, the device comprises a neurosensory region that is configured to detect action potential signals that will indicate the presence of a nerve nearby (to the device). In some embodiments, as described herein, the neurosensory region comprises one or more neurosensory electrodes.

In some embodiments, a device described herein is configured to stimulate the target nerve so as to elicit a nerve response, such that the location and/or identification of a target nerve may be confirmed 106. In some embodiments, the device comprises a neurostimulation component to stimulate the target nerve. In some embodiments, the device is configured to deliver an electric charge to a subject via the neurostimulation component so as to elicit a nerve response from a target nerve (e.g., GSN). In some embodiments, the neurostimulation component is configured to deliver the charge through one or more neurostimulation electrodes. In some embodiments, the neurostimulation component (e.g., one or more neurostimulation electrodes) is configured to deliver the electric charge within a vessel (e.g., within a vein, artery, or vessel) and/or outside a vessel (e.g., vein). In some embodiments, the device is configured to puncture through a vessel (e.g., vein) and position the one or more neurostimulation electrodes so as to contact the target nerve or place the neurostimulation electrodes in close proximity of the target nerve to deliver the charge. In some embodiments, the device is configured to deliver a charge strong enough to elicit a nerve response, but not strong enough to damage tissue (e.g., target nerve tissue and/or surrounding tissue). In some embodiments, proximity of the device location to the target nerve (e.g., GSN) is confirmed by eliciting one or more sympathetic nerve responses via delivering said electric charge 107. In some embodiments, such sympathetic nerve responses may be detected via a measured physiological response. In some embodiments, examples of detecting a sympathetic response of the GSN via a measured physiological change include detecting adverse changes in pulmonary capillary wedge pressures (PCWP) (e.g., increase in PCWP), gastrointestinal changes including increased motility, changes in less palmer sweating, abnormal changes in temperature for rectal and/or skin measurement, in renal output in relation to changes in vascular dilation, changes in metabolism (i.e. decreased glucose and glucagon release), and/or increases in brain natriuretic peptide. In some embodiments, a device described herein is configured to detect and measure any of such indicators for a sympathetic response. In some embodiments, any of such indicators for a sympathetic response are detected by using medical techniques and/or equipment as known in the art.

For example, in some instances, PCWP is obtained with right heart catheter procedures that are routinely performed in the hospital. An example of such right heart catheter procedure comprises of a percutaneous access of a catheter through the jugular vein (for example, by using the Seldinger technique) in a sterile fashion. In some embodiments, the catheter (for obtaining PCWP) comprises the Swan Ganz catheter, which may have a balloon. In some embodiments, the balloon of the Swan Ganz catheter is inflated, and is threaded through to the superior vena cava, the right atrium, and the right ventricle to the pulmonary outflow tract. In some embodiments, the inflated balloon carries the catheter to a pulmonary artery, where it is wedged, and where pressures detected are called pulmonary capillary wedge pressures. In some instances, the PCWP are considered equivalent to left atrial pressures. In some instances, left atrial pressures are a surrogate measurement for left ventricular end-diastolic pressures. Accordingly, in some instances, PCWP is a measurement of a severity of heart failure, wherein higher PCWP indicates worsened severity of heart failure.

In some embodiments, in addition to or alternate to detecting a physiological response for confirming the location of a target nerve, the neurosensory region can be used to confirm the location of a target nerve via detecting action potentials from the target nerve.

As described herein, in some embodiments, detection for each of the other responses elicited through stimulation of a target nerve will be measured by a device described herein and/or other respective devices and methods known in the art.

In some embodiments, a device described herein (e.g., a catheter device) is configured to sense the presence of a nerve (e.g., target nerve), deliver a charge to provide neurostimulation of the target nerve so as to elicit a sympathetic nerve response therefrom, and/or detect and measure the sympathetic nerve response and/or action potentials by the target nerve. For example, in some embodiments, the device is configured to directly sense the target nerve via a neurosensory region as described herein, which may contain one or more neurosensory electrodes. In some embodiments, the one or more neurosensory electrodes and one or more neurostimulation electrodes (for delivering a charge to the target nerve, as described herein) are separate sets of electrodes. In some embodiments, the one or more neurostimulation electrodes are also be configured to function as neurosensory electrodes. In some embodiments, wherein a device has separate sets of electrodes for neurosensory and neurostimulation, or the same set of electrode for said functions, the device is further configured to change from a neurosensory mode to a neurostimulation mode for stimulating at target nerve. In some embodiments, a method as described herein, comprises placing the device to said neurosensory mode upon being positioned proximate to the GSN (for example, via the T9 landmark) to confirm the presence of a nerve nearby (to the device), In some embodiments, the device is configured to operate in a neurosensory mode and a neurostimulation mode simultaneously. In some embodiments, as described herein, the device, when in the neurosensory mode, uses the electrodes and/or another component to detect action potentials, signifying the presence of a nerve nearby. In some embodiments, a device described herein (e.g., catheter based device) is in operative communication with a computing device. In some embodiments, data from the neurostimulation component and/or the neurosensory component (of the same device) is communicated to the computing device. In some embodiments, the data from the neurostimulation component and/or the neurosensory component is aggregated to indicate that the device is in the position to perform nerve destruction for interrupting nerve activity.

Interruption of Target Nerve Activity

In some embodiments, once the location of the target nerve (e.g., GSN) has been confirmed (e.g., via neurostimulation and/or neurosensory as described herein), nerve activity for the target nerve is then interrupted 108. In some embodiments, such confirmation of the target nerve location comprises, for example, through a physiological response as described herein measuring a response (e.g., sympathetic response) to a stimulated target nerve 107, and/or through detecting action potentials of the target nerve. In some embodiments, confirming the location of a target nerve comprises a combination of neuro-stimulatory and nerve sensing functions evaluated by a software component of a computing device described herein In some embodiments, interrupting nerve activity comprises ablating the target nerve. In some embodiments, a device described herein is configured to ablate a portion of a target nerve (e.g., GSN). In some embodiments, ablation of the target nerve comprises circumferentially lysing a target nerve. As described herein, the device may be configured to ablate a portion of the target nerve using a plurality of different methods. For example, in some embodiments, the device comprises a vascular puncture mechanism to perform the ablation. In some embodiments, the vascular puncture mechanism is actuated in the direction of the nerve to perform the ablation. In some embodiments, the vascular puncture mechanism is also configured to confirm the position of the device using a combination of 1) nerve-sensing, 2) neuro-stimulation with a physiological response, and/or 3) fluoroscopy identifying anatomic landmarks (e.g., the ninth thoracic vertebra (T9), the tenth thoracic vertebra (T10), the eleventh thoracic vertebra (T11), the twelfth thoracic vertebra (T12), or the first lumbar vertebra (L1)). In some embodiments, the device is configured to destroy a portion of the target nerve (portion of the GSN) using one or more of the following modalities: radiofrequency ablation, chemical ablation (carbon dioxide, ethanol, liquid nitrogen), or cryotherapy ablation. In some embodiments, in addition to or alternate to ablating the target nerve, a device described here is configured to down regulate a portion of the target nerve.

As described herein, destroying a portion of the target nerve (e.g., via ablation) corresponds to destroying a portion of the nervous tissue of the target nerve. In some embodiments, such portions of the target nerve(s) (e.g., GSN) being destroyed (e.g., ablated) are able to regenerate. Accordingly, in some embodiments, the length of the portion of the target nerve being destroyed can be specified or predetermined. In some embodiments, the durability of effect for providing relief to a medical condition (e.g., heart failure) is related to the length of the nervous tissue of the target nerve destroyed. In some embodiments, the length of a target nerve (GSN) destruction is a critical factor for providing relief from heart failure symptoms, wherein destroying a longer length of the target nerve (for example via the vascular puncture mechanism, and as compared to intra-vascular ablation) provides for a longer duration of removal of sympathetic activity, and thereby enabling subjects to experience relief from heart failure symptoms for a longer period of time. In some embodiments, the vascular puncture (for example, using a device described herein) is configured to control the direction of the ablation modality. Thus, in some embodiments, the device is configured to target ablation of the target nerve to a specific portion and length of the corresponding nervous tissue. In some embodiments, systems, methods, and devices described herein are configured to minimize collateral damage to other organs when ablating a target nerve. In some embodiments, collateral damage to other organs when ablating a target nerve is enabled through 1) positioning one or more ablation electrodes in close proximity with a target nerve or contacting the target nerve, 2) delivering the ablation energy via a bipolar configuration (thereby helping enable to control the shape and distribution of the ablation energy (e.g., radiofrequency energy), and/or 3) reducing the ablation energy requirements to interrupt nerve activity of the target nerve. In some embodiments, the ablation energy (e.g., radiofrequency energy, microwave energy) delivered to the target nerve is from about 0.1 W to about 100 W. In some embodiments, the temperature provided for ablating the target nerve is from about −200° C. to about 100° C. As described herein, in some embodiments, a needle assembly comprising two needles (e.g. two needle-electrodes) is used to enable a plurality of electrodes to contact or be placed in close proximity to the target nerve at two different locations, so as to enable a length of the target nerve tissue to be ablated.

In some embodiments, the success of a method described herein for treating a medical condition (e.g., heart failure) via nerve interruption is determined by neuro-stimulation and detection of a physiological response (as described herein). In some embodiments, nerve-sensing (e.g., measuring action potential of the target nerve) is also performed in combination or alternate to neuro-stimulation. For example, in some embodiments, once a portion of the target nerve (e.g., GSN) has been destroyed (e.g., via ablation), the device is configured to then provide neurostimulation to confirm a lack of a sympathetic response 110. In some embodiments, as described herein, providing neurostimulation comprises delivering an electrical charge (e.g., via a neurostimulation component) through electrodes strong enough to elicit a nerve response, but not strong enough to damage tissue (nervous tissue or of surrounding tissue). In some embodiments, the presence of a sympathetic response of the GSN will then be monitored, for example via a physiological response, as described herein.

In some embodiments, after a portion of the target nerve has been destroyed (e.g., ablated), physiological parameters are fixed and used as a baseline to detect changes after the target nerve is stimulated (e.g., via a neurostimulation component described herein) as an indication of a sympathetic response. For example, as described herein, in some embodiments, the presence of a sympathetic response comprises detecting adverse changes in pulmonary capillary wedge pressures (PCWP) (e.g., increase in PCWP), gastrointestinal changes including increased motility, changes in less palmer sweating, abnormal changes in temperature for rectal and/or skin measurement, in renal output in relation to changes in vascular dilation, changes in metabolism (i.e. decreased glucose and glucagon release), and/or increases in brain natriuretic peptide. In some embodiments, a nerve-sensing component of the device will detect a lack of nerve activity (e.g., via detecting any action potentials), thereby indicating the nerve has successfully been ablated (for e.g., successfully circumferentially lysed) 112. In some embodiments, detection of decrease PCWP (e.g., via a method described herein) indicates successful ablation as blood is being drawn away from the heart to the abdominal cavity. In some embodiments, detection of a sympathetic response (e.g., a physiological response described herein, or measurement of action-potential from the target nerve) indicates the targeted portion of the target nerve was not successfully destroyed (e.g., ablated), and thus treatment of the medical condition may be considered as incomplete. In some embodiments, where the treatment is determined to be incomplete, the method described herein (e.g., FIG. 1) will be repeated to located and destroy a portion of the target nerve as described herein.

Device

As described herein, in some embodiments, a device described herein is configured for treating a medical condition by interrupting nerve activity for one or more target nerves. In some embodiments, the device is configured to destroy a portion of the nervous tissue for the one or more target nerves (for example, via ablation). In some embodiments, the device is configured to target a specific portion of the target nerve for said destruction. In some embodiments, the device is configured to provide a neurostimulation to the target nerve, sense nerve activity from the target nerve, and/or ablate a portion of a target nerve.

In some embodiments, the device comprises a catheter-based device. In some embodiments, the catheter-based device comprises a device body configured to navigate within a subject. In some embodiments, the device body comprises a radiopaque region (e.g., see reference character 204 in FIG. 2). In some embodiments, the radiopaque region enables for fluoroscopic guidance of the device within a subject. In some embodiments, the device body is in operable communication with a power supply, controller, actuator, and/or computing device for initiating an operation of the device, and/or terminating or pausing operation of the device. In some embodiments, the device is configured to be in operative communication with a power supply via a cord (e.g., a cord plugged into a power supply). In some embodiments, the device is configured to be in operative communication with a controller and/or actuator via a cord (e.g., a cord plugged into a power supply). In some embodiments, the device is configured to be in operative communication with a computing device, power supply, controller, and/or actuator via a wireless component (e.g., Bluetooth®).

In some embodiments, the catheter-based device comprises a vascular puncture mechanism, a mechanism to bias the catheter against the vein walls (within a subject), one or more ablation electrodes, one or more neurostimulation electrodes, a neurosensory region, or a combination thereof. In some embodiments, the vascular puncture mechanism comprises one or more needles or a needle array of varying sizes. In some embodiments, using the vascular puncture mechanism, the device is configured to position the one or more ablation electrodes so as to contact the target nerve or be placed in close proximity to the target nerve. In some embodiments, the device provides neurostimulation to a target nerve using one or more neurostimulation electrodes. In some embodiments, the device is configured to sense activity of a target nerve via the neurosensory region. In some embodiments, the neurosensory region comprises one or more neurosensory electrodes. In some embodiments, the neurosensory region comprises one or more sensors configured to sense nerve activity (such as action potentials). In some embodiments, the device is configured to ablate a portion of a target nerve using one or more ablation electrodes. In some embodiments, the ablation electrode is configured to ablate at least a portion of the target nerve using radiofrequency energy, microwave energy, or a combination thereof. In some embodiments, the device is configured to ablate a portion of a target nerve without an ablation electrode (e.g., chemical ablation, cryoablation, etc.)

In some embodiments, the one or more ablation electrodes, the one or more neurostimulation electrodes, and the one or more neurosensory electrodes are provided as separate electrodes on the device. In some embodiments, the one or more the ablation electrodes, the one or more neurostimulation electrodes, the one or more neurosensory electrodes, or any combination thereof comprise the same electrodes. In some embodiments, the ablation electrode, the neurostimulation electrode, the neurosensory electrode, or any combination thereof comprise the same electrode(s) or different electrode(s) based on the arrangement and/or positioning of the device body within a subject (e.g., catheter tip).

Vessel Puncture Mechanism

In some embodiments, as described herein, the device comprises a vascular puncture mechanism (e.g., vein puncture mechanism) configured to position a needle assembly (e.g., comprising a needle and electrode) so as to contact with or be in close proximity with a target nerve (as described herein). In some embodiments, the vascular puncture mechanism comprises a needle assembly configured to puncture a vein or artery. In some embodiments, the needle assembly comprises one or more needles (e.g., needle-electrode or hollow needle as described herein), configured to puncture a vein or artery. In some embodiments, the needle assembly comprises the ablation electrode, the neurosensory electrode, and/or the neurostimulation electrode. In some embodiments, the one or more ablation electrodes are disposed with the needle assembly. In some embodiments, the needle assembly is configured to extend from a device body of the device towards the target nerve.

In some embodiments, the needle assembly is configured to extend from within a device body of the device (e.g., catheter-based device) and towards the target nerve (e.g., see FIGS. 2-6). In some embodiments, the needle assembly is configured to extend and puncture through a vessel wall (e.g., vein wall). In some embodiments, the needle assembly is configured to extend from the device body via a needle assembly push mechanism that can be actuated and/or moved from a location external to the subject (e.g. accessible by a user outside the subject). In some embodiments, the orientation at which the needle assembly extends through the vessel wall and towards the target nerve is adjustable by adjusting the orientation of the device body within the subject (e.g., rotating the device body). In some embodiments, radiopacity helps enable rotational accuracy for positioning the needle assembly (as described herein). In some embodiments, the radiopaque mark appears different on the catheter body at 90 degree increments, thereby helping direct the needle assembly in the superior/inferior, anterior/posterior, lateral/medial, and/or cranial/caudal directions. In some embodiments, the radiopaque appearance of the radiopaque mark under fluoroscopy changes as the device body rotates, which may help with guiding the device body and positioning the needle assembly. In some embodiments, the location on the device body at which the needle assembly extends and/or the orientation at which the needle assembly extends is correlated with a location of a 1) radiopaque mark, 2) one or more neurostimulation electrodes, and/or a 3) neurosensory region (e.g., neurosensory electrodes, neuro sensor, etc.). In some embodiments, the device body has a longitudinal axis, wherein the needle assembly is configured to extend at a non-zero angle relative to the longitudinal axis.

In some embodiments, the needle assembly extends from a device body of the device in a needle tube that is disposed within a needle lumen within the device body, or located externally thereto. In some embodiments, the needle tube is configured to extend until an end of the needle tube abuts a vessel wall (e.g., vein wall) or is placed in close proximity of the vessel wall. In some embodiments, the needle tube is configured to extend from the device body via a tube push mechanism that can be actuated and/or moved from a location external to the subject (e.g., pushed by a user outside the subject). In some embodiments, the needle assembly is configured to extend through an opening at the end of the tube so as to puncture through the vessel wall. In some embodiments, the needle assembly is configured to extend from the tube via a needle assembly push mechanism that can be actuated and/or moved from a location external to the subject. In some embodiments, the orientation at which the needle assembly extends through the vessel wall and towards the target nerve is adjustable by adjusting the orientation of the device body within the subject (e.g., rotating the device body).

In some embodiments, the device (e.g., catheter based device) is configured to provide a staged stimulation of a target nerve. For example, in some embodiments, wherein the ablation electrodes are the same electrodes as the neurostimulation electrodes, and wherein the needle assembly is located within a needle tube, the device is configured to stimulate the target nerve 1) when the needle tube and needle assembly are disposed within the device body (i.e. prior to being deployed and extending from the device body), and 2) after the needle tube and needle assembly are deployed from the device body, and wherein the needle tube abuts a vessel wall. Accordingly, in some embodiments, the device is configured to further confirm the location of a target nerve via stimulation provided from a closer location (e.g., at the vessel wall), prior to puncture of the vessel. In some embodiments, the stimulation is provided only at the vessel wall (i.e. not a staged stimulation).

In some embodiments, the device body comprises one or more lumens located therein (e.g., needle lumen as described herein). In some embodiments, the needle lumen extends within the device to an opening on the device body. In some embodiments, the opening is a lateral opening on the device body. In some embodiments, the needle lumen extends substantially parallel with a longitudinal axis of the catheter body. In some embodiments, the needle lumen curves so as to terminate at the lateral opening.

In some embodiments, the needle assembly is disposed at least partially on an external portion of the device body. In some embodiments, the needle assembly is configured to be biased to a vessel wall (e.g., a vein wall) by a balloon, thereby enabling the needle assembly to puncture through the vessel wall and extend towards the target nerve (see FIGS. 7-20 for example, as described herein). In some embodiments, an inflatable balloon is located about at least a portion of an external surface of the device body of a device described herein (e.g., catheter based device). In some embodiments, the needle assembly is disposed on the device body such that by inflating (or expanding) the balloon causes the needle assembly to move and be biased towards the vessel wall. In some embodiments, the needle assembly is biased towards the vessel wall, but does not puncture the vessel wall. In some embodiments, the needle assembly is biased towards the vessel wall and punctures through the vessel. In some embodiments, the balloon is inflated or expanded via known methods in the art, such as providing an inflation medium via an inflation tube in fluid communication with the inflatable balloon. In some embodiments, the inflation medium comprises air, another gas, a liquid, a saline solution, other fluids known in the art. In some embodiments, the inflation medium is provided by a source located external to the subject. In some embodiments, the needle assembly is configured to puncture through the vessel wall and extend towards the target nerve via a needle assembly push mechanism that can be actuated and/or moved from a location external to the subject. In some embodiments, the orientation at which the needle assembly extends through the vessel wall and towards the target nerve is adjustable by adjusting the orientation of the device body within the subject (e.g., rotating the device body).

In some embodiments, the device body comprises one or more lumens located therein. In some embodiments, the inflation tube is located within an inflation lumen within the device body. In some embodiments, the inflation lumen extends within the device and enables fluid communication between the inflatable balloon and the inflation tube.

Needle Assembly

Figure 4:
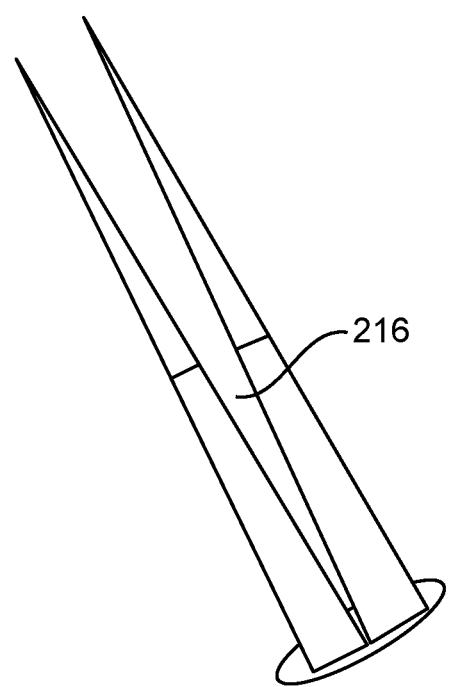
FIG. 4 depicts an exemplary needle assembly of the device according to FIG. 2 after being bifurcated.
Figure 9:
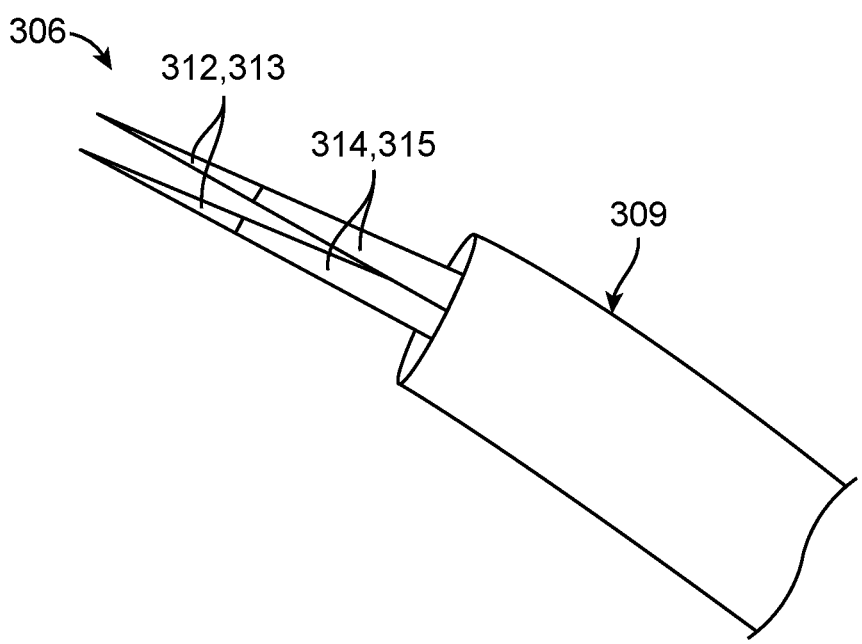
FIG. 9 depicts an exemplary needle assembly of the device according to FIG. 7 after being bifurcated.

In some embodiments, as described herein, the needle assembly for any device (e.g. catheter based device) described herein (including any vascular puncture mechanism) comprises one or more needle-electrodes (e.g., see FIG. 4 and FIG. 9). In some embodiments, each needle-electrode comprises a needle stem and one or more electrodes. In some embodiments, the needle stem and one or more electrodes for each needle-electrode are integrated together as a single component. In some embodiments, the needle stem and one or more electrodes are coupled together for each needle-electrode, which may be a detachable coupling. In some embodiments, the one or more electrodes for each needle-electrode comprises one or more ablation electrodes. In some embodiments, the one or more electrodes for each needle-electrode comprises one or more ablation electrodes, one or more neurostimulation electrodes, and/or one or more neurosensory electrodes. In some embodiments, the one or more electrodes are disposed at any location on each needle-electrode. In some embodiments, at least one electrode is located on a distal end of a needle-electrode, wherein the distal end of the needle-electrode stem is in contact with or in close proximity with the target nerve (e.g., GSN), and wherein a proximal end of the needle-electrode is in contact with, within, and/or in close proximity with a device body of a device. In some embodiments, at least one needle-electrode comprises a single electrode. In some embodiments, at least one needle-electrode comprises a plurality of electrodes. In some embodiments, the plurality of electrodes comprise an electrode array. In some embodiments, the electrode array is arranged in a linear configuration. In some embodiments, the electrode array comprises a plurality of electrodes spaced apart and/or electrically isolated from each other. As described herein, in some embodiments, the plurality of electrodes (e.g., ablation electrodes) are configured to provide ablation energy in a bipolar manner.

In some embodiments, where the needle assembly comprises two or more needle-electrodes, the needle-electrodes are configured to be constrained and/or compressed towards each other in a pre-deployed configuration (e.g., when the needle assembly is located within the device body, within a needle tube, prior to being biased against a vessel wall, prior to puncturing through a vessel wall, or any combination thereof). For example, in some embodiments, the two or more needle-electrodes are configured to be constrained and/or compressed towards each other when navigating with the device body to a desired location near to a target nerve (e.g., GSN). In some embodiments, the two or more needle-electrodes remain constrained and/or compressed towards each other in a pre-deployed configuration (e.g., non-bifurcated configuration as described herein). In some embodiments, the needle assembly is held in a pre-deployed configuration by a needle assembly tube (as described herein), wherein the needle assembly is located therein (e.g., the interior wall of the needle assembly tube constrains the needle assembly from bifurcating). In some embodiments, the two or more needle-electrodes are configured to separate from each other at a distal end as the needle assembly extends a prescribed length from the device body. For example. in some embodiments, a needle assembly comprises two needles that are configured to bifurcate at a distal end of the needle assembly (e.g., see FIGS. 3-4 and FIGS. 8-9), thereby enabling the needle assembly to contact with or be placed in close proximity with the target nerve at two different locations the two bifurcated distal ends of the needle-electrodes. Accordingly, in some embodiments, the needle assembly is configured to target ablation (e.g., via radiofrequency or microwave energy using the needle-electrodes) at two or more locations of a target nerve, and thereby enable a length of the target nerve to be ablated between and/or about said two or more locations. In some embodiments, the ability of needle-electrode bifurcation enables for changing the shape of the thermal zone along the length of the target nerve, resulting in longevity of an intended benefit.

In some embodiments, the distance between the tips of two needles (e.g., needle-electrodes) for a needle-assembly in a bifurcated configuration is identified as a deployed distance. As used herein, in some instances, the term "bifurcated configuration" is used interchangeably with the term "bifurcated position". In some embodiments, the deployed distance is from about 1 mm to about 10 cm. In some embodiments, the distance between the tips of two needles (e.g., needle-electrodes) for a needle-assembly in a non-bifurcated configuration (as described herein) is identified as a non-bifurcated distance. In some embodiments, the deployed distance is larger than the non-bifurcated distance. In some embodiments, the non-bifurcated distance is none (e.g., 0 mm) or substantially none. In some embodiments, as described herein, the device is configured to ablate a length of the target neve that is at least the length of the deployed distance.

As described herein, in some embodiments, the ablation of the target nerve comprises a full circumferential ablation of the target nerve along a given length. In some embodiments, the needle-electrodes are configured to separate (e.g., bifurcate) a prescribed length from each other at a distal end of the needle-assembly. In some embodiments, the needle-electrodes are configured to separate (e.g., bifurcate) from each other in a prescribed orientation, such that the separation (e.g. bifurcation) of the needle-electrodes (e.g., deployed distance) is aligned with a length of the target nerve. For example, in some instances, the target nerve (e.g., GSN) runs perpendicular to a vein described herein, such that the needle-electrodes, when and/or after puncturing through the vein wall, will separate along an axis of the target nerve. In some instances, the target nerve runs parallel with the vein, such that the needle electrodes will separate along the parallel direction of the target nerve. In some embodiments, each needle-electrode of a needle assembly is electrically isolated from each other. In some embodiments, the needle-assembly is configured to deliver energy in a bipolar manner. In some embodiments, for example with respect to a bifurcated needle-assembly, radiofrequency energy is configured to be delivered through both needle-electrodes in a bipolar manner that will be able to destroy a longer length of nerve (for e.g., as compared to ablation from within the vessel).

In some embodiments, the needle assembly comprises three needles, wherein the needle assembly is configured to move from a pre-deployed configuration (as described herein) to a configuration where the tips of the three needles are spaced apart from each other. In some embodiments, the needles are configured to space apart from each other in any direction (e.g., three dimensionally), and thereby be configured to target three locations on a target nerve for ablation.

In some embodiments, the needle assembly comprises one or more needle-electrodes having an electrode array disposed thereon. In some embodiments, the electrode array comprises a plurality of electrodes. In some embodiments, the plurality of electrodes are electrically isolated from each other. In some embodiments, the electrode array is arranged in linear configuration on a same side of a needle-electrode. In some embodiments, the device is configured to introduce a linear electrode array that will travel along the length of the nerve in one direction after vein puncture. The electrode array will create multiple small thermal zones to destroy a long section of the nerve. This allows for greater accuracy and length of nerve destruction. In an exemplary embodiment, a linear electrode array is used from within a vein, artery, or vessel (e.g., the main azygos vein), which may travel in parallel with a target nerve (e.g., the splanchnic nerve), wherein the linear electrode array will be configured to create multiple small thermal zones to destroy a long section of the nerve. This allows for greater accuracy and length of nerve destruction. In some embodiments, the linear electrode array positioned within the target nerve will also be configured to stimulate the target nerve.

In some embodiments, the electrode array is arranged so as to be spaced apart from each other, such that, each electrode is configured to target ablation at a corresponding location on the target nerve (e.g., after the needle-electrode has punctured through a vessel wall). Accordingly, in some embodiments, the needle-electrode is configured to target ablation of a length of a target nerve that corresponds to at least a length of an electrode array disposed on a needle-electrode. In some embodiments, the plurality of electrodes are placed on one side of the needle-electrode to differentially change the thermal map of the ablation zone, so that it is directed specifically at the target nerve.

In some embodiments, each needle-electrode is in operative communication with a power supply (as described herein). In some embodiments, the same power supply is configured to deliver power to each needle electrode. In some embodiments, two or more power supplies are configured to deliver power to a plurality of needle electrodes. In some embodiments, the power supply is located external to the subject. In some embodiments, the power supply comprises a controller to modulate the power delivered to the electrodes on the needle assembly. In some embodiments, the power supply is in operative communication with a controller to modulate the power delivered to the electrodes. In some embodiments, the controller is located on and/or within the device body. In some embodiments, the controller comprises a computing device. In some embodiments, the power supplied to each needle-electrode of a needle assembly is sufficient to ablate a portion of the target nerve. As described herein, in some embodiments, the power supplied to each needle-electrode emits radio radiofrequency energy (for example) that generates heat, which results in ablation of a portion of the target nerve. In some embodiments, the power supply and controller are configured to modulate the power delivered to the device so as to vary the amount of radiofrequency energy delivered by each needle-electrode. In some embodiments, alternate to or in combination with an external power supply, a power supply is provided with the device itself (e.g., batteries located within or about the device body). In some embodiments, wherein a power supply is provided with the device, a user is able to modulate the power delivered to and by each needle-electrode via an externally modulated controller in operative communication with the device.

In some embodiments, the device is configured to deliver a chemical to the target nerve so as to chemically ablate the target nerve. In some embodiments, the device is configured to deliver a controlled amount of a fluid to and/or about the target nerve, so as to interrupt nerve activity of the target nerve. In some embodiments, the fluid comprises a chemical. In some embodiments, the fluid comprises one or more fluids. In some embodiments, the one or more fluids are in gaseous and/or liquid form. In some embodiments, the fluid comprises carbon dioxide, ethanol, liquid nitrogen, a conductive substance (e.g., saline, specialized hydrogel, etc.), an alcohol, lidocaine, lidocaine analogues, or a combination thereof. In some embodiments, the needle assembly comprises one or more hollow needles (e.g., see FIG. 15). In some embodiments, each hollow needle comprises an opening disposed at any location on the hollow needle. In some embodiments, each hollow needle is configured to dispense a fluid (e.g., a chemical) via the opening. In some embodiments, each hollow needle is configured to promote chemical ablation of a portion of a target nerve by dispensing a fluid onto the target nerve and/or about the target nerve. In some embodiments, the fluid to be delivered is stored within the hollow needle prior to deployment of the hollow needle. In some embodiments, each hollow needle is in fluid communication with a fluid source. In some embodiments, each hollow needle is configured to dispense the fluid in a controlled manner so as to chemically ablate a prescribed or minimum portion of the target nerve.

In some embodiments, the device is configured to reduce the temperature of and/or about the target nerve so as to create an ice ball in the target nerve as a function of cryotherapy ablation. In some embodiments, the needle assembly comprises hollow needles, as described herein, to form an ice ball to destroy a portion of the target nerve tissue. In some embodiments, the hollow needle are configured to dispense a cool fluid to the target nerve and/or about the target nerve, thereby enabling a portion of the target nerve to be destroyed.

In some embodiments, the needle-assembly comprising hollow needles is configured to separate at a distal end, as described herein for the needle-electrodes, so as to target chemical ablation and/or cryoablation at specific locations of a target nerve, thereby enabling a longer length of ablation of the target nerve.

In some embodiments, the device is configured to operate other types of ablation modalities (in addition to or alternative to radiofrequency ablation, microwave ablation, chemical ablation, and/or cryoablation), such as ultrasound ablation, and/or alcohol ablation.

Neurostimulation and Neurosensory

In some embodiments, as described herein, the device is configured to stimulate the target nerve, and/or configured to sense activity by the target nerve. In some embodiments, the device comprises one or more neurostimulation electrodes for stimulating the target nerve. In some embodiments, the device comprises a neurosensory region configured for sensing the target nerve. In some embodiments, the one or more neurostimulation electrodes and the one or more neurosensory region is located on the device body of the device. In some embodiments, the neurosensory region, the one or more neurostimulation electrodes, and/or the one or more ablation electrodes are located at any location on a device body of the device (e.g., catheter). In some embodiments, the neurosensory region comprises a sensor for detecting action potentials from a target nerve. In some embodiments, the neurosensory region comprises one or more neurosensory electrodes for detecting action potentials from a target nerve. In some embodiments, the one or more neurosensory electrodes and the one or more neurostimulation electrodes comprise different electrodes. In some embodiments, the one or more neurosensory electrodes and the one or more neurostimulation electrodes share the same electrodes. In some embodiments, the one or more neurostimulation electrodes is configured to provide stimulation to the target nerve in a monopolar manner. In some embodiments, the one or more neurostimulation electrodes is configured to provide stimulation to the target nerve in a bipolar manner.

In some embodiments, as described herein, the device is configured to alternate between a neurosensory mode of operation (e.g., senses action potentials of the target nerve) and a neurostimulation mode of operation (e.g., provides a stimulation to the target nerve). Alternatively or in addition to alternating the modes of operation of the device, in some embodiments, the device is configured to operate in a neurosensory mode and a neurostimulation mode simultaneously.

As described herein, in some embodiments, the neurostimulation mode comprises one or more neurostimulation electrodes configured to stimulate the target nerve to elicit nerve activity (e.g., nerve action potential) and/or physiological changes (e.g., sympathetic nerve response). As described herein, in some embodiments, one or more physiological monitoring devices are provided to measure, sense, and/or detect nerve activity and/or physiological changes (e.g., a sympathetic response) based on stimulation of a target nerve (as described herein). For example, as described herein, in some embodiments, the one or more physiological monitoring devices comprises a Swan Ganz catheter for PCWP measurement. In some embodiments, the one or more physiological monitoring devices is configured to read and interpret the following physiological signals during a method described herein in real time or substantially real time: gastrointestinal changes, palmar sweating, PCWP, temperature for rectal and/or skin measurement, renal output in relation to changes in vascular dilation, metabolism changes, and/or serum brain natriuretic peptide levels. In some embodiments, based on the measured physiological readings, a user (e.g., a physician or other health care personnel) can provide and/or modulate neurostimulation via the device to stimulate the target nerve and thereby induce desired effect (e.g., increase sympathetic activity to the abdominal vascular system). In some embodiments, by causing the following changes, a user (e.g., a physician or other health care personnel) can read and interpret corresponding physiological signals, thereby affirming the device (e.g., catheter-based device) is in the correct location: detecting gastrointestinal changes including decreased motility, detecting changes in increased palmer sweating, detecting increased PCWP, changes in temperature for rectal and/or skin measurement, changes in renal output in relation to changes in vascular dilation, changes in metabolism (e.g., increased glucose and glucagon release), and/or detecting increases in brain natriuretic peptide. In some embodiments, based on a lack of sufficient physiological change as detected via any combination of the said physiological signals, a user may then re-position the device within the subject to again approximate the location of the target nerve, and provide stimulation again to detect for physiological changes.

In some embodiments, the one or more physiological monitoring devices is in operative communication with a computing device and/or display to output the measured physiological readings and/or changes. In some embodiments, at least one physiological monitoring device is integrated with the catheter-based device described herein.

In some embodiments, after the destruction of the nerve has been performed, the device (e.g., catheter based device) is used to stimulate the nerve again (as described herein). In some embodiments, the destroyed portion of the target nerve results in a lack of physiological change when stimulated (e.g., via a neurostimulation component as described herein). In some embodiments, after a portion of the target nerve has been destroyed (e.g., ablated), the following physiological parameters are fixed and used as a baseline to detect changes after the target nerve is provided with a stimulation (e.g., via a neurostimulation component described herein): detecting gastrointestinal changes including increased motility, detecting changes in decreased palmer sweating, detecting decreased PCWP, changes in temperature for rectal and/or skin measurement, changes in renal output in relation to changes in vascular dilation, changes in metabolism, like decreased glucose and glucagon release, and/or detecting decreases in brain natriuretic peptide. In some embodiments, detecting decreased PCWP is an indication of GSN activity interruption, as this suggests blood being drawn away from the heart.

In some embodiments, the one or more neurosensory electrodes are configured to detect action potentials from the target nerve. In some embodiments, the one or more neurosensory electrodes are configured to output the detection of action potentials to a user via an external device, computing device, or other mechanism known in the art.

Power Supply and Control

As described herein, in some embodiments the device described herein (e.g. catheter based device) is in operative communication with a power supply to receive power therefrom. In some embodiments, the power supply (e.g., a generator) is configured to modulate the power delivered to the device. In some embodiments, the power supply is configured to 1) provide neuro-stimulation energy to the neurostimulation electrodes, 2) provide ablation energy to the ablation electrodes, and/or 3) enable the device to detect, read, and/or interpret nerve signals via the neurosensory region (e.g., via a sensor or neurosensory electrodes). In some embodiments, the power supply comprise a controller, and/or is in communication with a controller, configured to modulate the power supplied to the device. In some embodiments, the controller comprises a computing device and/or a display to output information. In some embodiments, a separate power supply and/or controller is configured to provide power to each of the ablation electrodes, the neurostimulation electrodes, and/or the neurosensory region.

In some embodiments, the power supply (e.g., a generator) is configured to provide radiofrequency energy so as to create a thermal ablation zone in the nerve tissue. In some embodiments, said thermal ablation zone is subject to heat generated by the radiofrequency energy provided by, for example, one or more ablation electrodes. In some embodiments, providing radiofrequency energy comprises alternating current (for example, in the range of 350-500 kHz). In some embodiments, the device is configured to destroy at least a portion of a target nerve and vein tissue (for example, via the generator and/or electrodes located on the device that have punctured the vein wall and contact the target nerve or are placed proximate to the target nerve). In some embodiments, the device is configured to provide radiofrequency energy to stimulate a target nerve or group of nerves without damaging the nervous tissue of the target nerve and/or surrounding tissue.

In some embodiments, the device (e.g., catheter based device) and/or power supply (e.g., generator) is configured to modulate the voltage and current output according to a desired power of the ablation energy (e.g., radiofrequency energy, microwave energy) delivered (via the ablation electrodes) to the target nerve. In some embodiments, the power supply is in operative communication with a controller to modulate the voltage and current output. In some embodiments, the device comprises the controller located therein (e.g., within and/or on the device body). In some embodiments, the ablation energy is provided with sufficient voltage and current to generate sufficient heat (that is transferred to the target nerve) to destroy at least a portion of the target nerve. In some embodiments, the power supply is configured to provide power from about 1 W to about 100 W to the device. In some embodiments, at least a portion of the target nerve is destroyed to the full circumference of the target nerve (as described herein). In some embodiments, the device and/or power supply is further configured to modulate a power of ablation energy (e.g., radiofrequency energy, microwave energy) delivered so as to be able to destroy vein tissue and cause vessel sclerosis, such that a device described herein is further configured to reduce, prevent and/or stop bleeding. In some embodiments, such destruction of vein tissue and vessel sclerosis is via the ablation electrodes and/or another set of electrodes.

In some embodiments, the power supply is configured to deliver a charge strong enough for neurostimulation, so as to elicit a nerve response (e.g., via the neurostimulation electrodes), but not strong enough to damage tissue (e.g., target nerve tissue and/or surrounding tissue). In some embodiments, a controller as described herein is configured to modulate the charge delivered by the neurostimulation electrodes.

In some embodiments, the power supply receives power from an external wall unit. Alternatively or additionally, in some embodiments, the power supply (e.g., generator) comprises one or more power sources located therein (e.g., batteries).

FIGS. 2-27B depict exemplary embodiments of a device (e.g., catheter based device) described herein, and for use with a method described herein. In some embodiments, any of such exemplary device embodiments comprise any combination of the features and components described above for a device described herein.

FIGS. 2-6 provide an exemplary depiction of a first embodiment of a device 200 described herein, wherein a needle assembly comprising two needle-electrodes is used to ablate a portion of a target nerve. In some embodiments, with reference to FIG. 2, the device comprises a device body (e.g., catheter body) 210, a catheter tip 202, a needle assembly 206 configured to be disposed within the catheter body, an opening 208 for the needle assembly 206 to extend from, and an electrode region 207 (e.g., for neurostimulation). In some embodiments, the opening 208 is a lateral opening. In some embodiments, the device body 210 has a longitudinal axis (203). In some embodiments, the electrode region is also the same location as a neurosensory region (e.g., for measuring action potentials), as described herein, which can be located anywhere on the catheter body 210. In some embodiments, the electrode region 207 is provided on the catheter body 210. In some embodiments, the device comprises a radiopaque area 204, which may be used to help track the location of the device within a subject. In some embodiments, the radiopaque area is located anywhere on the catheter body. In some embodiments, radiopacity helps enable rotational accuracy for positioning the needle assembly (as described herein). In some embodiments, the radiopaque mark appears different on the catheter body at 90 degree increments, thereby helping direct the needle assembly in the superior/inferior, anterior/posterior, lateral/medial, and/or cranial/caudal directions.

Figure 3:
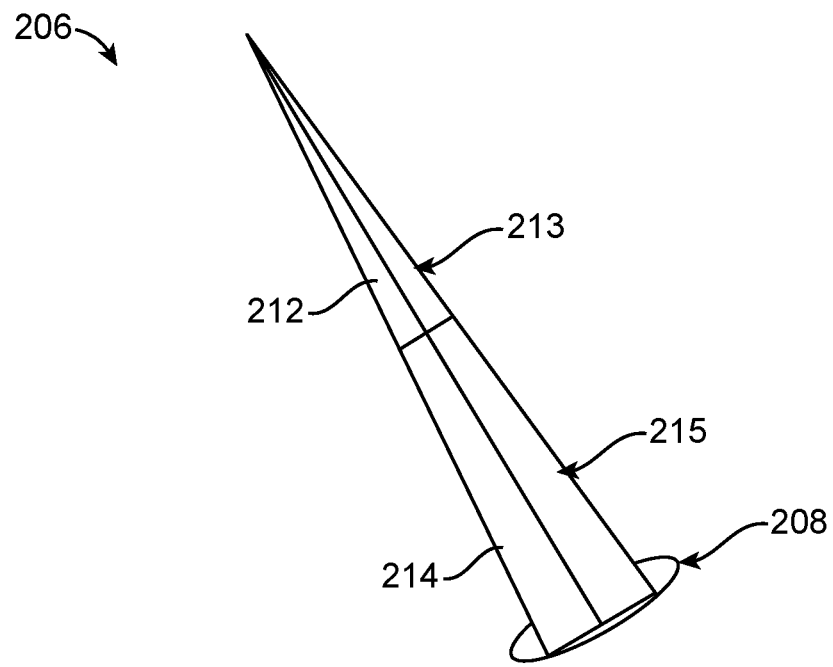
FIG. 3 depicts an exemplary needle assembly of the device according to FIG. 2 prior to being bifurcated.

With reference to FIGS. 3-4, an exemplary depiction of the needle assembly 206 protruding the opening 208 of device 200 is shown (e.g., being deployed). In some embodiments, the device body 210 comprises a needle lumen, which extends within the device body and terminates at the lateral opening 208. In some embodiments, the needle assembly is located within the needle lumen. In some embodiments, the needle assembly comprises two needle-electrodes each comprising a separate needle stem 214, 215. In some embodiments, each needle-electrode comprises a corresponding electrode 212, 213 at the a distal end of the needle assembly. In some embodiments, the electrodes are configured to be located any location on each needle-electrode. As described herein, in some embodiments, each electrode 212, 213 is an ablation electrode configured to) provide radiofrequency energy or microwave energy to ablate at least a portion of a target nerve. In some embodiments, the electrodes 212, 213 are configured to act as a neurostimulation electrode and/or a neurosensory electrode. In some embodiments, the needle assembly 206 is placed within the catheter body in a compressed configuration, such that the needle stems 214, 215 and, in some instances, electrodes 212, 213, are pressed together. In some embodiments, the needle assembly 206 is configured to bifurcate upon exiting the opening 208, wherein the electrodes 212, 213 and at least a portion of the needle stems 214, 215 of the corresponding needle-electrodes are configured to separate from each other once extending out of the opening 208 (e.g., separate in a "V" shape). In some embodiments, the needle assembly comprises shape memory so as to be configured to bifurcate once exiting the opening 208 into an open space. In some embodiments, the needle assembly 206 is configured to bifurcate based on an actuated mechanism. In some embodiments, the actuated mechanism comprises an automated and/or manual actuation (e.g., actuation by a user). In some embodiments, the needle assembly 206 will bifurcate along or approximate a length of a target nerve, thereby enabling each electrode 212, 213 to contact or be placed proximate to two different locations on the target nerve.

As described herein, in some embodiments, a needle assembly push stem (or other structure) is provided within the catheter body 210 and configured to engage with the needle assembly so as to push the needle assembly 206 through the opening 208. In some embodiments, the push stem is located within the catheter body 210 and configured to be actuated so as to automatically push the needle assembly 206 out of the opening 208. In some embodiments, automatic actuation of the push stem is initiated by a wireless or wired signal provided by the user. In some embodiments, the push stem is configured to be manually pushed out by a user (via a mechanism that extends from the device to outside the subject). In some embodiments, the needle assembly, e.g., electrodes 212, 213, are configured to extend a prescribed distance out of the opening so as to puncture through a vein wall and contact or be located proximate to a target nerve (e.g. GSN, as described herein).

In some embodiments, as described herein, the needle assembly 206 is provided within a needle assembly tube (not shown) located within the catheter body 210. In some embodiments, the tube is configured to extend from the opening 208 to the vein wall, wherein the needle assembly is then configured to be extend from an end of the tube and puncture through the vein wall. In some embodiments, the needle assembly tube is similar to the tube depicted in FIGS. 7-11 with reference character 309.

In some embodiments, the catheter body 210 is configured to rotate so as to orient the needle assembly in a prescribed direction relative to the target nerve. In some embodiments, the needle assembly is configured to extend from the catheter body according to a specific configuration, which corresponds to the location of a radiopacity marker (e.g., 204), such that the direction and position of the electrodes on the needle assembly when extended can be correlated with the location of the radiopacity marker.

Figure 5:
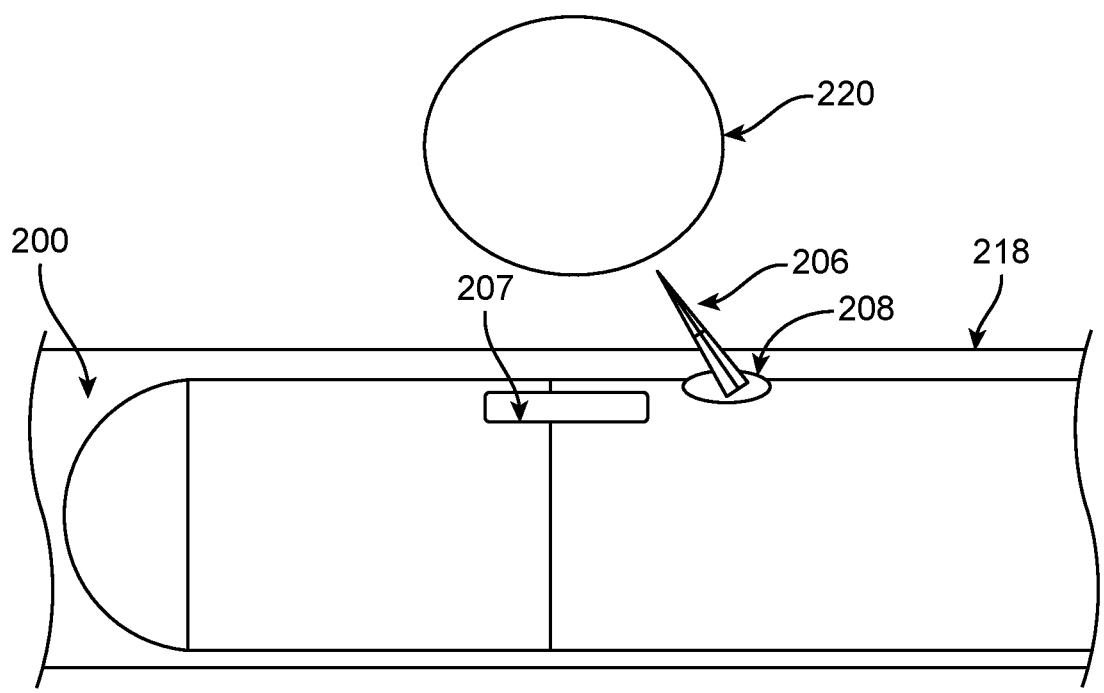
FIG. 5 depicts an exemplary embodiment of the device according to FIG. 2 with the needle assembly extending towards a target nerve.
Figure 6:
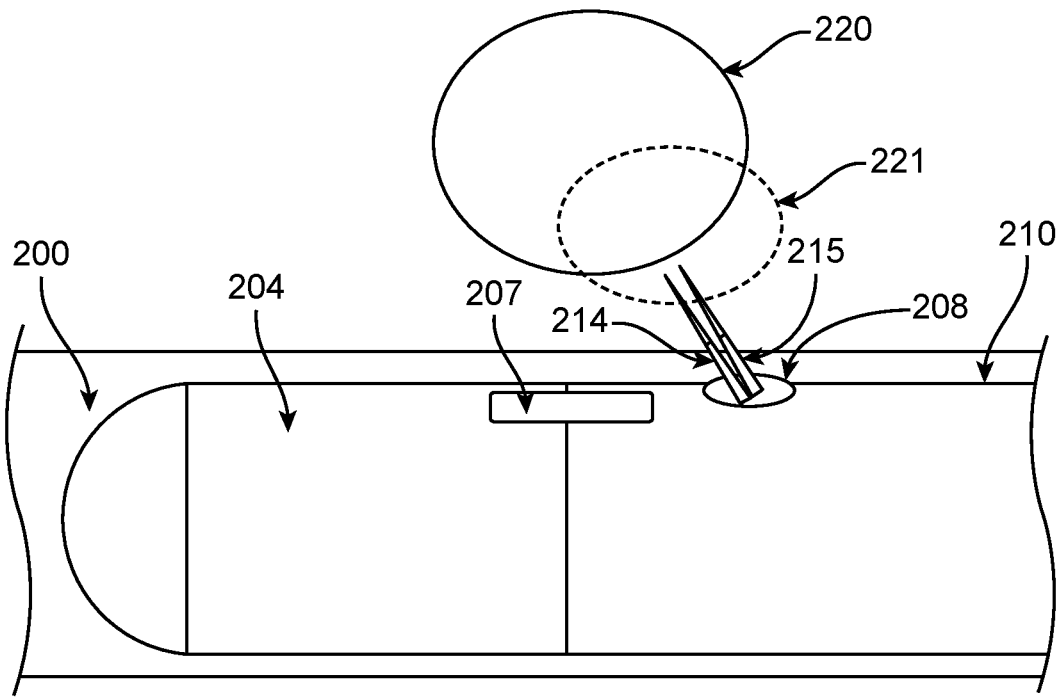
FIG. 6 depicts an exemplary embodiment of the device according to FIG. 2 with the needle assembly extending towards a target nerve in a bifurcated configuration.
Figure 7:
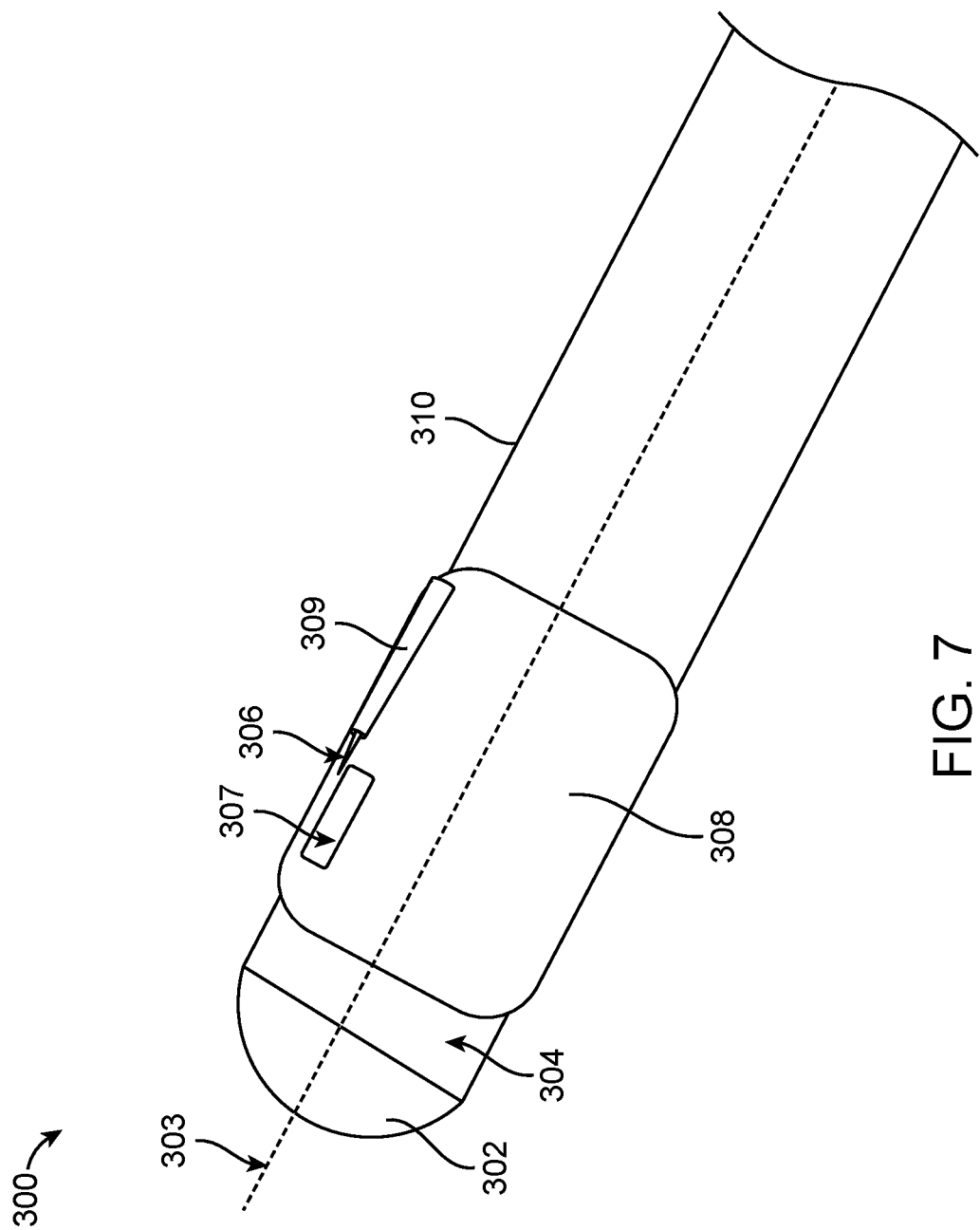
FIG. 7 depicts an exemplary second embodiment of a device used for treating a medical condition as described herein.

FIGS. 5-6 depict an exemplary depiction of the device 200 located within a vein, artery, or vessel 218 (e.g., left and/or right intercostal vein branch 2204 from FIG. 22), wherein the needle assembly 206 is extending from the opening 208 and contacting a target nerve (e.g., GSN) in a bifurcated configuration at two different locations located between two portions of the target nerve 220, 221 (see FIG. 6). As described herein, in some embodiments, the needle assembly 206 will bifurcate along a length of a target nerve. As described herein, the catheter body 210 is configured to be rotatable, so as to position the bifurcated needle stems 214, 215 along a length of a target nerve. In some embodiments, the needle assembly extends in a non-zero angle relative to the longitudinal axis 203. In FIG. 6, for example, wherein the catheter body 210 is characterized as being positioned along an x-axis, the needle stems 214, 215 are bifurcated along a z-axis, corresponding to a length of the target nerve between the two locations 220, 221. Accordingly, the electrodes 212, 213 are configured to ablate (e.g., circumferentially lyse) a length of the target nerve that is at least the length from target nerve location 220 to target nerve location 221. In some embodiments, the target nerve circumference 220, 221 represents the ablation area (at a given location), wherein the portion of the target nerve between portions 220, 221 represents the length of the ablation area. In some embodiments, as described herein, the longer the length of the ablation area provides for a longer treatment period for a medical condition described herein (e.g., heart failure).

In some embodiments, the electrode region area 207 is configured to provide a stimulation to the target nerve (via for example, neurostimulation electrodes described herein). In some embodiments, the electrode region is positioned within the subject (for e.g., via radiopacity markers and/or a neurosensory region) at a location that corresponds to the target nerve (e.g., location may be such that where neurostimulation is provided to the target nerve in a perpendicular direction to an axis of the catheter body 210). Accordingly, in some embodiments, stimulation is provided via signals delivered perpendicularly. In some embodiments, the configuration of the needle assembly extending from the catheter body correlates with a positioning of the electrode region 207.

FIGS. 7-13 provide an exemplary depiction of a second embodiment of a device 300 described herein, wherein a needle assembly comprising two needle-electrodes is used with a balloon to ablate a target nerve. In some embodiments, the balloon is configured to be inflated. In some embodiments, with reference to FIG. 7, the device comprises a device body (e.g., catheter body) 310, a catheter tip 302, a needle assembly 306 configured to be disposed with a balloon 308 located about the catheter body 310, and an electrode region 307 (e.g., for neurostimulation). In some embodiments, the device body 310 has a longitudinal axis (303). In some embodiments, the electrode region is also the same location as a neuro sensory region, as described herein, which can be located anywhere on the catheter body 310. In some embodiments, the electrode region 307 is disposed on the balloon 308. In some embodiments, the device 300 further comprises a needle assembly tube 309, within which at least a portion of the needle assembly 306 is configured to be located and further configured to extend from. In some embodiments, the needle assembly tube 309 is embedded with the balloon 308 and protrudes therefrom. In some embodiments, the device 300 does not comprise a needle assembly tube, and instead the needle assembly 306 is located on the balloon 308, at least partially located within the balloon, or a combination thereof. In some embodiments, the needle assembly tube is at least partially located within the device body 310. In some embodiments, the device comprises a radiopaque area 304, which may be used to help track the location of the device within a subject. In some embodiments, the radiopaque area is located anywhere on the catheter body. In some embodiments, radiopacity helps enable rotational accuracy for positioning the needle assembly (as described herein). In some embodiments, the radiopaque mark appears different on the catheter body at 90 degree increments, thereby helping direct the needle assembly in the superior/inferior anterior/posterior, lateral/medial, and/or cranial/caudal directions.

Figure 8:
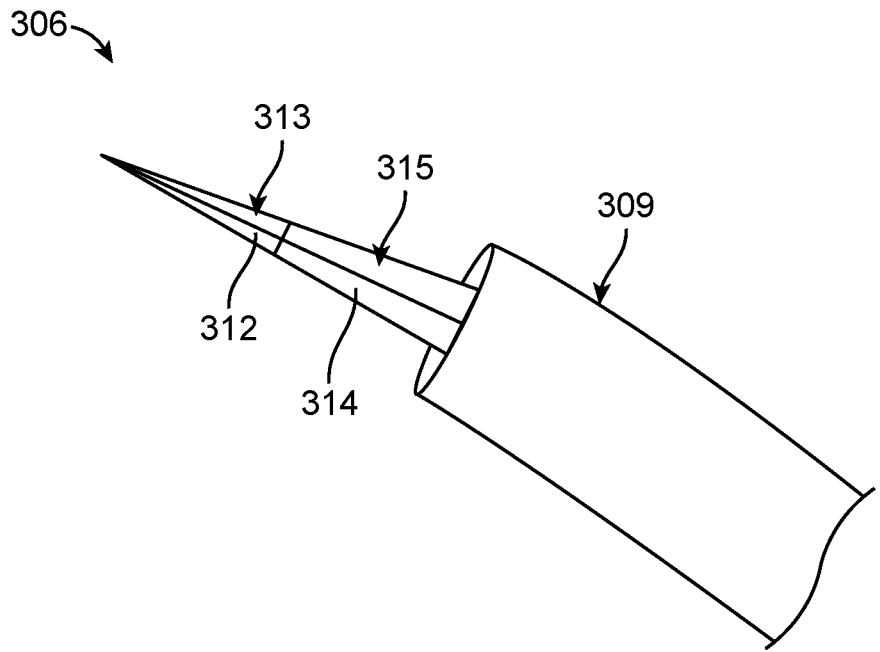
FIG. 8 depicts an exemplary needle assembly of the device according to FIG. 7 prior to being bifurcated.

With reference to FIGS. 8-9, an exemplary depiction of the needle assembly 306 of the device 300 is shown. In some embodiments, the needle assembly 306 comprises two separate needle-electrodes, each comprising a needle stem 314, 315. In some embodiments, each needle-electrode comprises a corresponding electrode 312, 313 at a distal end of the needle assembly. In some embodiments, the electrodes are configured to be located any location on each needle-electrode. As described herein, in some embodiments, each electrode 312, 313 is an ablation electrode configured to) provide radiofrequency energy to ablate at least a portion of a target nerve. In some embodiments, the electrodes 312, 313 are configured to act as a neurostimulation electrode and/or a neurosensory electrode. In some embodiments, at least a portion of the needle assembly 306 is located within the needle assembly lumen 309 when the device is being advanced to a desired location within the subject. In some embodiments, the needle assembly 306 is configured to extend from the needle assembly tube 309. In some embodiments, the needle assembly 306 is configured to be provided in a compressed configuration, such that the needle stems 314, 315 and, in some instances, electrodes 312, 313, are pressed together. In some embodiments, the needle assembly 306 is configured to bifurcate upon extending from the needle assembly lumen 309, wherein the electrodes 312, 313 and at least a portion of the needle stems 314, 315 of the needle-electrodes are configured to separate from each other (e.g., the needle assembly comprises a "v-shaped" configuration). In some embodiments, the needle assembly 306 comprises shape memory so as to be configured bifurcate once extending a predetermined length from the needle assembly tube 309. In some embodiments, the needle assembly 306 is configured to bifurcate based on an actuated mechanism. In some embodiments, the actuated mechanism comprises an automated and/or manual actuation (e.g., actuation by a user). In some embodiments, the actuated mechanism comprises an automated and/or manual actuation. In some embodiments, the needle assembly 306 will bifurcate along a length of a target nerve, thereby enabling each electrode 312, 313 to contact or be placed proximate to two different locations on the target nerve.

Figure 10:
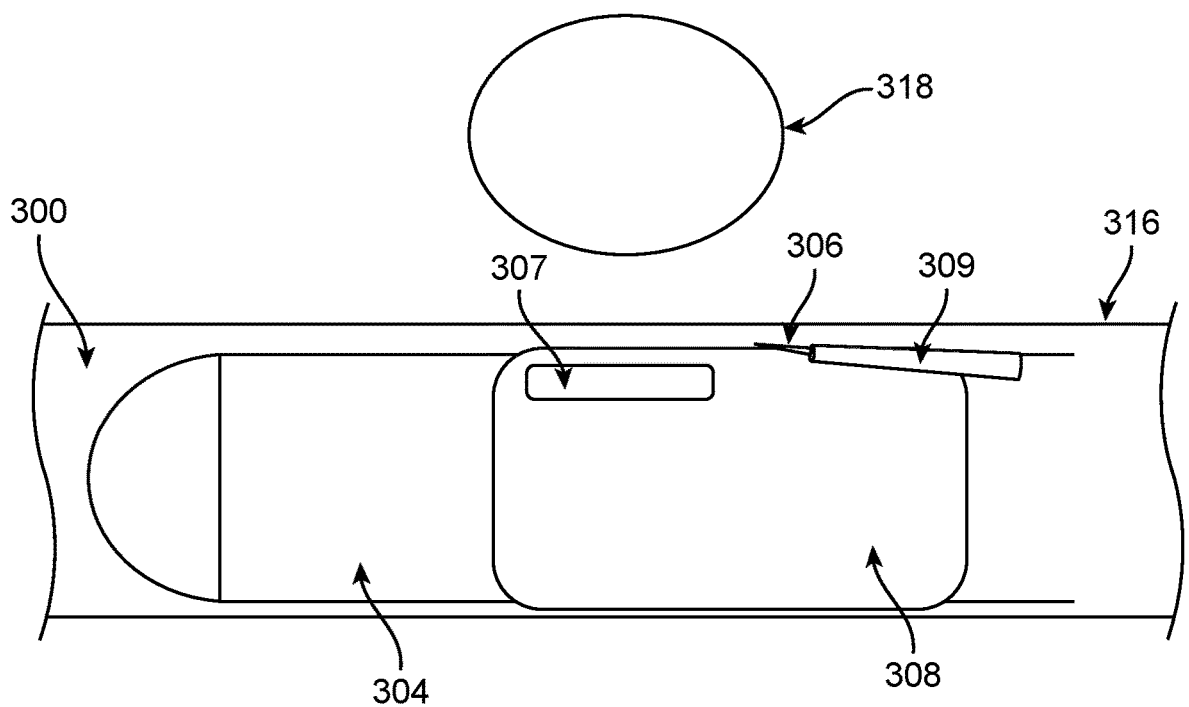
FIG. 10 depicts an exemplary embodiment of the device according to FIG. 7 prior to inflation of a balloon.
Figure 11:
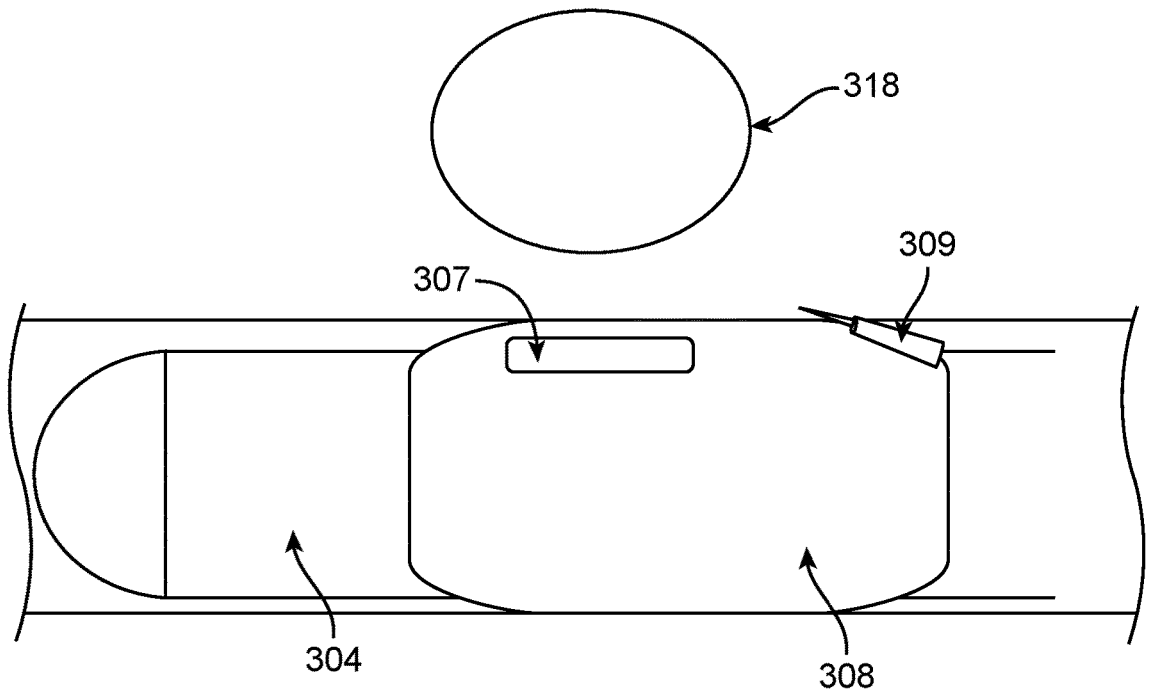
FIG. 11 depicts an exemplary embodiment of the device according to FIG. 7 are inflation of a balloon.

FIGS. 10-11 depict an exemplary depiction of the device 300 located within a vein, artery, or vessel 316 (e.g., left and/or right intercostal vein branch 2204 from FIG. 22) and proximate to the location of a target nerve 318. FIG. 10 depicts the balloon 308 in a deflated configuration and prior to deployment of the needle assembly 306, while FIG. 11 depicts the balloon 308 in an inflated configuration. In some embodiments, the needle assembly 306 is positioned, such that, inflating the balloon 308 pushes out the needle assembly tube 309, thereby enabling the needle assembly 306 to puncture through the vein 316 wall (see FIG. 11). In some embodiments, inflating the balloon 308 biases needle assembly tube 309 against the vessel wall, such that the needle assembly 306 is configured to puncture through the vessel wall when extending from the needle assembly tube. In some embodiments, inflating the balloon 308 biases needle assembly tube 309 against the vessel wall, but wherein the needle assembly 306 does not yet puncture the vessel wall unless extending from the needle assembly tube. In an alternate embodiment, the needle assembly is configured to bias against the vessel wall through a means other than an inflatable balloon (as known in the art).

In some embodiments, the balloon 308 is in fluid communication with an inflation medium that enables the balloon to be inflated. In some embodiments, the device body 310 comprises an inflation tube that extends therein, and that is fluid communication with an inflation medium source. In some embodiments, inflation medium comprises a fluid, such as a gas (e.g., air, etc.), and/or a liquid (e.g., water, saline, etc). In some embodiments, the inflation medium source is located outside the subject. In some embodiments, the device comprises a stored supply of the inflation medium for inflating the balloon 308. In some embodiments, the inflation medium is supplied via an automatic controller. In some embodiments, the inflation medium is supplied via manual input.

Figure 12:
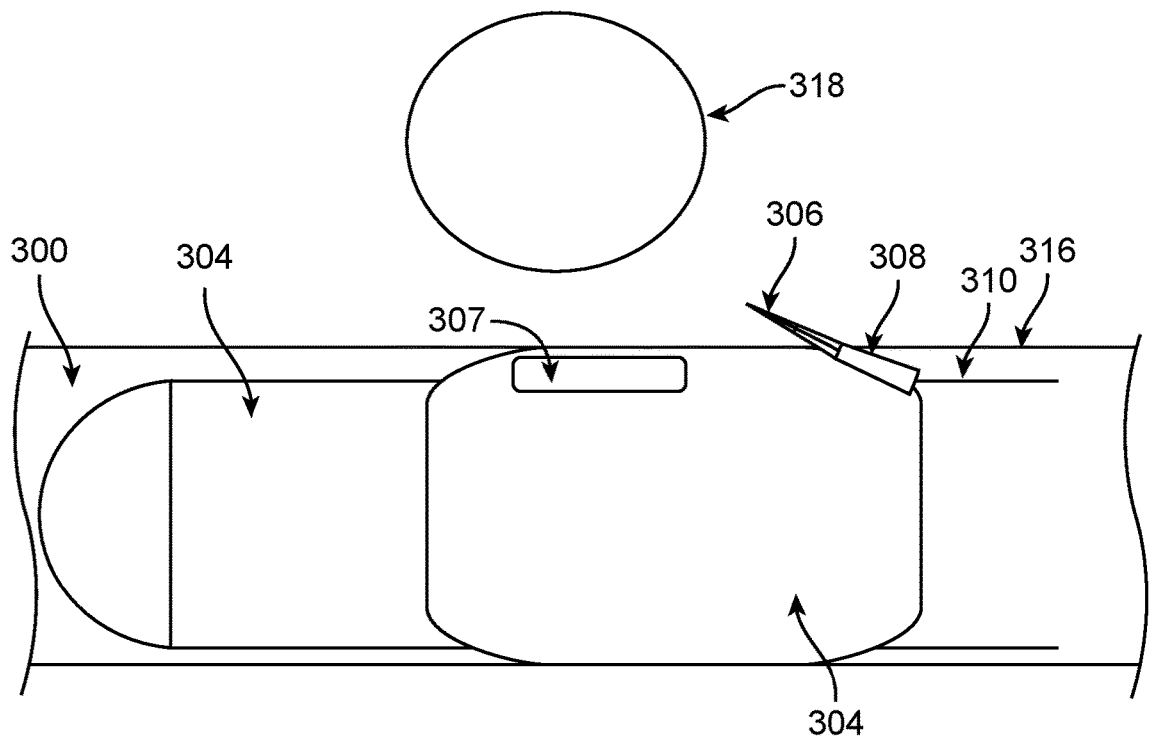
FIG. 12 depicts an exemplary embodiment of the device according to FIG. 7 with a needle assembly that has punctured through a vein wall.
Figure 13:
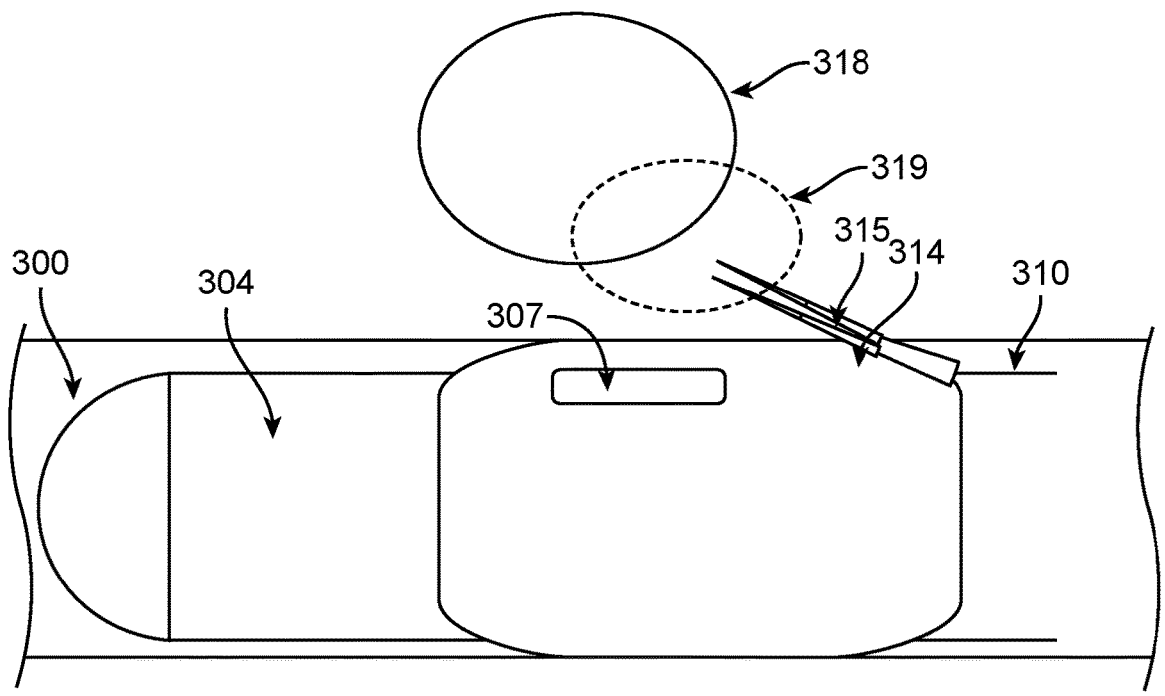
FIG. 13 depicts an exemplary embodiment of the device according to FIG. 7 with a bifurcated needle assembly extending towards a target nerve.
Figure 14:
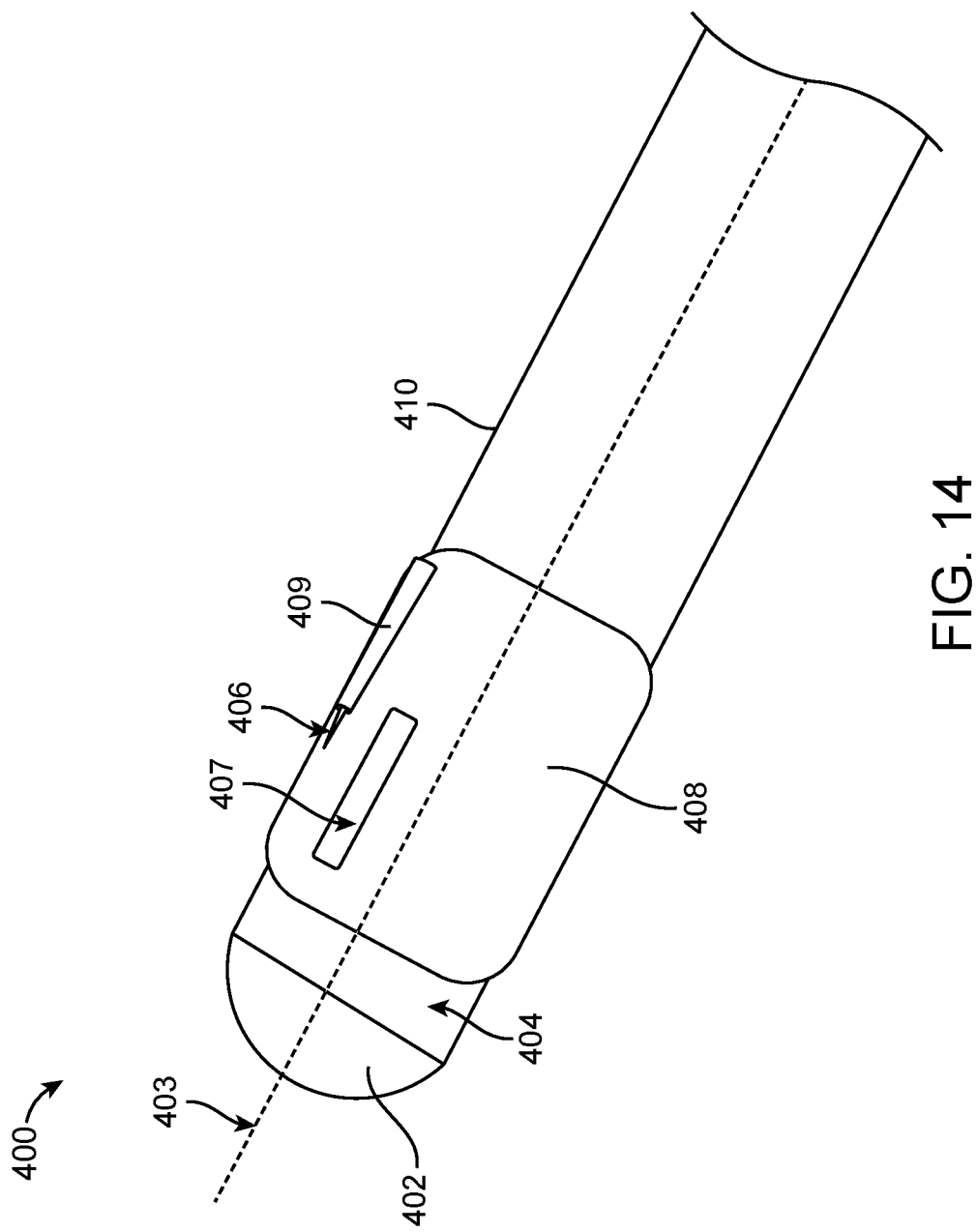
FIG. 14 depicts an exemplary third embodiment of a device used for treating a medical condition as described herein.

FIGS. 12-13 depict an exemplary embodiment of the needle assembly 306 extending towards the target nerve 318. In some embodiments, inflation of the balloon enables the needle assembly 306 to extend towards the target nerve. As described herein, in some embodiments, a needle assembly push stem (or other structure) is provided within the catheter body 310 and configured to engage and push the needle assembly 306 through the vessel wall and/or towards the target nerve. In some embodiments, the push stem is located within the catheter body 310 and configured to be actuated so as to automatically push the needle assembly 306. In some embodiments, automatic actuation of the push stem is initiated by a wireless or wired signal provided by the user. In some embodiments, the push stem is configured to be manually pushed out by a user (via a mechanism that extends from the device to outside the subject). In some embodiments, the needle assembly 306, e.g., the electrodes 312, 313, are configured to extend a prescribed distance from the needle assembly lumen 309, so as to contact or be located proximate to a target nerve 318 (e.g. GSN, as described herein).

In some embodiments, the catheter body 310 is configured to rotate so as to orient the needle assembly 306 in a prescribed direction relative to the target nerve. In some embodiments, the needle assembly is configured to extend from the catheter body according to a specific configuration, which corresponds to the location of a radiopacity marker (e.g., 304), such that the direction and position of the electrodes on the needle assembly when extended can be correlated with the location of the radiopacity marker.

FIG. 13 depicts an exemplary depiction of the needle assembly 306 extending and contacting a target nerve (e.g., GSN) in a bifurcated configuration at two different locations located between two portions of the target nerve 318, 319. As described herein, in some embodiments, the needle assembly 306 will bifurcate along a length of a target nerve. In some embodiments, the needle assembly 306 extends in a non-zero angle relative to the longitudinal axis 303. As described herein, the needle assembly 306 is configured to be rotatable about a needle assembly axis, so as to position the bifurcated needle stems 314, 315 of the needle-electrodes along a length of a target nerve. In FIG. 13, for example, wherein the catheter body 310 is characterized as being positioned along an x-axis, the needle stems 314, 315 are bifurcated along a z-axis, corresponding to a length of the target nerve between the two locations 318, 319. Accordingly, the electrodes 312, 313 are configured to ablate (e.g., circumferentially lyse) a length of the target nerve that is at least the length from target nerve location 318 to target nerve location 319. In some embodiments, the target nerve circumference 318, 319 represents the ablation area, at a given location, wherein the portion of the target nerve between portions 318, 319 represents the length of the ablation area. In some embodiments, as described herein, the longer the length of the ablation area provides for a longer treatment period for a medical condition described herein (e.g., heart failure).

In some embodiments, the electrode region area 307 is configured to provide a stimulation to the target nerve (via for example, neurostimulation electrodes described herein). In some embodiments, the electrode region is positioned within the subject (for e.g., using radiopacity markers and/or a neurosensory region) at a location that corresponds to the target nerve (e.g., location may be such that where neurostimulation is provided to the target nerve in a perpendicular direction an axis of the catheter body 310). Accordingly, in some embodiments, stimulation is provided via signals delivered perpendicularly. In some embodiments, the configuration of the needle assembly extending from the catheter body correlates with a positioning of the electrode region 307.

FIGS. 14-17 provide an exemplary depiction of a third embodiment of a device 400 described herein, wherein the device is configured to chemically ablate a target nerve. In some embodiments, with reference to FIG. 14, the device comprises a device body (catheter body) 410, a catheter tip 402, a needle assembly 406 configured to be disposed with an expandable balloon 408 located about the catheter body 410, and an electrode region 407 (e.g., for neurostimulation). In some embodiments, the device body 410 has a longitudinal axis (403). In some embodiments, the electrode region is also the same location as a neuro sensory region, as described herein, which can be located anywhere on the catheter body 410. In some embodiments, the electrode region 407 is disposed on the expandable balloon 408. In some embodiments, the device 400 further comprises a needle assembly tube 409, within which at least a portion of the needle assembly 406 is configured to be located and further configured to extend from. In some embodiments, the needle assembly tube 409 is embedded with the expandable balloon 408 and protrudes therefrom. In some embodiments, the device comprises a radiopaque area 404, which may be used to help track the location of the device within a subject. In some embodiments, the radiopaque area is located anywhere on the catheter body. In some embodiments, radiopacity helps enable rotational accuracy for positioning the needle assembly (as described herein). In some embodiments, the radiopaque mark appears different on the catheter body at 90 degree increments, thereby helping direct the needle assembly in the superior/inferior, anterior/posterior, lateral/medial, and/or cranial/caudal directions.

Figure 15:
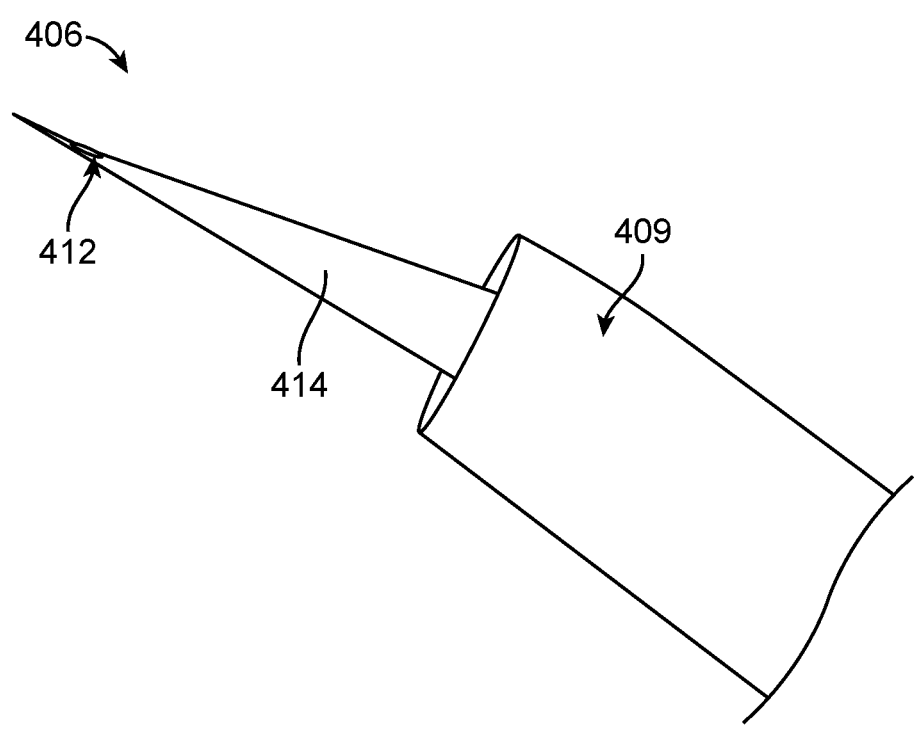
FIG. 15 depicts an exemplary needle assembly of the device according to FIG. 14.

With reference to FIG. 15, an exemplary depiction of the needle assembly 406 of the device 400 is shown. In some embodiments, the needle assembly comprises a needle stem 414 and a needle port 412. In some embodiments, the needle stem is hollow. In some embodiments, the device is configured to dispense a chemical through the needle port 412. In some embodiments, the chemical is configured to ablate the target nerve. In some embodiments, the device is configured to dispense the chemical with a controlled distribution so as to achieve a desired ablation length of the target nerve. In some embodiments, at least a portion of the needle assembly 406 is located within the needle assembly lumen 409 when the device is being advanced to a desired location within the subject. In some embodiments, the needle assembly 406 is configured to extend from the needle assembly lumen 409.

Figure 16:
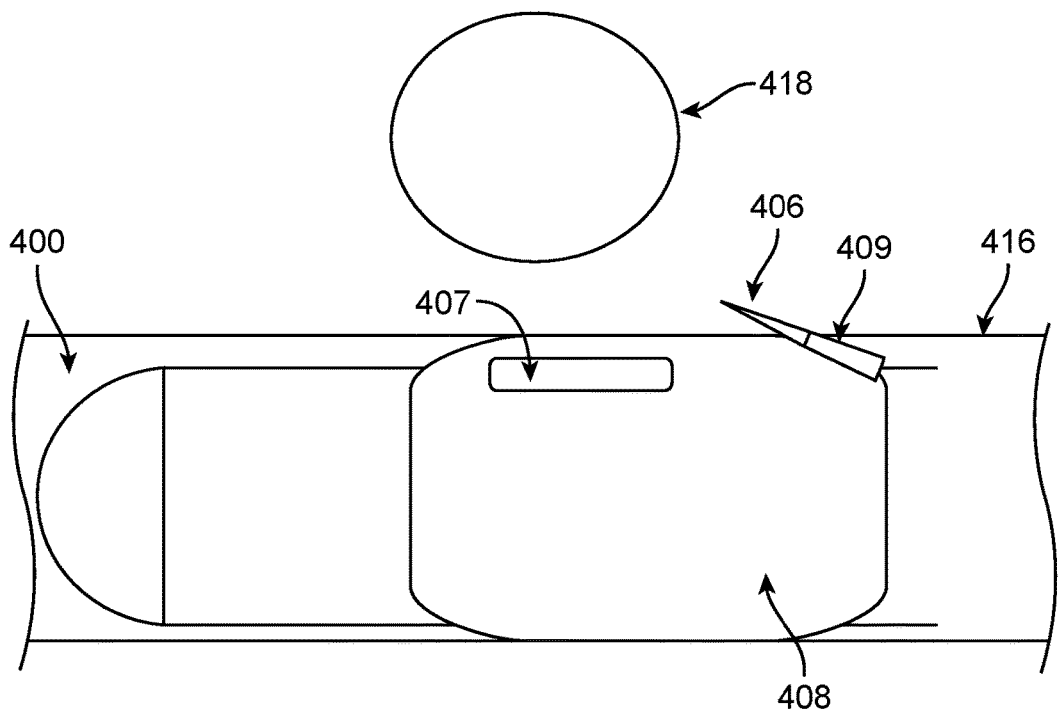
FIG. 16 depicts an exemplary embodiment of the device according to FIG. 14 with a needle assembly that has punctured through a vein wall.
Figure 17:
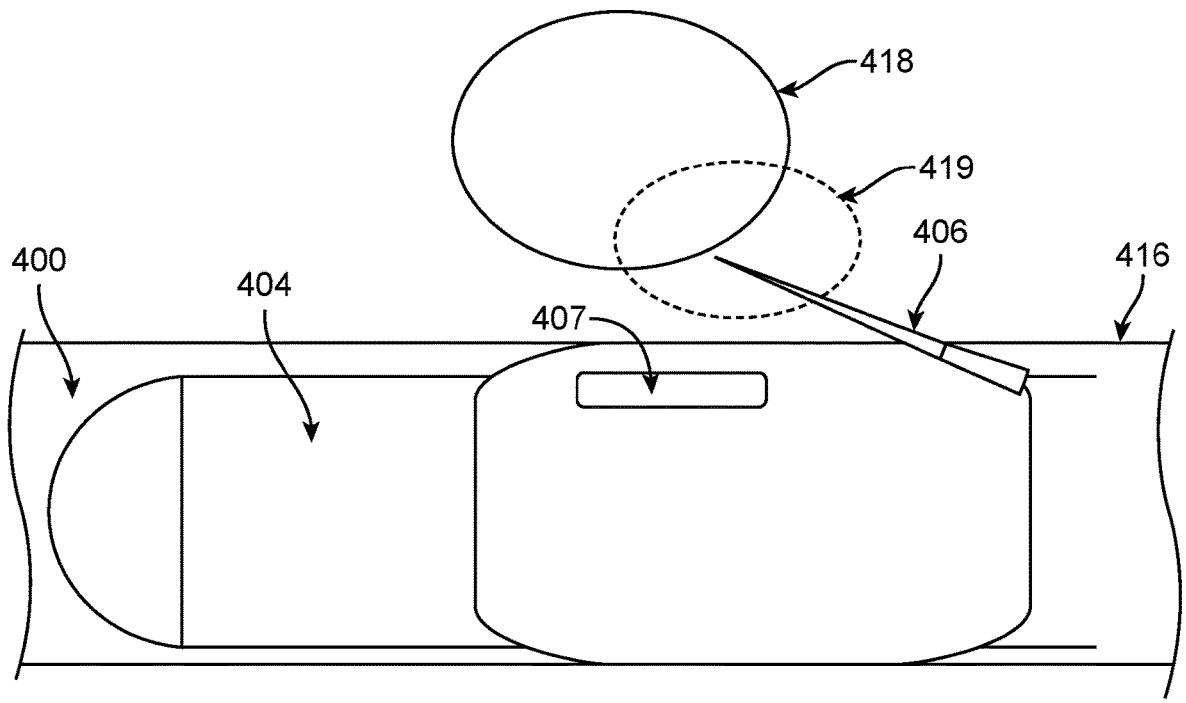
FIG. 17 depicts an exemplary embodiment of the device according to FIG. 14 with a needle assembly extending towards a target nerve.
Figure 18:
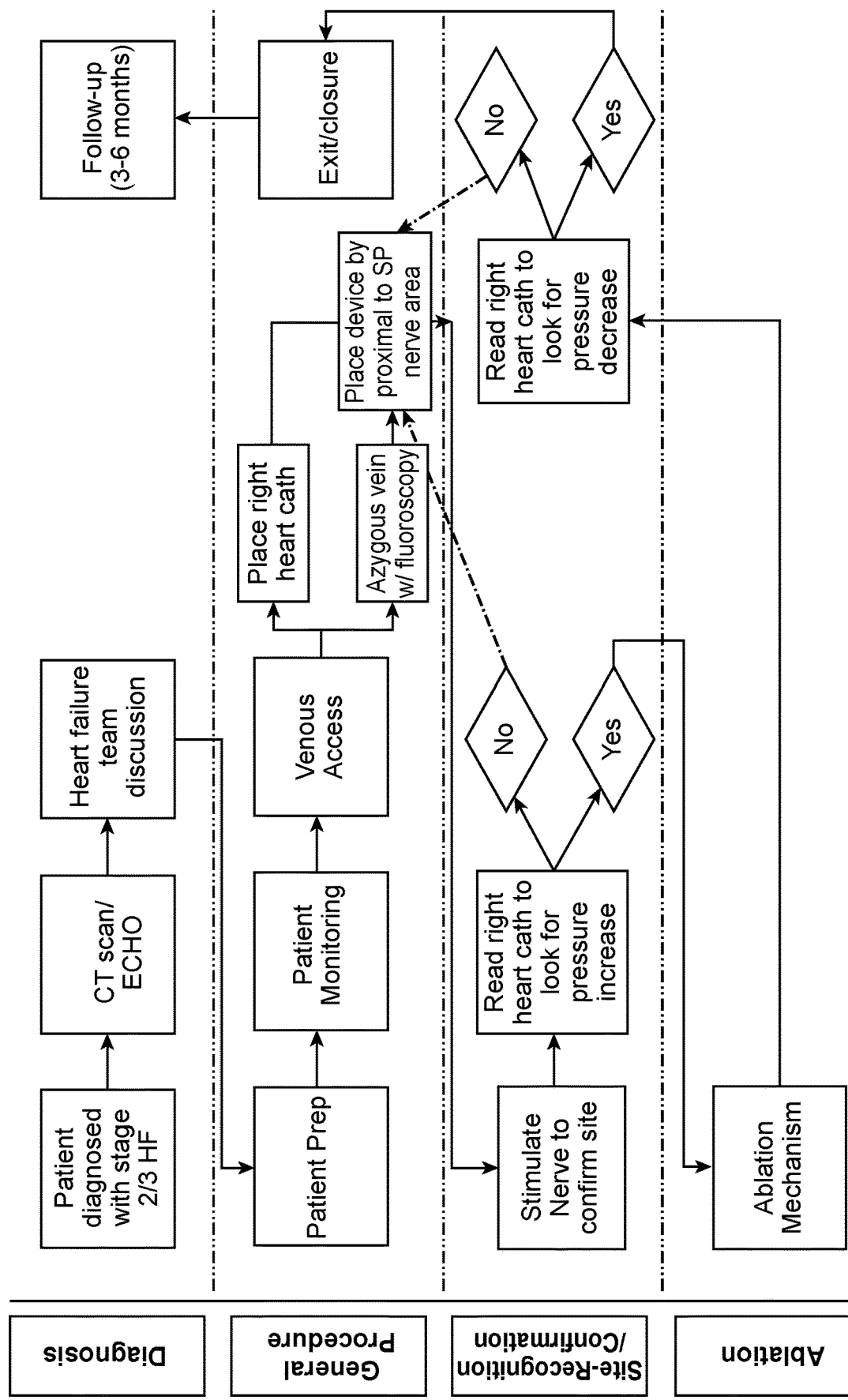
FIG. 18 depicts an exemplary fourth embodiment of a device used for treating a medical condition as described herein.

FIGS. 16-17 depict an exemplary depiction of the device 400 located within a vein, artery, or vessel 416 (e.g., left and/or right intercostal vein branch 2204 from FIG. 22) and proximate to the location of a target nerve 418. FIG. 16 provides an exemplary depiction of the expandable balloon 408 in an expanded configuration, wherein the needle assembly tube 409 is biased towards the vein wall 416, such that the needle assembly 406 punctures through the vein wall 416. In some embodiments, expanding the expandable balloon 408 biases needle assembly tube 409 against the vessel wall, such that the needle assembly 406 is configured to puncture through the vessel wall when extending from the needle assembly tube. In some embodiments, the expandable balloon 408 is in operative communication with a mechanism configured to supply a gas (e.g., air) to the expandable balloon, thereby causing it to expand. In some embodiments, the gas is supplied via a supply line connecting a gas source (e.g., outside the subject) to the device. In some embodiments, the device comprises a stored supply of the gas for expanding the expandable balloon 408. In some embodiments, the gas is supplied via an automatic controller. In some embodiments, the gas is supplied via manual input.

FIG. 17 depicts an exemplary embodiment of the needle assembly 406 extending towards the target nerve 418. In some embodiments, expansion of the balloon 408 enables the needle assembly 406 to extend towards the target nerve. As described herein, in some embodiments, a needle assembly push stem (or other structure) is provided within the catheter body 410 and configured to engage and push the needle assembly 406 towards the target nerve. In some embodiments, the push stem is located within the catheter body 410 and configured to be actuated so as to automatically push the needle assembly 406. In some embodiments, automatic actuation of the push stem is initiated by a wireless or wired signal provided by the user. In some embodiments, the push stem is configured to be manually pushed out by a user (via a mechanism that extends from the device to outside the subject). In some embodiments, the needle assembly 406, e.g., needle port 412, is configured to extend a prescribed distance from the needle assembly lumen 409, so as to contact or be located proximate to a target nerve 418 (e.g. GSN, as described herein). In some embodiments, the needle assembly is configured to extend in a non-zero angle relative to the longitudinal axis 403. In some embodiments, the needle assembly 406 is configured to rotate about a needle assembly axis. In some embodiments, the needle assembly is configured to be rotated by the push stem. In some embodiments, the needle assembly 406 is configured to be rotationally guided until the needle is positioned in the direction of the target nerve (e.g., GSN).

With continued reference to FIG. 17, the needle assembly 406 extends toward the target nerve at a location between two portions of the target nerve 418, 419. As described herein, the catheter body 410 is configured to be rotatable so as to orient the needle assembly 406, including the needle port 412, in prescribed direction (relative to the target nerve. In some embodiments, the needle port 412 penetrates the target nerve so as to deliver the chemical ablation therein. In some embodiments, the needle port 412 delivers the chemical ablation on and about an exterior surface of the target nerve. Accordingly, the chemical delivery enables ablation (e.g., circumferentially lyse) of the target nerve along the length from target nerve location 418 to target nerve location 419. In some embodiments, the target nerve circumference 418, 419 represents the ablation area, at a given location, wherein the portion of the target nerve between portions 418, 419 represents the length of the ablation area. In some embodiments, as described herein, the longer the length of the ablation area provides for a longer treatment period for a medical condition described herein (e.g., heart failure).

In some embodiments, the hollow needle stem 414 is in operative communication with a mechanism configured to supply the chemical to the needle assembly. In some embodiments, the chemical is supplied via a supply line connecting a chemical source (e.g., outside the subject) to the device. In some embodiments, the device comprises a stored supply of the chemical for delivery to or about the target nerve. In some embodiments, the chemical is supplied via an automatic controller. In some embodiments, the chemical is supplied via manual input. In some embodiments, the chemical comprises carbon dioxide, ethanol, liquid nitrogen, a conductive substance (e.g., saline, specialized hydrogel, etc.), or a combination thereof.

In some embodiments, the electrode region area 407 is configured to provide a stimulation to the target nerve (via for example, neurostimulation electrodes described herein). In some embodiments, the electrode region is positioned within the subject (for e.g., using radiopacity markers and/or a neurosensory region) at a location that corresponds to the target nerve (e.g., location may be perpendicular to an axis of the catheter body 410). Accordingly, in some embodiments, stimulation is provided via signals delivered perpendicularly. In some embodiments, the configuration of the needle assembly extending from the catheter body correlates with a positioning of the electrode region 407.

Figure 19:
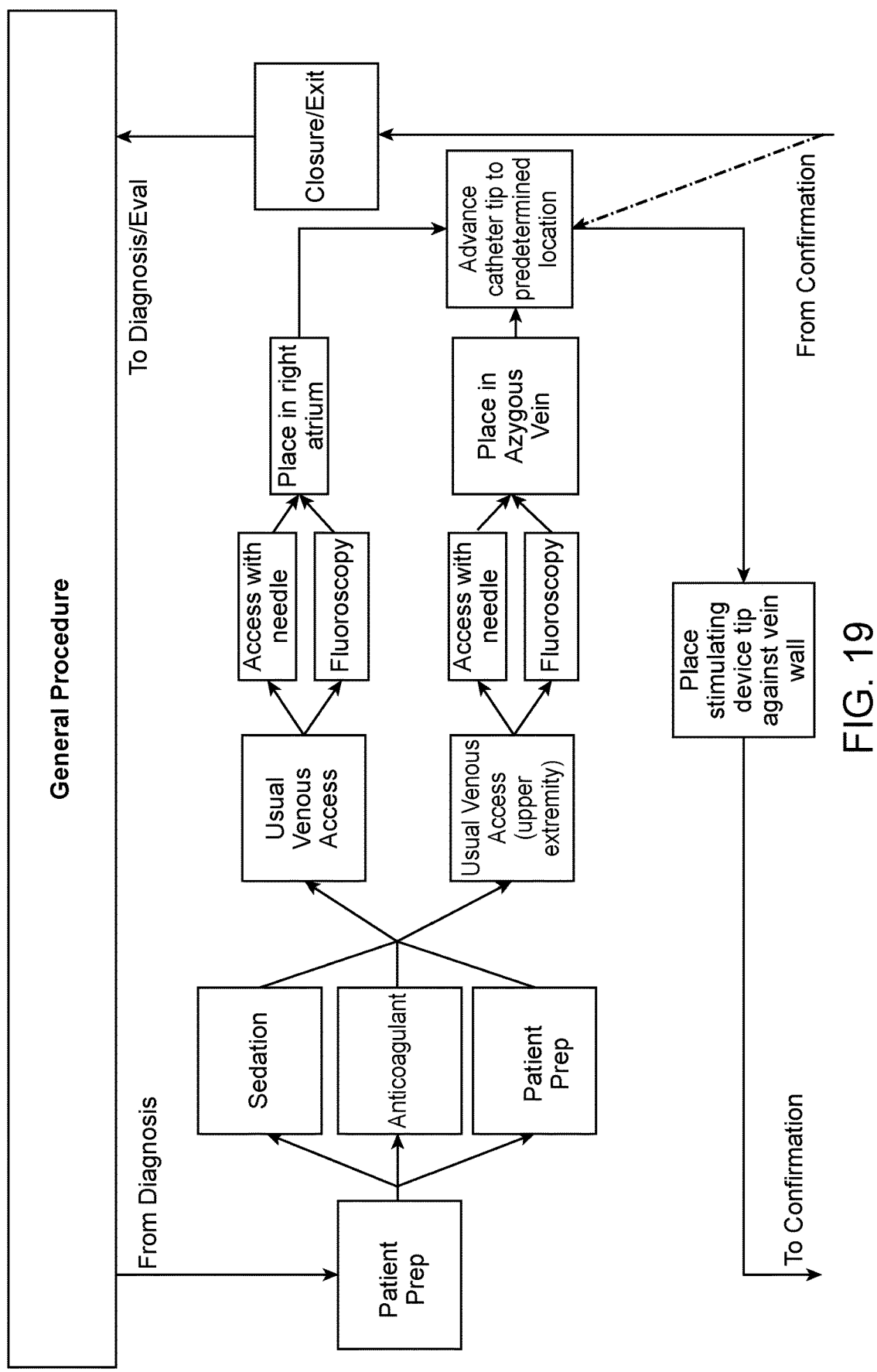
FIG. 19 depicts an exemplary embodiment of the device according to FIG. 18 with an ultrasound device.

FIGS. 18-21 depict an exemplary process for treating medical condition as described herein, wherein the process is categorized under 4 components of the exemplary process: Diagnosis, General Procedure, Site-Recognition/Confirmation, and Ablation. FIG. 19 depicts exemplary steps for the General Procedure category, which include patient prep steps, such introduce a device (e.g., catheter device) within a subject and advancing the device to a predetermined location.

Figure 20:
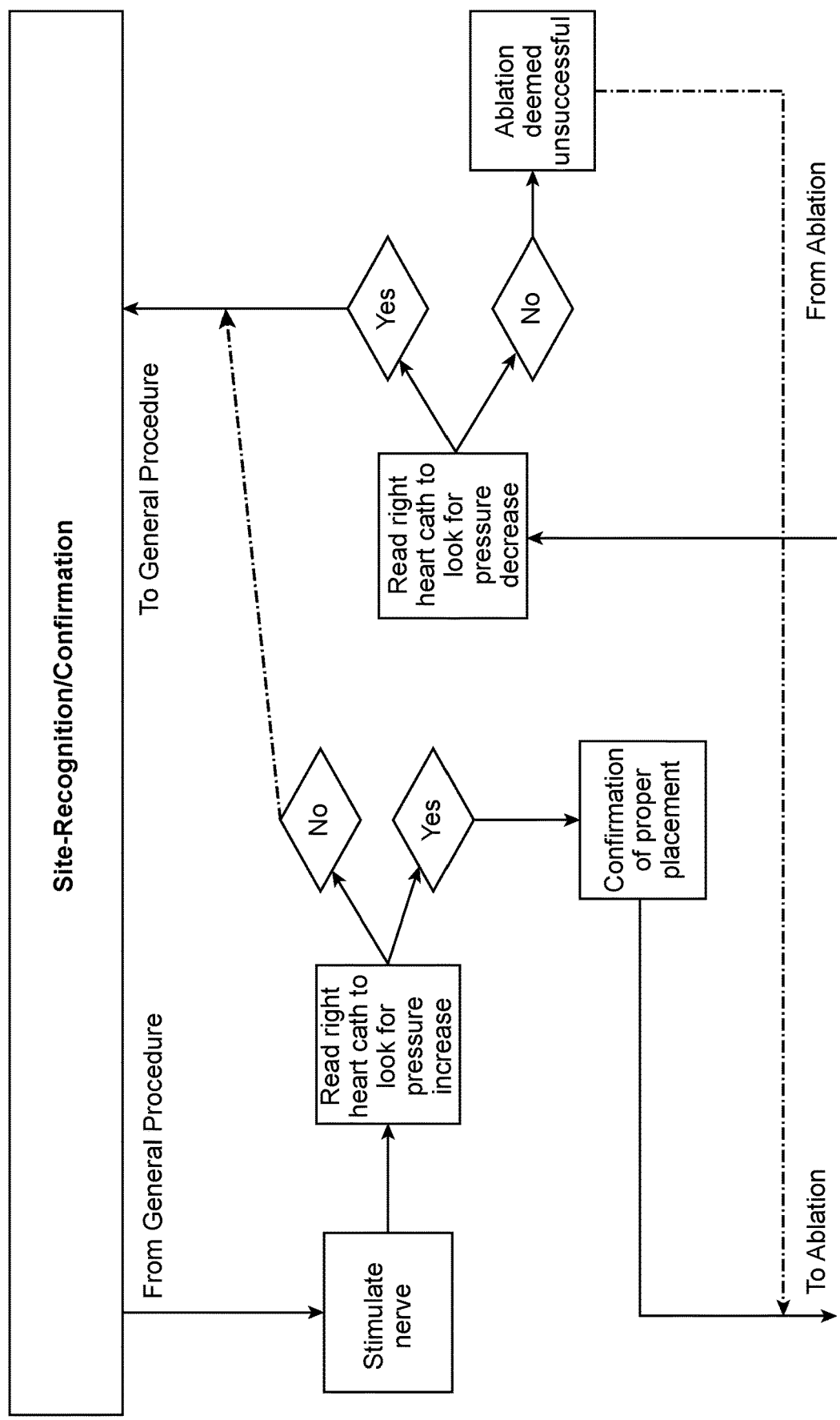
FIG. 20 depicts an exemplary embodiment of the device according to FIG. 18 with an ultrasound device and expanded expandable balloon.
Figure 21:
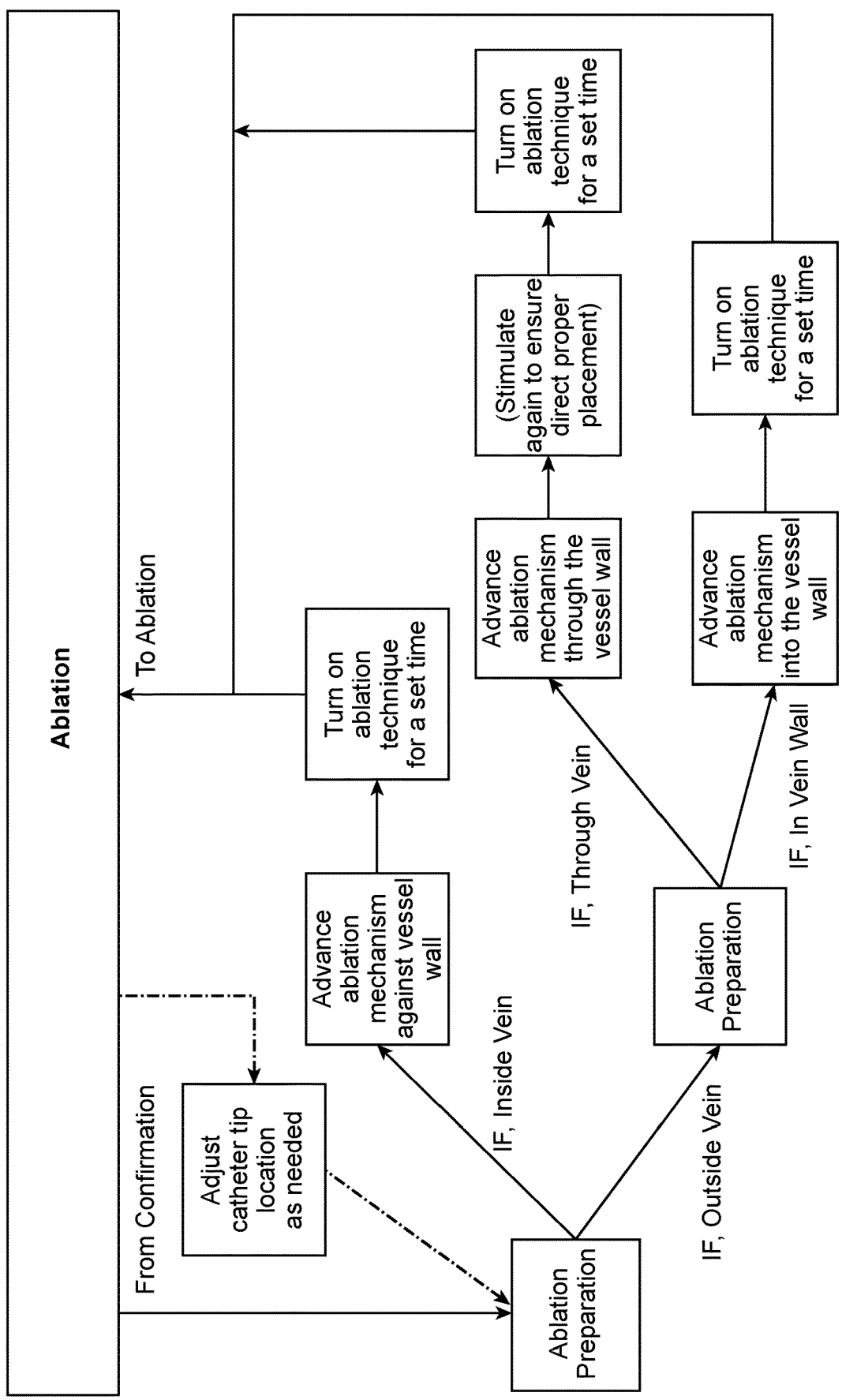

FIG. 20 depicts exemplary steps for the Site-Recognition/Confirmation category, which includes confirming the location of a target nerve via nerve stimulation and corresponding nerve activity and/or physiological changes (e.g., sympathetic response) detected. FIG. 21 depicts exemplary steps for the Ablation category, including various ablation modalities, such as ablation from within a vein, artery, or vessel (e.g., ultrasound, linear electrode array), through the vein wall (e.g., see FIGS. 6, 13, and 17), and within the vein wall.

FIGS. 23A-27B depict an exemplary depiction of the device 2300 described herein, wherein a telescopic needle assembly comprising an extendable needle and an electrode assembly, with a first section surrounding a second section, wherein the second section extends outwards from the first section, and which is used to ablate a target nerve. In some embodiments, with reference to FIG. 23A/B, the device comprises a catheter shaft 2311, a handle 2306, a contrast port 2301, a guidewire port 2302, a catheter rotation knob 2303, an electrode advancer 2304, a rotary electrical connector 2305, a catheter tip 2316, an ablation needle exit port 2312, an ablation needle lumen 2314, a guidewire lumen 2318, a maker band 2317, a second marker band 2315, and a needle assembly 2313 comprising one or more electrodes (e.g., for neurostimulation or nerve ablation). FIG. 23B illustrates the needly assembly fully extended 2319 from the device. In some embodiments, the catheter, ablation needle, guidewire port 2302, contrast port 2301, and rear connector 2305 spin in unison. In some embodiments, a guidewire is inserted into the guidewire port 2302 and is used to drives the catheter within a vascular lumen. In some embodiments, the contrast port 2302 is used for insertion of fluoroscopic contrast. In some embodiments, the rear connector includes pins for two ablation poles and three nerve stimulation and nerve monitoring leads. In some embodiments, the keyway within the handle 2306 couples the rotation of the control knob and control catheter with the rear electrical connector and routes electrical connections to allow for continuous rotation. In some embodiments, the electrode advancer provides sufficient travel for the distal end of the ablation needle (e.g., needle assembly) to extend about 1-2 cm, in some cases 1.5 cm, from the catheter midline. In some embodiments, the needle assembly comprising one or more electrodes is not extended. In some embodiments, the needle assembly comprising one or more electrodes is extended. In some embodiments, the electrode advancer 2304 is used to extend the electrode assembly into vascular tissues, e.g., puncture a vascular tissue. In some embodiments, the guidewire is inserted into the guidewire lumen to advance the catheter tip 2316 into an intravascular space. In some embodiments, the electrode advancer advances a first tubular body of the needle assembly comprising a first proximal electrode and then a second tubular body extends from the first tubular body, and the extension length of the telescopic electrode assembly can be controlled by the user. In some embodiments, the guidewire is advances separately from the needle assembly comprising the one or more electrodes. In some embodiments the rear electrical connector has three pins for nerve sensing and two bi-polar ablation poles. In some embodiments, the catheter length is from about 25-150 cm, in some cases 120 cm. In some embodiments, the nerve sensing elements one or more electrodes on a catheter shaft substrate that is wrapped around the catheter shaft 2311 and bonded in place. In some embodiments, the one or more electrodes on the needle assembly are the nerve sensing elements. In some embodiments, the one or more electrodes on a catheter shaft, or the one or more electrodes on the needle assembly, is used to confirm placement of the needle prior to ablation via low power stimulation to observe the patient's heart rate. In some embodiments, the device comprises a radiopaque area 404, which may be used to help track the location of the device within a subject. In some embodiments, the radiopaque area is located anywhere on the catheter body. In some embodiments, radiopacity helps enable rotational accuracy for positioning the needle assembly (as described herein). In some embodiments, the radiopaque mark appears different on the catheter body at 90 degree increments, thereby helping direct the needle assembly in the superior/inferior, anterior/posterior, lateral/medial, and/or cranial/caudal directions. In some embodiments, an electrical charge is delivered from a first electrode, which can be positive, to a second electrode, which can be negative, thereby sending energy to nearby vascular tissue and heating it to approximately 40 C, 50 C, or 60 C.

Figure 24A:
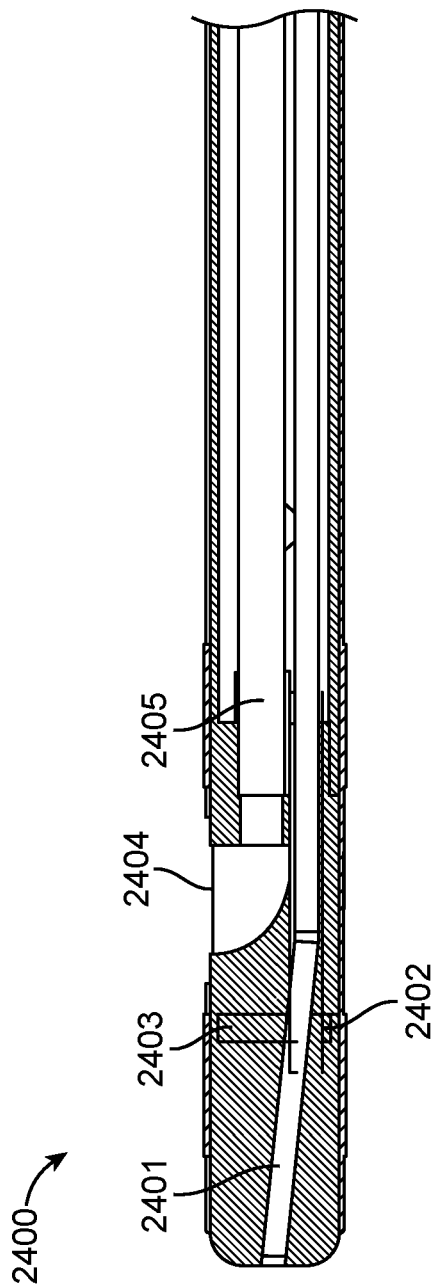
FIG. 24A depicts a close up cross sectional view of an exemplary device used for treating a medical condition as described herein.
Figure 24B:
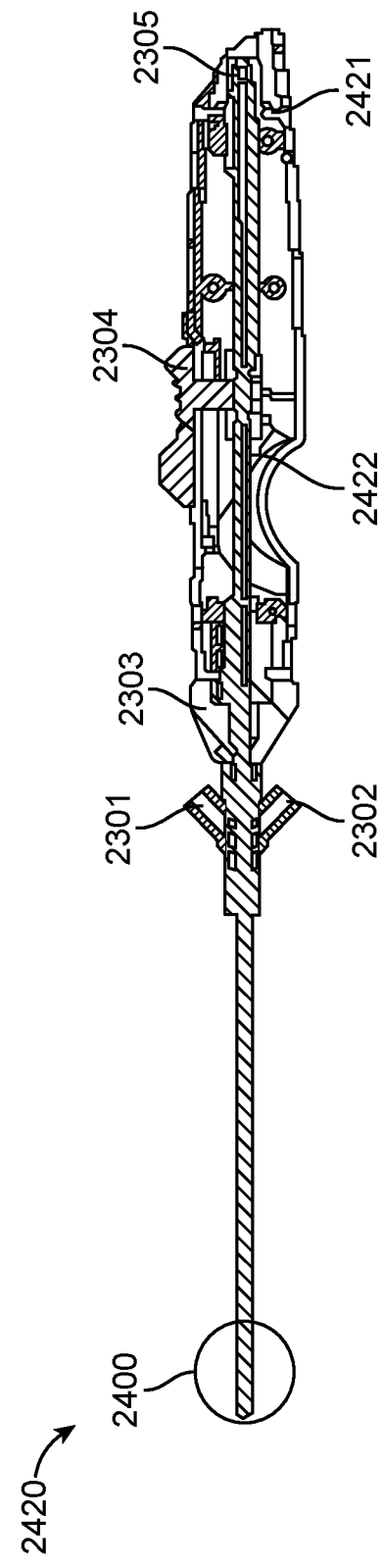
FIG. 24B depicts a cross sectional view of an exemplary device used for treating a medical condition as described herein.

With reference to FIGS. 24A/B, an exemplary depiction of the catheter tip 2400 of the device 2420 is shown. In some embodiments, with reference to FIG. 24A, the catheter tip comprises a guidewire lumen 2401, a marker band 2402/2403, an ablation needle exit port 2404, and a needle assembly 2313 comprising one or more electrodes, for example, a silk screened electrode. In some embodiments, with reference to FIG. 24B, device 2420 comprises a contrast port 2301, a guidewire port 2302, a catheter rotation knob 2303, an electrode advancer 2304, a rotary electrical connector 2305, a rotation coupler 2421, and a rotation coupler 2422. In some embodiments, device 2420 is device 2300.

With reference to FIGS. 25A/B, an exemplary depiction of the telescopic needle assembly 2500 of the device 2300 is shown. In some embodiments, with reference to FIG. 25A, the needle assembly comprises an enamel coated wire 2501, a proximal laser cut hypotube 2502 which may be a tubular body, a proximal laser cut hypotube polyimide insulator 2503, a first electrode band 2504, a second electrode band 2510, a laser cut hypotube dielectric washer 2506, an inner polyimide linear 2505, a distal polyimide cover 2509, a distal laser cut hypotube 2508 which may be a tubular body, and a solder paste or laser weld 2507. The needle assembly may terminate in a point configured to puncture vascular tissue. In some embodiments, the enamel coated wire 2501 conducts electricity to one or more electrodes positioned on an outer surface of the needle assembly, for example, on an outer surface of the proximal laser cut hypotube 2502 (e.g., a tubular body), or on an outer surface of a distal laser cut hypotube 2508 (e.g., a tubular body). In some embodiments, the laser cut hypotube dielectric washer 2506 and inner polyimide linear 2505 are insulating. In some embodiments, one or more electrodes 2504/2510 are electrical poles on the ablation needle assembly 2500, and may be marker bands. In some embodiments, with reference to FIG. 25B, the needle assembly comprises a longitudinal axis 2512, a distal laser cut hypotube 2508 (e.g., tubular body), a first electrode 2504, a second electrode 2510, and a proximal laser cut hypotube 2502 (e.g., tubular body).

Figure 26A:
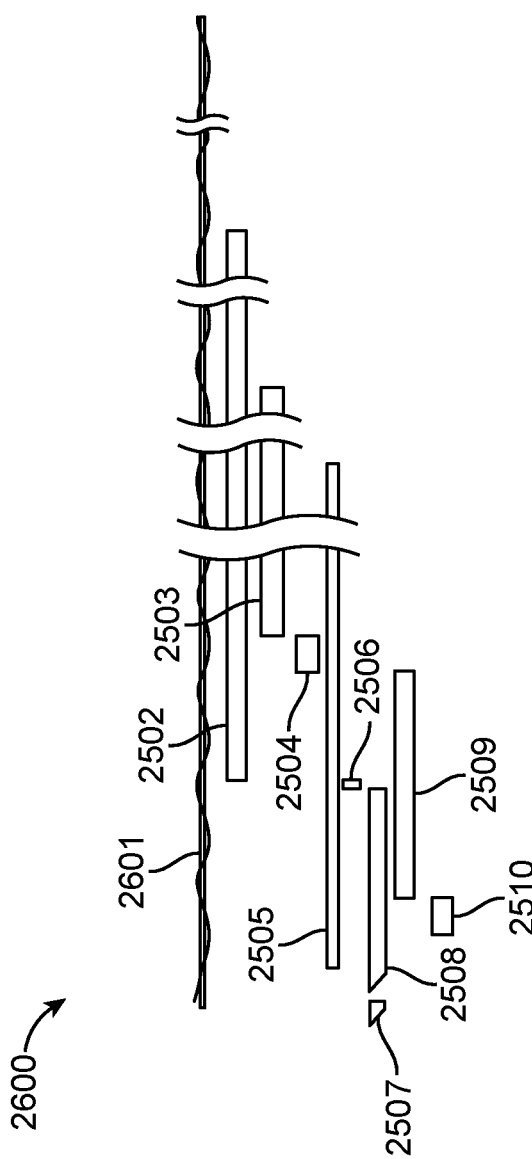
FIG. 26A depicts an exploded view of the needle assembly of an exemplary device used for treating a medical condition as described herein.
Figure 26B:
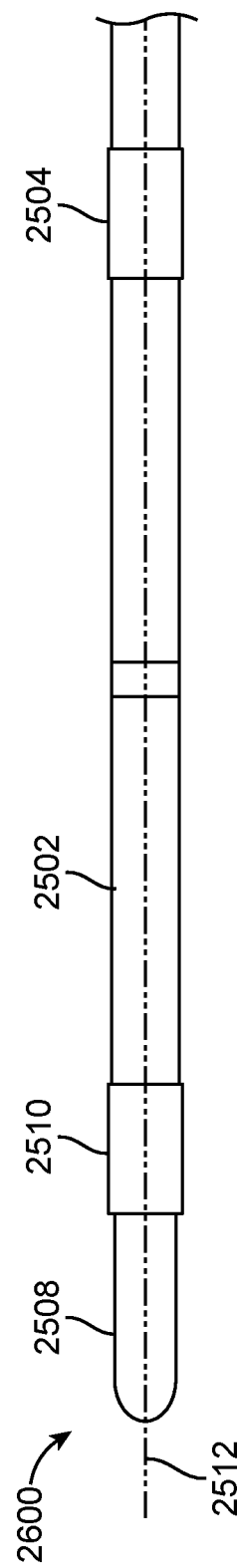
FIG. 26B depicts the needle assembly of an exemplary device used for treating a medical condition as described herein.

With reference to FIGS. 26A/B, an exemplary depiction of the telescopic needle assembly 2600 of the device 2300 is shown. The telescopic needle assembly may comprise a first section surrounding a second section, wherein the second section extends outwards from the first section. In some embodiments, the first section comprises a first tubular body, wherein the second section comprises a second tubular body, wherein the first tubular body extends outward from the second tubular body, and wherein the first tubular body nests within the second tubular body such that the tubular body is fully or partially contained within the first tubular body. In some embodiments, with reference to FIG. 26A, the needle assembly comprises a multi-strain braid 2601 which may be conductive, a proximal laser cut hypotube 2502 (e.g., a tubular body), a proximal laser cut hypotube polyimide insulator 2503, a first electrode 2504, a second electrode 2510, a laser cut hypotube dielectric washer 2506, an inner polyimide linear 2505, a distal polyimide cover 2509, a distal laser cut hypotube 2508 (e.g., a tubular body), and a solder paste or laser weld 2507. The needle assembly may terminate in a point configured to puncture vascular tissue. In some embodiments, the multi-strain braid 2601 conducts electricity to one or more electrodes 2504/2510 positioned on an outer surface of the needle assembly, for example, on an outer surface of the proximal laser cut hypotube 2502 (e.g., a tubular body), or on an outer surface of a distal laser cut hypotube 2508 (e.g., a tubular body). In some embodiments, the laser cut hypotube dielectric washer 2506 and inner polyimide linear 2505 are insulating. In some embodiments, one or more electrodes 2504/2510 are electrical poles on the ablation needle assembly 2600, and may be marker bands. In some embodiments, with reference to FIG. 26B, the needle assembly comprises a longitudinal axis 2512, a distal laser cut hypotube 2508, a marker band 2504, a marker band 2510, and a proximal laser cut hypotube 2502. In some embodiments, the needle assembly further comprises a third section comprising a sharp distal point, wherein the second section surrounds the third section, wherein the third section extends outward from the second section.

Figure 27A:
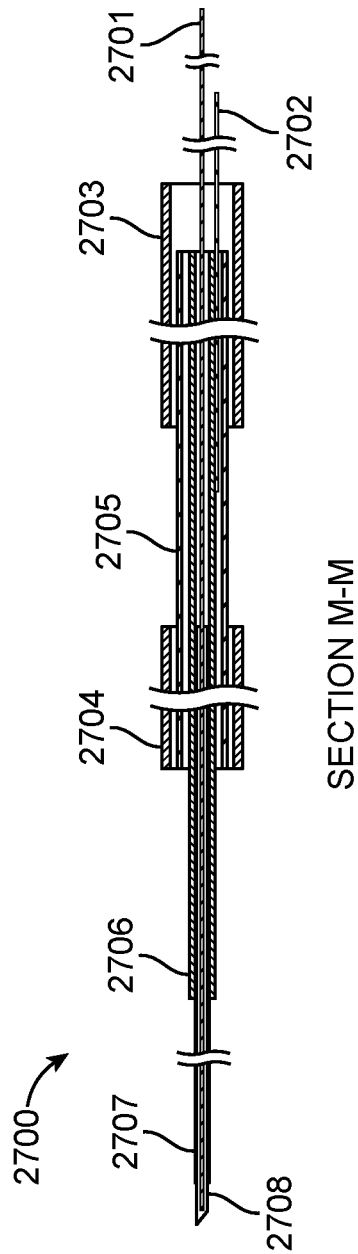
FIG. 27A depicts a cross sectional view of the needle assembly of an exemplary device used for treating a medical condition as described herein.
Figure 27B:
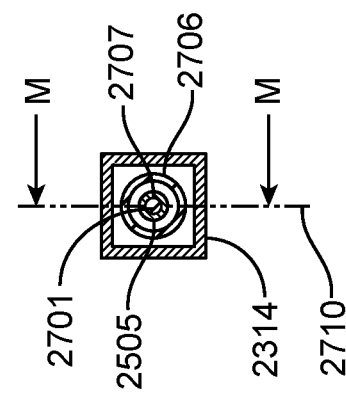
FIG. 27B depicts a longitudinal cross sectional view of the needle assembly of an exemplary device used for treating a medical condition as described herein.

With reference to FIG. 27, an exemplary depiction of the telescopic needle assembly comprising the electrode assembly 2700 of the device 2300 is shown. In some embodiments, the telescopic needle assembly comprises a first section surrounding a second section, wherein the second section extends outwards from the first section. In some embodiments, the first section comprises a first tubular body, wherein the second section comprises a second tubular body, wherein the first tubular body extends outward from the second tubular body, and wherein the first tubular body nests within the second tubular body such that the tubular body is fully or partially contained within the first tubular body. In some embodiments, the needle assembly further comprises a third section comprising a sharp distal point, wherein the second section surrounds the third section, wherein the third section extends outward from the second section. In some embodiments, with reference to FIG. 27A, the electrode assembly comprises an enamel coated wire 2701/2702, a rear keyway 2703, a front keyway 2704, a rotary hub 2705, a proximal support tube 2706 (e.g., tubular body), a distal laser cut hypotube 2707 (e.g., tubular body), and a distal laser cut hypotube tip 2708 (e.g., tubular body, which may terminate in a point). In some embodiments, the distal laser cut hypotube 2707 (e.g., tubular body) is bonded to the support tube 2706 with conductive epoxy. In some embodiments, the proximal enamel-coated wire 2702 is tinned and placed between the proximal support tube 2706 and rotary hub 2705 before they are also bonded using conductive epoxy. In some embodiments distal laser cut hypotube 2707 (e.g., tubular body) extends until a first length, at which point second portion distal laser cut hypotube tip 2708 (e.g., tubular body) will extend. In some embodiments, with reference to FIG. 27B, there is a cross-sectional view of 2700. In some embodiments, the cross-sectional view has a vertical axis 2710. In some embodiments, the cross-sectional view includes needle lumen 2314, enamel coated wire 2701, a proximal support tube 2706, a distal laser cut hypotube 2707, and an inner polyimide linear 2505. Illustrated in FIG. 27B is the telescopic nesting of some embodiments of the needle assembly. In some embodiments, there may be a needle lumen which encloses within it a proximal support tube 2706 (e.g., tubular body), which encloses within it distal laser cut hypotube 2707 (e.g., tubular body), which encloses within it a proximal support tube 2706 (e.g., tubular body), which encloses within it a conductive wire, e.g., an enamel coated 2701. The distal laser cut hypotube 2707 (e.g., tubular body) may extend the furthest from a longitudinal axis of the catheter and pierce the wall of a vascular lumen which the catheter is positioned within. Once the proximal support tube 2706 (e.g., tubular body) is fully extended, the distal laser cut hypotube 2707 (e.g., tubular body) may extend outward from the proximal support tube 2706 such that the needle assembly may be fully extended. The needle may nest within itself in a telescopic configuration with the distal laser cut hypotube 2707 (e.g., tubular body) extending from within the proximal support tube 2706 (e.g., tubular body), with the proximal support tube 2706 (e.g., tubular body) extending outwards from the catheter. There are a number of beneficial technical effects of the telescopic needle assembly disclosed herein including, improved ablation, reduction of trauma, smoother insertion and retraction the needle assembly, ease of manufacture, and increased control of ablation parameters and ablation length. For example, the telescopic configuration of the needle assembly may be advantageous over alternative configurations in that it may minimize sharp force trauma to vascular tissue which it is penetrating, and other tissue surrounding the target nerve, when it is extended, as it may primarily extend in a straight (or relatively straight) vector which will not displace tissue adjacent to the telescopic needle assembly. Further, the telescopic and may be more likely to properly extend and retract without trapping vascular tissue within the needle assembly or in between components of the needle assembly as compared to a bifurcating configuration. In some cases, the length of extension of the telescopic needle assembly comprising the electrode assembly can be controlled by an operator, and the length between the electrodes on the telescopic needle assembly can be varied, permitting for increased ablation length for configurations with a larger displacement between the electrodes, or reduced ablation length for configurations with a smaller displacement between the electrodes. In some embodiments, the ease of extension of the telescopic needle assembly may improve the operator's ability to achieve or maintain a desired electrode displacement in order to achieve desired ablation parameters, for example achieving desired electrode displacement, or desired displacement from or proximal to a target nerve. The telescopic needle assembly may also be easier to manufacture as compared to bifurcated assembly, such that a first section may nest within a second section of the needle assembly.

EXAMPLES

Example 1: Nerve Ablation Catheter with Bifurcated Needle Assembly

Figure 2:
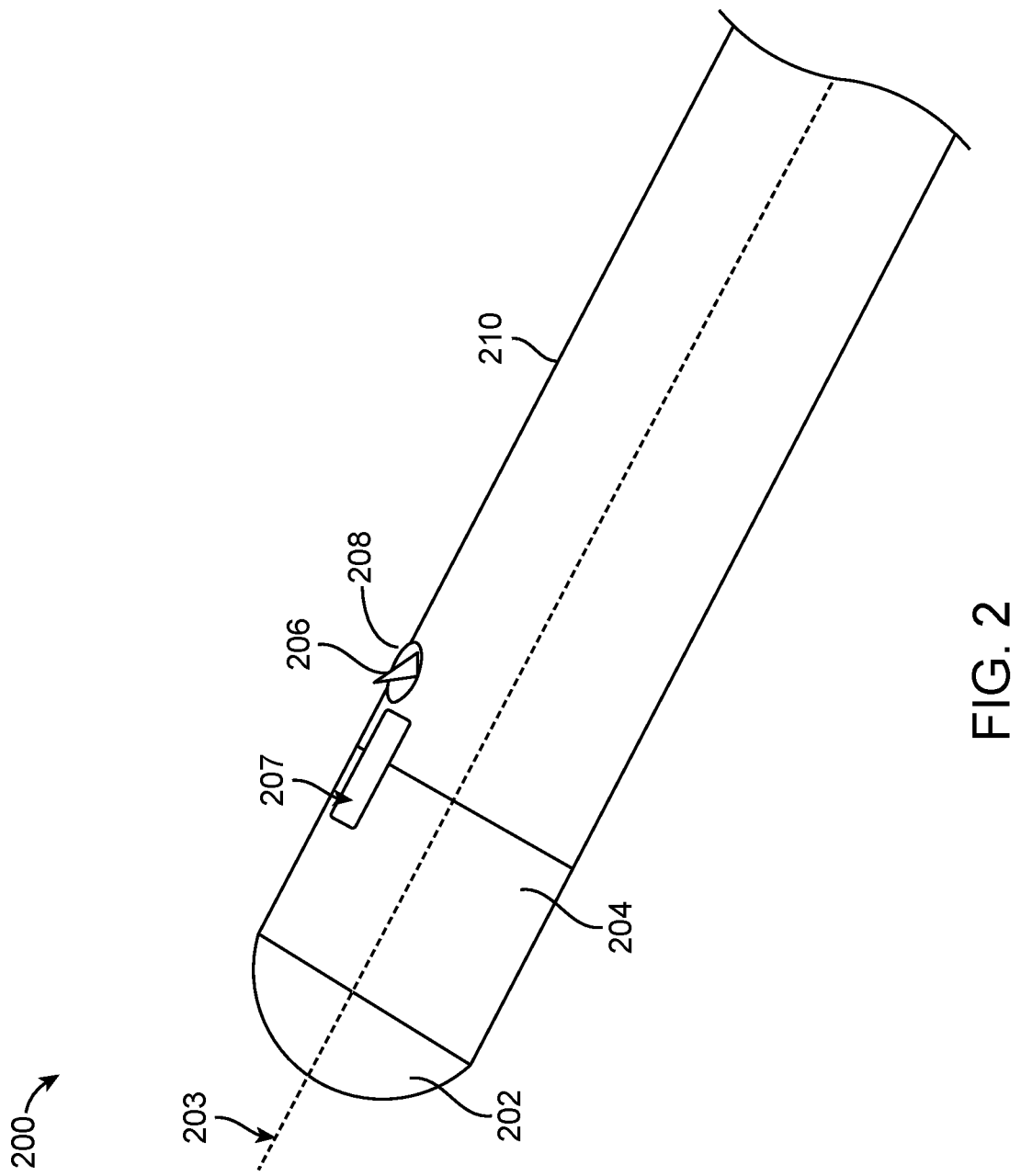
FIG. 2 depicts an exemplary first embodiment of a device used for treating a medical condition as described herein.

A vascular catheter device comprising a needle assembly is provided. With reference to FIGS. 2-3, the device comprises a device body (e.g., catheter body) 210, a catheter tip 202, a needle assembly 206 configured to be disposed within the catheter body, an opening 208 for the needle assembly 206 to extend from, and an electrode region 207 (e.g., for neurostimulation). The opening 208 is a lateral opening, and the device body 210 has a longitudinal axis (203). The electrode region is also the same location as a neurosensory region (e.g., for measuring action potentials), which can be located anywhere on the catheter body 210. The device comprises a radiopaque area 204, which may be used to help track the location of the device within a subject. The radiopaque area is located anywhere on the catheter body, and helps enable rotational accuracy for positioning the needle assembly (as described herein). The device further comprises radiopaque marks at different locations on the catheter body at 90 degree increments, thereby helping direct the needle assembly in the superior/inferior, anterior/posterior, lateral/medial, and/or cranial/caudal directions. The device body further comprises a needle lumen which extends within the device body and terminates at a lateral opening. The needle assembly comprises two needle-electrodes each comprising a separate needle.

A needle assembly push stem (or other structure) is provided within the catheter body 210 and configured to engage with the needle assembly so as to push the needle assembly 206 through the opening 208. In some embodiments, the push stem is located within the catheter body 210 and configured to be actuated so as to automatically push the needle assembly 206 out of the opening 208 when actuated by the user by an actuation member on the handle device. The needle assembly 206 is provided within a needle assembly tube located within the catheter body 210. The tube is configured to extend from the opening 208 to the vein wall, wherein the needle assembly is then configured to be extend from an end of the tube and puncture through the vein wall.

The catheter body 310 is configured to rotate so as to orient the needle assembly 306 in a prescribed direction relative to the target nerve. The needle assembly is configured to extend from the catheter body according to a specific configuration, which corresponds to the location of a radiopacity marker (e.g., 304), such that the direction and position of the electrodes on the needle assembly when extended can be correlated with the location of the radiopacity marker. radiopacity helps enable rotational accuracy for positioning the needle assembly (as described herein). The radiopaque mark appears different on the catheter body at 90 degree increments, thereby helping direct the needle assembly in the superior/inferior, anterior/posterior, lateral/medial, and/or cranial/caudal directions The electrodes 212, 213 are configured to ablate (e.g., circumferentially lyse) a length of the target nerve that is at least the length from target nerve location 220 to target nerve location 221. The target nerve circumference 220, 221 represents the ablation area (at a given location), and the portion of the target nerve between portions 220, 221 represents the length of the ablation area. As described herein, the longer the length of the ablation area provides for a longer treatment period for a medical condition described herein (e.g., heart failure).

Example 2: Nerve Ablation Catheter with Telescopic Needle Assembly

A vascular catheter device comprising a needle assembly is provided. With reference to FIGS. 23-27, the device comprises a catheter shaft 2311, a handle 2306, a contrast port 2301, a guidewire port 2302, a catheter rotation knob 2303, an electrode advancer 2304, a rotary electrical connector 2305, a catheter tip 2316, an ablation needle exit port 2312, an ablation needle lumen 2314, a guidewire lumen 2318, a maker band 2317, two marker bands 2315, and a silk screened electrode 2313 (e.g., for neurostimulation). The telescopic needle assembly with one or more electrodes may be extended 2319 as shown in FIG. 23B. The telescopic needle assembly comprises a first section surrounding a second section, wherein the second section extends outwards from the first section. The first section comprises a first tubular body, wherein the second section comprises a second tubular body, wherein the first tubular body extends outward from the second tubular body, and wherein the first tubular body nests within the second tubular body such that the tubular body is fully or partially contained within the first tubular body. In some embodiments, the needle assembly further comprises a third section comprising a sharp distal point, wherein the second section surrounds the third section, wherein the third section extends outward from the second section. In some embodiments, the catheter, ablation needle, guidewire port 2302, contrast port 2301, and rear connector 2305 spin in unison. In some embodiments, a guidewire may be inserted into the guidewire port 2302 which drives the catheter in the vascular tissue. In some embodiments, the contrast port 2302 is used for fluoroscopic contrast. In some embodiments, the rear connector includes pins for two ablation poles and three nerve stimulation and nerve monitoring leads. In some embodiments, the keyway within the handle 2306 couples the rotation of the control knob and control catheter with the rear electrical connector and routes electrical connections to allow for continuous rotation. In some embodiments, the electrode advancer provides sufficient travel for the distal end of the ablation needle to extend about 1.5 cm from the catheter midline. In some embodiments, the electrode advancer 2304 is used to extend the electrode assembly into vascular tissues, e.g., to puncture a vascular lumen which the catheter is within, and the extension length of the telescopic electrode assembly can be controlled by the user. In some embodiments, the guidewire is inserted into the guidewire lumen to advance the catheter tip 2316 into an intravascular space. In some embodiments, the electrode advancer advances the outermost electrode and then a second portion extends from the first portion. In some embodiments, the guidewire advances separately from the electrode. In some embodiments the rear electrical connector has three pins for nerve sensing and two bi-polar ablation poles. In some embodiments, the catheter length is about 120 cm. In some embodiments, the nerve sensing elements are electrodes 2313 on the catheter shaft substrate wrapped around the catheter shaft 2311 and bonded in place. In some embodiments, the one or more electrodes on the needle assembly is used to confirm placement of the needle prior to ablation via low power stimulation to observe the patient's heart rate. In some embodiments, the device comprises a radiopaque area 404, which may be used to help track the location of the device within a subject. In some embodiments, the radiopaque area is located anywhere on the catheter body. In some embodiments, radiopacity helps enable rotational accuracy for positioning the needle assembly (as described herein). In some embodiments, the radiopaque mark appears different on the catheter body at 90 degree increments, thereby helping direct the needle assembly in the superior/inferior, anterior/posterior, lateral/medial, and/or cranial/caudal directions. In some embodiments, an electrical charge is delivered from a first electrode, which can be positive, to a second electrode, thereby sending energy to nearby vascular tissue and heating it to approximately 40 C, 50 C, or 60 C.

A needle assembly push stem (or other structure) is provided within the catheter shaft 2311 and configured to engage with the needle assembly so as to push the needle assembly 2500, or, in other embodiments, needle assembly 2600, through the ablation needle exit port 2315. In some embodiments, the push stem is located within the catheter shaft 2311 and configured to be actuated so as to advance the needle assembly 2500, or, in other embodiments, needle assembly 2600, out of the ablation needle exit port 2315 when actuated by the user by an actuation member on the handle device. The needle assembly 2500, or, in other embodiments, needle assembly 2600, is provided within a catheter assembly tube located within the catheter shaft 2311. The electrode within needle assembly 2500, or, in other embodiments, needle assembly 2600, is configured to extend from the ablation needle exit port 2315 to the vein wall, wherein the needle assembly is then configured to extend from an end of the tube and puncture through the vein wall.

The catheter shaft 2311 is configured to rotate so as to orient the needle assembly 2500, or, in other embodiments, needle assembly 2600, in a prescribed direction relative to the target nerve. The needle assembly is configured to extend from the catheter body according to a specific configuration, which corresponds to the location of a radiopacity marker (e.g., 304), such that the direction and position of the electrodes on the needle assembly when extended can be correlated with the location of the radiopacity marker. radiopacity helps enable rotational accuracy for positioning the needle assembly (as described herein). The radiopaque mark appears different on the catheter body at 90 degree increments, thereby helping direct the needle assembly in the superior/inferior, anterior/posterior, lateral/medial, and/or cranial/caudal directions The electrode configuration 2700 is configured to ablate (e.g., circumferentially lyse) a length of the target nerve. As described herein, the longer the length of the ablation area provides for a longer treatment period for a medical condition described herein (e.g., heart failure).

As compared to a non-telescopic needle assembly of Example 1, the telescopic needle assembly may result in improved ablation, reduction of trauma to vascular tissue and tissue surrounding the target nerve, smoother insertion and retraction the needle assembly, ease of manufacture, and increased control of ablation parameters and ablation length. For example, the telescopic configuration of the needle assembly minimizes sharp force trauma to vascular tissue which it is penetrating, and other tissue surrounding the target nerve, when it is extended, as it extends in a straight (or relatively straight) vector which will not displace tissue adjacent to the telescopic needle assembly. Further, the telescopic has a greater tendency to properly extend and retract without trapping vascular tissue within the needle assembly or in between components of the needle assembly as compared to the bifurcating configuration. Further, the length of extension of the telescopic needle assembly comprising the electrode assembly can be controlled by the operator, and the displacement between the electrodes on the telescopic needle assembly can be varied, permitting for increased ablation length for configurations with a larger displacement between the electrodes, or reduced ablation length for configurations with a smaller displacement between the electrodes. The ease of extension of the telescopic needle assembly improves the operator's ability to achieve or maintain a desired electrode displacement relative to each electrode in order to achieve desired ablation parameters, for example achieving desired electrode displacement. Similarly, ease of extension of the telescopic needle assembly improves the operator's ability to achieve the or desired displacement from or proximal to a target nerve by permitting the operator to vary the insertion depth of the telescopic needle assembly. Collectively, these features may permit for a surgeon to account for varying patient anatomy with the telescopic needle assembly. The telescopic needle assembly may also be easier to manufacture as compared to bifurcated assembly, such that a first section may nest within a second section of the needle assembly.

Example 3: Outpatient Treatment of Treatment Resistant Heart Failure

A patient with treatment-resistant heart failure presents to a cardiology clinic. The patient expresses to the physician that they do not have the energy level they used to and frequently feels "winded" or "short of breath" after minimal physical activity, such as walking one city block, or going up or down one flight of stairs. The patient may have been previously evaluated by other physicians and then referred to cardiology clinic. The patient displays other symptoms indicative of heart failure, for example, early fatigue, orthopnea, paroxysmal nocturnal dyspnea, dsypnea on exertion, or tachycardia episodes. Previously, the patient reports being able to walk a mile or more without experiencing the complained of symptoms. This patient is already on Lasix (diuretics or water pills), blood pressure medications, generic equivalents, or combinations thereof, but there is no improvement to the complained of symptoms. There are no additional options for pharmacotherapy at this time. The physical exam shows evidence of volume overload (fluid in the lungs, swelling in the legs, elevated jugular vascular pressure/pulsations). The cardiologist notes the patient is a New York Heart Association (NYHA) Class II or Class III severity patient, depending on the level of exercise capacity. Other criteria or indicators of HF severity include brain naturistic peptide levels and number of hospitalizations over a recent time frame (at least 1 admission over the past year). This patient may or may not have usual comorbidities of hypertension, kidney disease, liver disease, high cholesterol, and diabetes, among other issues. The cardiologist then refers the patient for a splanchnic nerve ablation procedure, which will take place in the outpatient catheterization lab affiliated with the clinic.

A catheter based device as described in Example 2 is utilized. The catheter device accesses the vascular system via Seldinger technique through the jugular vein. The access sheath is navigated to the superior vena cava under fluoroscopic guidance. The sheath will cannulate that as it goes vein from the superior vena cava, and a guidewire will traverse that azygos vein. The sheath will cannulate the azygos vein from the superior vena cava, and a guidewire will traverse the azygos vein. Using the anatomic landmark, T9, the guidewire can enter the left and/or right intercostal vein branch. Here the greater splanchnic nerve (GSN) is assumed to be nearby, and the device will be introduced over the guidewire to this location.

When the device has reached the location by anatomic landmarks observable on flurosocopy (bones, vessels, etc.), which may be confirmed by using the marker bands of the catheter device— optionally—proximity to the target nerve is confirmed by applying a stimulation energy at the location and measuring a physiological response to the stimulation, for example, muscle response in the abdomen or GI track, nerve activity, or cardiac activity. In some cases, the operator will use the device's neurostimulatory component to deliver a charge through electrodes strong enough to elicit a nerve response, but not strong enough to damage tissue. The sympathetic response of the GSN will be measured by detecting adverse changes in pulmonary capillary wedge pressures (PCWP), gastrointestinal changes including increased motility, changes in less palmer sweating, changes in temperature for rectal and/or skin measurement, in renal output in relation to changes in vascular dilation, changes in metabolism (i.e. decreased glucose and glucagon release), and increases in brain natriuretic peptide. By eliciting these response(s), the user can confirm proximity to the target nerve. PCWP are obtained with right heart catheter procedures that are routinely performed in the hospital. A right heart catheter procedure may include of percutaneous access through the jugular vein using the Seldinger technique in a sterile fashion. The Swan Ganz catheter has a balloon, which is inflated, that is threaded through to the superior vena cava, the right atrium, the right ventricle to the pulmonary outflow tract. The inflated balloon carries the catheter to a pulmonary artery, where it is wedged. Here, pressures detected are called pulmonary capillary wedge pressures, which are considered equivalent to left atrial pressures. Left atrial pressures are a surrogate measurement for left ventricular end-diastolic pressures. Assuming that there is no mitral valve disease, PCWP is a measurement of severity of heart failure. Higher PCWP indicates worsened severity of heart failure. Each of the other responses will be measured by specific aspects of devices.

The operator may, optionally, also use another component of the device to directly sense the nerve, using the same electrodes that the neurostimulatory component employs. When the operator is able to position the device to the approximate location of the GSN using anatomic landmarks, the device generator will be changed to a "nerve sensing" mode. The nerve sensing mode will use the electrodes to read for action potentials through the GSN. The electrodes may be separate electrodes located on the surface of the catheter device, or may be the one or more electrodes within the needle assembly. Data from the neurostimulatory component and the nerve sensing apparatus will be aggregated to tell the operator that the device is in the position to perform nerve destruction.

After the location of the nerve has been confirmed by a combination of neuro-stimulatory and nerve sensing functions evaluated by the software component of the generator, the vascular puncture mechanism is actuated in the direction of the nerve to perform the ablation. The puncture mechanism may optionally confirm the position using a combination of nerve-sensing, neuro-stimulation with physiologic response, and fluoroscopy identifying anatomic landmarks, as described herein.

Then the nerve is ablated with radiofrequency ablation by applying an electrical stimulation to the electrode assembly. Electrical energy at about 50 W is transmitted from the power source to the electrode assembly on the needle assembly in proximity to the target nerve, and heating the target nerve and surrounding tissue to approximately 60 C.

Because nerves are able to regenerate, durability of effect is fundamentally related to the length of nerve tissue destroyed. In some cases, it is desirable to ablate a longer length of nerve (compared to intra-vascular ablation), leading to a longer duration of removal of sympathetic activity. Thus, patients will experience relief from heart failure symptoms for a longer period of time. In some cases, it is desirable to control the direction of the ablation modality. By focusing the ablation modality to the length of nerve, the operator can minimize collateral damage to other organs.

Next, procedure success may be evaluated by repeating the combination of nerve-sensing, neuro-stimulation with physiologic response. The device's neurostimulatory component delivers a charge through electrodes strong enough to elicit a nerve response, but not strong enough to damage tissue. The sympathetic response of the GSN will be measured by physiological changes as described above. The nerve-sensing component will detect lack of nerve activity, indicating the nerve has successfully been circumferentially lysed. The procedure will be considered incomplete if there is a physiologic response and/or if there is nerve activity sensed by the catheter device. The procedure will be repeated to lyse the nerve circumferentially, at the same site or a different site between two intercostal pairs.

After the procedure is performed, the patient is re-evaluated in the clinic one month later. Here the patient is noted to have more energy and exercise level; he/she can walk more than one block of stairs without having to rest. The cardiologist notes that the patient is improved one NYHA Class of severity with fewer hospitalizations.

Example 4: Inpatient Treatment of Heart Failure

A patent is hospitalized for heart failure exacerbation due to volume overload and has had repeated admissions in the recent past. He/she requires respiratory support (i.e. oxygen, external ventilation, or intubation) and is on intravascular diuretic therapy to remove excess fluid. Other standard treatments are included. This patient may or may not have usual comorbidities of hypertension, kidney disease, liver disease, high cholesterol, and diabetes, among other issues. In this case, the intravascular treatment is not able to remove fluid well, and the patient still shows signs of volume overload, and/or respiratory failure. The decision is made to perform the splanchnic nerve ablation procedure, while hospitalized.

A catheter based device as described in Example 2 is utilized. The catheter device accesses the vascular system via Seldinger technique through the jugular vein. The access sheath is navigated to the superior vena cava under fluoroscopic guidance. The sheath will cannulate that as it goes vein from the superior vena cava, and a guidewire will traverse that azygos vein. The sheath will cannulate the azygos vein from the superior vena cava, and a guidewire will traverse the azygos vein. Using the anatomic landmark, T9, the guidewire can enter the left and/or right intercostal vein branch. Here the greater splanchnic nerve (GSN) is assumed to be nearby, and the device will be introduced over the guidewire to this location.

When the device has reached the location by anatomic landmarks observable on flurosocopy (bones, vessels, etc.).), which may be confirmed by using the marker bands of the catheter device— optionally—proximity to the target nerve is confirmed by applying a stimulation energy at the location and measuring a physiological response to the stimulation, for example, muscle response in the abdomen or GI track, nerve activity, or cardiac activity. In some cases, the operator will use the device's neurostimulatory component to deliver a charge through electrodes strong enough to elicit a nerve response, but not strong enough to damage tissue. The sympathetic response of the GSN will be measured by detecting adverse changes in pulmonary capillary wedge pressures (PCWP), gastrointestinal changes including increased motility, changes in less palmer sweating, changes in temperature for rectal and/or skin measurement, in renal output in relation to changes in vascular dilation, changes in metabolism (i.e. decreased glucose and glucagon release), and increases in brain natriuretic peptide. By eliciting these response(s), the user can confirm proximity to the target nerve. PCWP are obtained with right heart catheter procedures that are routinely performed in the hospital. A right heart catheter procedure consists of percutaneous access through the jugular vein using the Seldinger technique in a sterile fashion. The Swan Ganz catheter has a balloon, which is inflated, that is threaded through to the superior vena cava, the right atrium, the right ventricle to the pulmonary outflow tract. The inflated balloon carries the catheter to a pulmonary artery, where it is wedged. Here, pressures detected are called pulmonary capillary wedge pressures, which are considered equivalent to left atrial pressures. Left atrial pressures are a surrogate measurement for left ventricular end-diastolic pressures. Assuming that there is no mitral valve disease, PCWP is a measurement of severity of heart failure. Higher PCWP indicates worsened severity of heart failure. Each of the other responses will be measured by specific aspects of devices.

The operator may, optionally, also use another component of the device to directly sense the nerve, using the same electrodes that the neurostimulatory component employs. When the operator is able to position the device to the approximate location of the GSN using anatomic landmarks, the device generator will be changed to a "nerve sensing" mode. The nerve sensing mode will use the electrodes to read for action potentials through the GSN. The electrodes may be separate electrodes located on the surface of the catheter device, or may be the one or more electrodes within the needle assembly. Data from the neurostimulatory component and the nerve sensing apparatus will be aggregated to tell the operator that the device is in the position to perform nerve destruction.

After the location of the nerve has been confirmed by a combination of neuro-stimulatory and nerve sensing functions evaluated by the software component of the generator, the vascular puncture mechanism is actuated in the direction of the nerve to perform the ablation. The puncture mechanism may optionally confirm the position using a combination of nerve-sensing, neuro-stimulation with physiologic response, and fluoroscopy identifying anatomic landmarks.

Then the nerve is ablated with radiofrequency ablation by applying an electrical stimulation to the electrode assembly. Electrical energy at about 50 W is transmitted from the power source to the electrode assembly on the needle assembly in proximity to the target nerve, and heating the target nerve and surrounding tissue to approximately 60 C.

Because nerves are able to regenerate, durability of effect is fundamentally related to the length of nerve tissue destroyed. In some cases, it is desirable to ablate a longer length of nerve (compared to intra-vascular ablation), leading to a longer duration of removal of sympathetic activity. Thus, patients will experience relief from heart failure symptoms for a longer period of time. In some cases, it is desirable to control the direction of the ablation modality. By focusing the ablation modality to the length of nerve, the operator can minimize collateral damage to other organs.

Next, procedure success may be evaluated by repeating the combination of nerve-sensing, neuro-stimulation with physiologic response. The device's neurostimulatory component delivers a charge through electrodes strong enough to elicit a nerve response, but not strong enough to damage tissue. The sympathetic response of the GSN will be measured by physiological changes as described above. The nerve-sensing component will detect lack of nerve activity, indication the nerve has successfully been circumferentially lysed. The procedure will be considered incomplete if there is a physiologic response and/or if there is nerve activity sensed by the catheter device. The procedure will be repeated to lyse the nerve circumferentially, at the same site or a different site between two intercostal pairs.

After the procedure is performed, the volume status of the patient improves and the patient is re-evaluated in the clinic one month later. Here the patient is noted to have more energy and exercise level; he/she can walk more than one block of stairs without having to rest. The cardiologist notes that the patient is improved one NYHA Class of severity with fewer hospitalizations.

Example 5: Inpatient Treatment of Heart Failure with Alternative Surgical Method A patent is hospitalized for heart failure exacerbation due to volume overload and has had repeated admissions in the recent past. He/she requires respiratory support (i.e. oxygen, external ventilation, or intubation) and is on intravascular diuretic therapy to remove excess fluid. Other standard treatments are included. This patient may or may not have usual comorbidities of hypertension, kidney disease, liver disease, high cholesterol, and diabetes, among other issues. In this case, the intravascular treatment is not able to remove fluid well, and the patient still shows signs of volume overload, and/or respiratory failure. The decision is made to perform the splanchnic nerve ablation procedure, while hospitalized.

A catheter based device as described in Example 2 is utilized. The catheter device accesses the vascular system via Seldinger technique through the brachial, femoral, or subclavian vein. The catheter device may be elongated proportionally to the vein chosen for entry. The access sheath is navigated to the superior vena cava under fluoroscopic guidance. The sheath will cannulate that as it goes vein from the superior vena cava, and a guidewire will traverse that azygos vein. The sheath will cannulate the azygos vein from the superior vena cava, and a guidewire will traverse the azygos vein. Using the anatomic landmark, T10, from within the azygos bein, the device is rotated towards the patient's right side such that the needle is towards the patient's right side, using the radiographic marker to confirm position and orientation. Here, the guidewire can enter between two intercostal pairs, for example, T9 and T10, T10 and T11, T11 and T12, and/or T12 and L1. Here the greater splanchnic nerve (GSN) is assumed to be nearby, and the device will be introduced over the guidewire to this location.

When the device has reached the location by anatomic landmarks observable on flurosocopy (bones, vessels, etc.) which may be confirmed by using the marker bands of the catheter device— optionally—proximity to the target nerve is confirmed by applying a stimulation energy at the location and measuring a physiological response to the stimulation, for example, muscle response in the abdomen or GI track, nerve activity, or cardiac activity. In some cases, the operator will use the device's neurostimulatory component to deliver a charge through electrodes strong enough to elicit a nerve response, but not strong enough to damage tissue. The sympathetic response of the GSN will be measured by detecting adverse changes in pulmonary capillary wedge pressures (PCWP), gastrointestinal changes including increased motility, changes in less palmer sweating, changes in temperature for rectal and/or skin measurement, in renal output in relation to changes in vascular dilation, changes in metabolism (i.e. decreased glucose and glucagon release), and increases in brain natriuretic peptide. By eliciting these response(s), the user can confirm proximity to the target nerve. Pressures detected are called pulmonary capillary wedge pressures, which are considered equivalent to left atrial pressures. Left atrial pressures are a surrogate measurement for left ventricular end-diastolic pressures. Assuming that there is no mitral valve disease, PCWP is a measurement of severity of heart failure. Higher PCWP indicates worsened severity of heart failure. Each of the other responses will be measured by specific aspects of devices.

The operator may, optionally, also use another component of the device to directly sense the nerve, using the same electrodes that the neurostimulatory component employs. When the operator is able to position the device to the approximate location of the GSN using anatomic landmarks, the device generator will be changed to a "nerve sensing" mode. The nerve sensing mode will use the electrodes to read for action potentials through the GSN. The electrodes may be separate electrodes located on the surface of the catheter device, or may be the one or more electrodes within the needle assembly. Data from the neurostimulatory component and the nerve sensing apparatus will be aggregated to tell the operator that the device is in the position to perform nerve destruction.

After the location of the nerve has been confirmed by a combination of neuro-stimulatory and nerve sensing functions evaluated by the software component of the generator, the vascular puncture mechanism is actuated in the direction of the nerve to perform the ablation. The puncture mechanism may optionally confirm the position using a combination of nerve-sensing, neuro-stimulation with physiologic response, and fluoroscopy identifying anatomic landmarks.

Then the nerve is ablated with radiofrequency ablation by applying an electrical stimulation to the electrode assembly. Electrical energy at about 50 W is transmitted from the power source to the electrode assembly on the needle assembly in proximity to the target nerve, and heating the target nerve and surrounding tissue to approximately 60 C.

Because nerves are able to regenerate, durability of effect is fundamentally related to the length of nerve tissue destroyed. In some cases, it is desirable to ablate a longer length of nerve (compared to intra-vascular ablation), leading to a longer duration of removal of sympathetic activity. Thus, patients will experience relief from heart failure symptoms for a longer period of time. In some cases, it is desirable to control the direction of the ablation modality. By focusing the ablation modality to the length of nerve, the operator can minimize collateral damage to other organs.

Next, procedure success may be evaluated by repeating the combination of nerve-sensing, neuro-stimulation with physiologic response. The device's neurostimulatory component delivers a charge through electrodes strong enough to elicit a nerve response, but not strong enough to damage tissue. The sympathetic response of the GSN will be measured by physiological changes as described above. The nerve-sensing component will detect lack of nerve activity, indication the nerve has successfully been circumferentially lysed. The procedure will be considered incomplete if there is a physiologic response and/or if there is nerve activity sensed by the catheter device. The procedure will be repeated to lyse the nerve circumferentially, at the same site or a different site between two intercostal pairs.

After the procedure is performed, the volume status of the patient improves and the patient is re-evaluated in the clinic one month later. Here the patient is noted to have more energy and exercise level; he/she can walk more than one block of stairs without having to rest. The cardiologist notes that the patient is improved one NYHA Class of severity with fewer hospitalizations.

Embodiments

Embodiment 1. An embodiment comprising a device for treating a medical condition, the device comprising: a catheter having a longitudinal axis and comprising a needle lumen therein that is substantially parallel to or substantially coincident with the catheter longitudinal axis, wherein the needle lumen terminates in a lateral opening at a distal portion of the catheter; and a needle assembly configured to extend within and/or from the needle lumen, the needle assembly comprising: a first needle having a first tip and a second needle having a second tip, wherein the first needle and the second needle are disposed at a needle assembly distal end, the needle assembly having A) a non-bifurcated configuration prior to at least partially extending from the needle lumen and/or the lateral opening, and B) a bifurcated configuration when at least partially extending from the needle lumen and the lateral opening, wherein when the needle assembly is in a bifurcated configuration, the first tip and the second tip are spaced apart by a deployed distance measured from the first tip and the second tip, wherein when the needle assembly is in a non-bifurcated configuration, the first tip and the second tip are spaced apart by a non-bifurcated distance measured from the first tip and the second tip, wherein the deployed distance is larger than the non-bifurcated distance, and wherein when the needle assembly is in the bifurcated configuration, each of the first needle and the second needle are at a non-zero angle relative to the longitudinal axis of the catheter; a first ablation electrode disposed on the first needle, the first ablation electrode in electrical communication with a first source of energy; and a second ablation electrode disposed on the second needle, the second ablation electrode in electrical communication with the first and/or a second source of energy.

Embodiment 2. The device of embodiment 1, wherein when the needle assembly extends from the needle lumen, and is in proximity to a target nerve and energized, the device is configured to ablate a length of the target nerve that is at least as long as or longer than the deployed distance between the first tip and the second tip.

Embodiment 3. The device of embodiment 1 or 2, further comprising a needle tube extending within and/or from the needle lumen, wherein the needle assembly is at least partially disposed within the needle tube, wherein the needle assembly has a bifurcated configuration when at least partially extending from the needle tube.

Embodiment 4. An embodiment comprising a device for treating a medical condition, the device comprising: a catheter having a longitudinal axis; a balloon having a proximal shoulder at a distal portion of the catheter, wherein the balloon is in fluid communication and configured to be inflated with an inflation medium; a needle tube disposed on an outer surface of the balloon, and a needle assembly configured to extend within and/or from the needle tube, the needle assembly comprising: a first needle having a first tip and a second needle having a second tip, wherein the first needle and the second needle are disposed at a needle assembly distal end, the needle assembly having A) a non-bifurcated configuration prior to extending a prescribed distance from the needle tube, and B) a bifurcated configuration when extending a prescribed distance from the needle tube, wherein when the needle assembly is in a bifurcated configuration, the first tip and the second tip are spaced apart by a deployed distance measured from the first tip and the second tip, wherein when the needle assembly is in a non-bifurcated configuration, the first tip and the second tip are spaced apart by a non-bifurcated distance measured from the first tip and the second tip, and wherein the deployed distance is larger than the non-bifurcated distance; a first ablation electrode disposed on the first needle, the first ablation electrode in electrical communication with a first source of energy; a second ablation electrode disposed on the second needle, the second ablation electrode in electrical communication with the first and/or a second source of energy; and wherein when the balloon is inflated, the needle tube moves to a non-zero angle relative to the longitudinal axis of the catheter. The device of embodiment 4, wherein when the needle assembly extends the prescribed distance from the needle tube, and is in proximity to a target nerve and energized, the device is configured to ablate a length of the target nerve that is at least as long as or longer than the deployed distance between the first tip and the second tip.

Embodiment 5. The device of embodiment 4 or 5, wherein the balloon is in fluid communication with the inflatable medium via an inflation tube.

Embodiment 6. The device of any one of embodiments 4-6, wherein the inflation medium comprises a gas or liquid.

Embodiment 7. The device of embodiment 7, wherein the inflation medium comprise air, saline, or water.

Embodiment 8. The device of any one of embodiments 1-8, wherein the first ablation electrode and the second ablation electrode are electrically isolated from each other.

Embodiment 9. The device of any one of embodiments 1-9, wherein the needle assembly is configured to deliver an electric charge in a bipolar manner.

Embodiment 10. The device of any one of embodiments 1-10, wherein the first ablation electrode and/or the second ablation electrode in operative communication with a controller to modulate a power delivered by the first and/or second source of energy.

Embodiment 11. The device of embodiment 2 or 5, wherein the length of the target nerve that is ablated is 10% to 1000% longer than the deployed distance.

Embodiment 12. The device of any one of embodiments 1-12, wherein the deployed distance is from about 1 mm to about 10 cm.

Embodiment 13. The device of any one of embodiments 1-13, wherein the first needle and the second needle comprises a memory material, enabling the needle assembly to change into the bifurcated configuration when not constrained in the needle assembly lumen.

Embodiment 14. The device of any one of embodiments 1-14, further comprising a neurostimulation electrode disposed on an outer surface catheter, the neurostimulation electrode in electrical communication with the first, second or a third source of energy at the proximal end of the device, and configured to stimulate a target nerve.

Embodiment 15. The device of embodiment 15, wherein the neurostimulation electrode is positioned within 0-90 degrees radially of a location on the outer surface of the catheter relative to the longitudinal axis of the catheter on an outer surface thereof.

Embodiment 16. The device of embodiment 16, wherein two or more of the first and second, and third sources of energy are the same or different sources of energy.

Embodiment 17. The device of embodiment 17, wherein two or more of the first, second, and third sources of energy have different energy parameters or the same energy parameters (such as X, Y, Z).

Embodiment 18. An embodiment comprising a device for treating a medical condition, the device comprising: a catheter having a longitudinal axis; a balloon having a proximal shoulder at a distal portion of the catheter, wherein the balloon is in fluid communication and configured to be inflated with an inflation medium; a needle tube disposed on an outer surface of the balloon; a hollow needle having a needle longitudinal axis and configured to extend within and/or from the needle tube, the hollow needle in fluid communication with an ablation medium, the hollow needle having a lateral needle opening for delivering the ablation medium therefrom; and a neurostimulation electrode disposed on an outer surface of the catheter, the neurostimulation electrode in electrical communication with a first source of energy, and configured to stimulate a target nerve; wherein when the balloon is inflated, the needle tube moves to a non-zero angle relative to the longitudinal axis of the catheter, and wherein the device is configured to ablate a length of the target nerve via delivery of the ablation medium through the lateral needle opening.

Embodiment 19. The device of embodiment 19, wherein the balloon is in fluid communication with the inflatable medium via an inflation tube.

Embodiment 20. The device of any one of embodiments 19 or 20, wherein the inflation medium comprises a gas or liquid.

Embodiment 21. The device of embodiment 21, wherein the inflation medium comprise air, saline, or water.

Embodiment 22. The device of any one of embodiments 19-22, wherein the ablation medium comprises a liquid and/or gas.

Embodiment 23. The device of any one of embodiments 19-23, wherein the ablation medium comprises carbon dioxide, ethanol, liquid nitrogen, a conductive substance (e.g., saline, specialized hydrogel, etc.), an alcohol, lidocaine, lidocaine analogues, or a combination thereof.

Embodiment 24. The device of any one of embodiments 19-24, wherein the neurostimulation electrode is positioned within 0-90 degrees radially of a location on the outer surface of the catheter relative to the longitudinal axis of the catheter on an outer surface thereof.

Embodiment 25. The device of any one of embodiments 1-25, further comprising a neurosensory region configured to sense nerve activity of a target nerve.

Embodiment 26. The device of embodiment 26, wherein the neurosensory region is configured to detect action potentials of the target nerve.

Embodiment 27. The device of embodiment 26 or 27, wherein the neurosensory region comprises a neurosensory electrode.

Embodiment 28. The device of any one of embodiments 1-28, wherein the catheter further comprises a radiopaque region.

Embodiment 29. An embodiment comprising a method for treating a medical condition, the method comprising: inserting a catheter into a subject, the catheter having an opening at a distal portion thereof; guiding the catheter using an anatomic landmark to a first position within the subject so as to approximate a location of a target nerve; delivering a first stimulation to the target nerve via a neurostimulation electrode disposed on the catheter; and measuring a physiological response corresponding to the first stimulation, thereby confirming a location of the target nerve.

Embodiment 30. The method of embodiment 30, further comprising, prior to step (d): (a) monitoring a physiological parameter; (b) moving the catheter to a second position within the subject, so as to approximate the location of the target nerve; and (c) delivering a second stimulation to the target nerve via the neurostimulation electrode.

Embodiment 31. The method of embodiment 30 or 31, further comprising, prior to delivering the first stimulation, sensing a nerve activity of the target nerve using a neurosensory region disposed on the catheter.

Embodiment 32. The method of any one of embodiments 30-32, further comprising: extending a needle assembly from the catheter to the target nerve; and ablating a length of the target nerve to provide a treatment for the medical condition.

Embodiment 33. The method of embodiment 33, wherein the needle assembly comprises an ablation electrode.

Embodiment 34. The method of embodiment 33, further comprising, prior to ablating the length of the target nerve, bifurcating the needle assembly to space apart a first needle tip on a first needle from a second needle tip on a second needle, wherein a first ablation electrode is disposed on the first needle, and a second ablation electrode is disposed on the second needle, and wherein the ablating is via the first ablation electrode and the second ablation electrode.

Embodiment 35. The method of embodiment 35, wherein the length of the target nerve comprises is at least as long or longer than a distance between the first needle tip and the second needle tip after bifurcating the needle assembly.

Embodiment 36. The method of embodiment 35 or 36, further comprising, prior to extending the needle assembly from the catheter, expanding a balloon disposed on the catheter so as to orient the needle assembly in a direction that aligns each ablation electrode with the target nerve.

Embodiment 37. The method of any one of embodiments 35-37, wherein ablating the at least the portion of the target nerve comprises delivering radiofrequency energy, microwave energy, or both, to the target nerve.

Embodiment 38. The method of embodiment 33, wherein the needle assembly comprises a hollow needle having a fluid port, wherein the hollow needle is in fluid communication with an ablation medium.

Embodiment 39. The method of embodiment 39, wherein the ablating the length of the target nerve comprises delivering the ablation medium to the target nerve via the fluid port.

Embodiment 40. The method of embodiment 40, wherein the ablation medium comprises carbon dioxide, ethanol, liquid nitrogen, a conductive substance (e.g., saline, specialized hydrogel, etc.), an alcohol, lidocaine, lidocaine analogues, or a combination thereof.

Embodiment 41. The method of any one of embodiments 33-41, further comprising: delivering a third stimulation to the target nerve via the neurostimulation electrode; and confirming an interrupted nerve activity of the target nerve.

Embodiment 42. The method of embodiment 42, wherein the confirming the interrupted nerve activity comprises detecting a lack or insignificant physiological change after delivering the third stimulation.

Embodiment 43. The method of any one of embodiments 33-43, further comprising rotating the catheter so as to position the needle assembly, such that the needle assembly extends from the catheter to the target nerve.

Embodiment 44. The method of any one of embodiments 30-44, wherein guiding the catheter comprises using fluoroscopy using a radiopaque region on the catheter.

Embodiment 45. The method of any one of embodiments 30-45, wherein the anatomic landmark comprises the ninth thoracic vertebra (T9).

While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

What is claimed is:

1. A vascular catheter comprising:
   a. a longitudinal axis;
   b. a distal end;
   c. a proximal end;
   d. a catheter shaft comprising an exit port;
   e. a needle assembly lumen comprising a telescopic needle assembly configurable from a first position to a second position, wherein the telescopic needle assembly is within the catheter in the first position, wherein the telescopic needle assembly extends through the exit port and punctures vascular tissue in contact with the catheter in the second position, the needle assembly comprising:
      (i) a wire electrically coupled to one or more electrodes configured to deliver electrical energy to a tissue in contact with the one or more electrodes, wherein the electrodes are positioned on an exterior lateral surface of a second section of needle assembly;
      (ii) a first section and the second section, the first section surrounding the second section, the second section surrounding the wire, wherein the second section extends outwards from the first section when the needle assembly is in the second position, wherein the second section is fully enclosed within the first section when the needle assembly is in the first position, wherein the first section extends outwards from the needle assembly lumen and the second section extends outwards from the first section when the needle assembly is in the second position, wherein the first section and second section is configured to puncture vascular tissue in contact with the catheter in a straight vector when transitioned to the second position;
   f. a guidewire lumen; and
   g. a catheter tip.

2. The vascular catheter of claim 1, further comprising a base electrode on an outer surface of the catheter.

3. The vascular catheter of claim 2, wherein the base electrode is positioned within 0-90 degrees radially of a location on the outer surface of the vascular catheter relative to the longitudinal axis of the vascular catheter on an outer surface thereof.

4. The vascular catheter of claim 1, further comprising a first electrical circuit electrically coupled to the one or more electrodes, further comprising a second electrical circuit electrically coupled to a base electrode, wherein the catheter is configured to provide electrical energy of differing frequencies to the first electrical circuit and the second electrical circuit.

5. The vascular catheter of claim 1, wherein the needle assembly comprises:
   h. a distal point on the second section;
   i. a first electrode;
   j. a second electrode;
   k. a wire connecting the first electrode and the second electrode to a power source;
   l. an insulating material insulating the first electrode, the second electrode, and the wire from the vascular catheter.

6. The vascular catheter of claim 1, wherein the wire comprises an enamel coated wire or a multi-strain braid.

7. The vascular catheter of claim 1, wherein the first section comprises a first tubular body, wherein the second section comprises a second tubular body, wherein the first tubular body extends outward from the second tubular body, and wherein the first tubular body nests within the second tubular body such that the tubular body is fully or partially contained within the first tubular body.

8. The vascular catheter of claim 7, wherein the needle assembly further comprises a third section comprising a sharp distal point, wherein the second section surrounds the third section, wherein the third section extends outward from the second section.

9. The vascular catheter of claim 7, wherein the first electrode is positioned on the first tubular body, and wherein the second electrode is positioned on the second tubular body.

10. The vascular catheter of claim 7, wherein the first electrode and the second electrode are positioned on the first tubular body, or the second tubular body.

11. The vascular catheter of claim 7, wherein the needle assembly further comprises an electrically insulating material within the needle assembly, wherein the electrically insulating material comprises a dielectric insulator between the first and second tubular bodies.

12. The vascular catheter of claim 1, wherein the one or more electrodes comprises three electrodes, wherein the three electrodes are arranged such that the second electrode is between the first and third electrodes, and wherein the second electrode is a negative electrode and the first and third electrodes are positive electrodes, or wherein adjacent electrodes have opposite polarity.

13. The vascular catheter of claim 12, wherein the catheter is configured to permit ablation between the first and second electrode, or the second and third electrode.

14. The vascular catheter of claim 1, further comprising an electrically insulating material in contact with the wire, wherein the electrically insulating material comprises a dielectric, a dielectric washer, or a polyimide liner.

15. The vascular catheter of claim 1, wherein when the needle assembly extends a prescribed distance from the exit port and is in proximity to a target nerve when in the second position, and is configured to ablate a length of the target nerve that is at least as long as the deployed distance between the first and second tubular bodies.

16. The vascular catheter of claim 1, wherein the needle assembly is configured to deliver an electric charge in a bipolar manner.

17. The vascular catheter of claim 1, wherein the one or more electrodes comprises a silk-screened electrode.

18. The vascular catheter of claim 1, further comprising a rotary electrical connector configured to rotate the needle assembly.

19. The vascular catheter of claim 1, further comprising an electrode advancer configured to extend the needle assembly and one or more electrodes through the exit port.

20. The vascular catheter of claim 1, wherein the needle assembly further comprises one or more marker bands configured to provide an indication as to positioning of the catheter relative to a vein, with fluoroscopic imaging, or indicate a relative position of the catheter within a vein, artery, or vessel.

* * * * *